(12) United States Patent
Wieland

(10) Patent No.: US 8,795,977 B2
(45) Date of Patent: Aug. 5, 2014

(54) METHOD FOR SCREENING A POTENTIAL MODULATOR COMPOUND OF A TASTE RECEPTOR

(75) Inventor: Kerstin Wieland, Vlaardingen (NL)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/510,963

(22) PCT Filed: Nov. 29, 2010

(86) PCT No.: PCT/EP2010/068399
§ 371 (c)(1),
(2), (4) Date: May 21, 2012

(87) PCT Pub. No.: WO2011/067202
PCT Pub. Date: Jun. 9, 2011

(65) Prior Publication Data
US 2012/0276563 A1 Nov. 1, 2012

(30) Foreign Application Priority Data
Dec. 2, 2009 (EP) .................................... 09177694

(51) Int. Cl.
*C12Q 1/66* (2006.01)

(52) U.S. Cl.
USPC ............................................................ 435/8

(58) Field of Classification Search
CPC . C12Q 1/66; G01N 33/5041; G01N 2333/726
USPC .............................................. 435/8; 536/23.4
See application file for complete search history.

(56) References Cited

U.S. PATENT DOCUMENTS

| | | | |
|---|---|---|---|
| 6,110,693 A * | 8/2000 | Barak et al. ................... 435/7.2 |
| 7,488,583 B2 * | 2/2009 | Westwick et al. ............. 435/7.1 |
| 2003/0049643 A1 * | 3/2003 | Barak et al. ...................... 435/6 |
| 2003/0232407 A1 * | 12/2003 | Zoller et al. ................ 435/69.1 |
| 2006/0099646 A1 * | 5/2006 | Heding ......................... 435/7.1 |
| 2007/0037212 A1 | 2/2007 | Li et al. |
| 2011/0160081 A1 * | 6/2011 | Javitch et al. ..................... 506/9 |
| 2011/0275134 A1 * | 11/2011 | Bouvier et al. ............... 435/188 |
| 2012/0077210 A1 * | 3/2012 | Trowell et al. ................ 435/7.9 |

FOREIGN PATENT DOCUMENTS

| | | |
|---|---|---|
| EP | 1309606 B1 | 8/2008 |
| WO | WO02059267 A2 | 8/2002 |
| WO | WO2004034054 A2 | 4/2004 |
| WO | WO2004065963 A2 | 8/2004 |

OTHER PUBLICATIONS

Perroy J. et al. Real Time Monitoring of Ubiquitination in Living Cells by BRET. Nature Methods 1(3)203-208, Dec. 2004.*
Bacart J. et al. The BRET Technology and Its Application to Screening Assays. Biotechnology 3(3)311-324 Mar. 2008.*
Boute et al., Aug. 2002, The use of resonance energy transfer in high-throughput screening: BRET versus FRET, Trends in Pharmacological Sciences, vol. 23(8), pp. 351-354.
European Search Report, Application No. EP 09 17 7694, completed Apr. 22, 2010.
Written Opinion, International Application No. PCT/EP2010/068399.

* cited by examiner

*Primary Examiner* — Ralph Gitomer
(74) *Attorney, Agent, or Firm* — Ellen Plotkin

(57) ABSTRACT

A method for screening a potential modulator compound of a taste receptor wherein use is made of a BRET technique.

7 Claims, 3 Drawing Sheets

METHOD FOR SCREENING A POTENTIAL MODULATOR COMPOUND OF A TASTE RECEPTOR

This application is a National Stage application filed under Rule 371 based upon PCT/EP2010/068399 filed Nov. 29, 2010 which claims priority to EP application 09177694 filed Dec. 2, 2009.

FIELD OF THE INVENTION

The invention relates to a method for screening a potential modulator compound of a taste receptor, wherein use is made of a BRET technique.

BACKGROUND OF THE INVENTION

Flavour is part of our primary sensory system that controls food intake[1] so that we consume pleasant (i.e. nutritional food) and avoid unpleasant food (containing potential toxins). Flavour is a sensation formed from visual, taste, aroma and mouth feel inputs. However, food choice and the amount we consume seem to be driven more by three of the five basic tastes (salt, sweet and umami) and is less affected by the other flavour attributes. Foods containing these attributes tend to be the ones preferred by humans as well as most mammals; in that context umami serves as a marker for proteins and sweetness for carbohydrates.

Recently the receptors involved in the detection of these taste modalities have been identified and cloned[2-4], thus making it possible to investigate activation of taste receptors in vitro. The receptors for sweet, umami and bitter belong to the class of G-protein coupled receptors (GPCRs), whereas saltiness and sourness are most likely detected by ion channels.

Sweetness is sensed by the heterogeneous receptor dimer T1R2/T1R3, whereas umami is primarily detected by the T1R1/T1R3 receptor[2], although other receptors have also been implicated to be involved in umami as well[5].

Various cellular systems can be used for measuring in vitro receptor activation with good correlation to the in vivo sensory perception, including heterologous expression of taste receptors in mammalian cell lines like HEK293 cells[2, 6-9]. The currently available functional in vitro screening systems usually make use of promiscuous G-proteins such as Gα15, Gα16 or chimeras of these G-proteins with various adaptations of the C-terminal domain; this will direct the signalling cascades of receptors of interest to PLC (phospholipase C) and release of intracellular calcium. Although this approach has been very successful for investigating pure compounds, it has proven to be more difficult for testing extracts or complex samples: due to the universal nature of the G-proteins they are not only able to couple to the recombinant receptors (over) expressed in the screening cell lines, but also to many receptors which are endogenously present at low levels. This can result in unspecific calcium signals induced by agonists present in natural mixtures activating these endogenous receptors. Moreover, extracts or complex test samples often also contain substances, which elevate intracellular calcium by other means than via GPCRs, and these signals will be indistinguishable from receptor-induced calcium release. The high unspecific background signal observed for most natural mixtures prevents direct screening of these samples without extensive fractionation procedures. It is to be noted that the use of such extracts or complex samples is quite common when evaluating food material for example.

Therefore there is still a need for an improved screening method for a potential modulator compound of a taste receptor, wherein this method does not have each of the drawbacks of existing methods.

DESCRIPTION OF THE INVENTION

In a first aspect there is provided a method for screening a potential modulator compound of a taste receptor, wherein use is made of a BRET (Bioluminescence Resonance Energy Transfer)(10, 11) technique. Each feature of this method is extensively defined below.

A preferred method comprises the following steps:
a) providing a cell expressing a taste receptor fused to a luminescent protein such as a luciferase protein and a fluorescent protein fused to a β-arrestin or inducing their expression,
b) challenging the cell obtained in step a) with a potential modulator compound and,
c) comparing a BRET signal of the cell obtained in step b) with a BRET signal of the cell obtained in b) in the absence of the potential modulator.

Alternatively, in the first aspect the invention provides a method for identifying a compound which modulates a taste receptor, wherein the method comprises the steps of: (a) providing a cell expressing (i) a taste receptor fused to a luminescent protein and (ii) a fluorescent protein fused to a β-arrestin; (b) contacting the cell with a potential modulator compound and determining the BRET signal; and, (c) comparing the BRET signal obtained in step (b) with a BRET signal obtained from the cell in the absence of the potential modulator compound, wherein a difference between the BRET signal as obtained in (b) and the BRET signal obtained in the absence of the potential modulator compound, is indicative of the potential modulator compound being a compound which modulates a taste receptor.

Our invention uses a BRET technique or assay which confers more specificity to a method of the invention: a taste receptor of interest is fused with a donor luminescent protein such as a luciferase protein, no other cellular components can influence a signal originating from said receptor and cause a BRET signal. This is of special interest with respect to natural mixtures often available for screening in order to identify a potential modulator compound of a taste receptor: neither components activating endogenous receptors nor substances previously causing unspecific elevation of intracellular calcium via other pathways are able to cause a BRET signal. The read-out window is solely focussed on the receptor-luminescent fusion protein, thus making this method exceptionally useful for directly investigating receptor activation using non-purified, crude extracts with high specificity.

A method of the invention is based on the ability of a taste receptor being a GPCRs (G Protein Coupled Receptors) to translocate β-arrestin upon receptor stimulation and utilises a BRET assay for measuring receptor-β-arrestin interaction by measuring energy transfer between fusion proteins containing the energy donor (a luminescent protein such as a luciferase) and the energy acceptor protein (a fluorophore, typically a fluorescent protein), which absorbs light at a given wavelength and reemits light at a longer wavelength[10]. In the case of GPCR activation assay, a luminescent protein such as a luciferase is fused to the C-terminal of the receptor, and a fluorescent protein to a β-arrestin. If a receptor is activated, cytosolic β-arrestin is recruited to the plasma membrane and targets the receptor for internalisation. During the interaction of β-arrestin/fluorescent protein with the luminescent protein-fused receptor, donor and acceptor proteins are in close proximity and will induce a BRET signal.

A BRET technique is therefore a technique or assay which can generate a signal or a BRET signal, said signal being an energy transfer between a taste receptor fused to a luminescent protein and a fluorescent protein and said signal reflecting the activation of said taste receptor due to the presence of a potential modulator compound.

Step a) of a method of the invention provides a cell expressing a taste receptor fused to a luminescent protein such as a luciferase protein and a fluorescent protein fused to a β-arrestin or inducing their expression. Step a) of a method of the invention can also provide a cell expressing (i) a taste receptor fused to a luminescent protein and (ii) a fluorescent protein fused to a β-arrestin.

A taste receptor may be any receptor known to be associated with taste in the mouth of a human. A taste receptor may also be any receptor which is later discovered as being involved in a taste perception. A taste receptor may be expressed in the tongue: a MSG (Mono Sodium Glutamate) or umami receptor, a sweet receptor, a bitter receptor or a fat receptor. A receptor known to be involved in sweet perception is a heterodimer comprising two subunits T1R2 (Taste 1 Receptor 2) and T1R3 (Taste 1 Receptor 3). A receptor known to be involved in umami perception is another heterodimer comprising two subunits T1R1 (Taste 1 Receptor 1) and T1R3. Another MSG or umami receptor is composed of one or more subunits of mGluR4 (a or c) (Metabotropic Glutamate Receptor 4 (a or c)). A bitter receptor is composed of one or more subunits of a TAS2 (Taste 2) receptor. A fatty acid receptor is composed of one or more subunits of GPR120 (G-Protein coupled receptor 120). A preferred nucleic acid sequence representing a human T1R1 is SEQ ID NO:1. A corresponding preferred amino acid sequence representing a human T1R1 protein is represented by SEQ ID NO:2. A preferred nucleic acid sequence representing a human T1R3 is SEQ ID NO:3. A corresponding preferred amino acid sequence representing a human T1R3 protein is represented by SEQ ID NO:4.

Within the context of the invention, a taste receptor may also be a receptor involved in nutrient/fatty acid sensing in the gut of a human. Such receptors include: the calcium-sensing receptor, the G protein-coupled receptor family C, group 6, subtype A (GPRC6A), the taste receptor dimer T1R1/T1R3, which is sensing L-alpha-amino acids, the carbohydrate-sensing T1R2/T1R3 receptor dimer, the proteolytic degradation product sensor GPR93 (also termed GPR92), and the free fatty acid (FFA) sensing receptors FFA1, FFA2, FFA3, GPR84, and GPR120[5]. Each of the receptor identified in Table 3 may be used in a method of the invention. A preferred nucleic acid molecule encoding each of these receptors is given in the sequence listing. A corresponding preferred encoded receptor is also given in the sequence listing (see also Table 3).

A method of the invention is exemplified using a taste receptor comprising a T1R1 and a T1R3 subunit and using a luciferase as a luminescent protein. However, the skilled person will understand that the invention is not limited to a method using said heterodimer and this luminescent protein. The invention provides a cell expressing a taste receptor, preferably a T1R1, T1R3 heterodimer. Said taste receptor is preferably functional. It means that in a screening method of the invention carried out without adding a potential modulator, a detectable BRET signal is present when a substance known to activate this taste receptor is added to said cell. For each taste receptor, such substance is known. Examples of such substances, i.e. agonists are identified in Table 1.

The invention also provides a step a) wherein a cell is provided expressing a taste receptor fused to a fluorescent protein and a luminescent protein such as a luciferase protein fused to a β-arrestin or inducing their expression. Each feature defined herein for a luminescent protein such as a luciferase protein when fused to a taste receptor also holds for a luminescent protein such as a luciferase protein when fused to a β-arrestin. Each feature defined herein for a fluorescent protein when fused to a β-arrestin also holds for a fluorescent protein when fused to a luminescent protein such as a luciferase protein. Thus the invention also provides a method wherein the taste receptor is fused to a fluorescent protein and the β-arrestin to a luminescent protein. More generally, the skilled person will understand that any embodiment of the invention wherein a luminescent protein is fused to the taste receptor and a fluorescent protein is fused to the β-arrestin can be replaced by an otherwise identical embodiment wherein a fluorescent protein is fused to the taste receptor and a luminescent protein is fused to the β-arrestin.

The invention identifies a preferred nucleic acid molecule represented by a nucleic acid sequence, respectively an encoded protein represented by an amino acid sequence to be used to obtain a cell for use in a method of the invention. However, each of the nucleic acid sequence as identified herein may be replaced by a naturally occurring form, a variant containing a SNP (Single Nucleotide Polymorphism), an alternatively spliced form, a combination of form, or any functional variant known in the art. A nucleic acid molecule as defined herein should be functional when expressed in a cell as earlier explained herein. A variant of a nucleic acid sequence may be a fragment of this nucleic acid sequence. A preferred variant contains a silent mutation. Alternatively, or in combination, a nucleic acid sequence variant may also be obtained by introduction of a nucleotide substitution which does not give rise to another amino acid sequence, but which corresponds to the codon usage of the host cell wherein said nucleic acid sequence will be expressed. Preferably, a nucleic acid sequence variant is such that starting from any one of the nucleic acid sequence as earlier defined herein, one or more nucleotides from the 5 and/or 3' end have been deleted. Alternatively or in combination, a nucleic acid sequence variant is preferably a nucleic acid sequence isolated from another organism and/or another family member of the nucleic acid sequence as earlier defined herein. All these variants can be obtained in a typical approach, using cDNA or genomic libraries from a chosen species, e.g. mammalian species such as humans. The library can be subsequently screened with one of the nucleic acid sequences as earlier defined herein or part thereof by hybridization under stringent conditions. Stringent conditions mean prehybridization and hybridization at 42° C. in 5×SSPE, 0.3% SDS, 200 pg/ml sheared and denatured salmon sperm DNA, and 50% formamide. Subsequently, the hybridization reaction is washed three times for 30 minutes each using 2×SSC, 0.2% SDS and 75° C. Alternatively or in combination, a nucleic acid sequence variants may be obtained by searching for amino acid identities and/or similarities in databases and synthesis of a nucleic acid sequence encoding an suitable amino acid sequence identified in the search.

Human is a preferred species. According to another preferred embodiment, a nucleic acid sequence variant is an allelic variant. An allelic variant denotes any of two or more alternative forms of a gene occupying the same chromosome locus. Allelic variation arises naturally through mutation, and may result in phenotypic polymorphism within populations. According to another preferred embodiment, a nucleic acid sequence variant differs from any of the nucleic acid sequences as earlier defined herein by virtue of the degeneracy of the genetic code.

More explanation as to the nucleic acid molecule used is given in the section entitled "Nucleic acid molecule defined by a SEQ ID NO and Sequence identity". In a preferred embodiment, a nucleic acid molecule used originates from a human. More preferably, a nucleic acid molecule as defined in this preferred embodiment is for functional expression in a mammalian, even more preferably a human cell. The use of a sequence, which is highly homologous (identity of at least 85%) with a human sequence is attractive since we may expect this nucleic acid molecule will be expressed and functional in mammalian, preferably a human cell. Furthermore, this sequence is so highly homologous with a human sequence that we expect that the cell type hence prepared will mimic human taste more efficiently than cell type prepared with a sequence having a lower identity to a human sequence. Even more preferably, the identity as defined earlier herein is 85% or more, even more preferably 90% or more, even more preferably 91% or more, even more preferably 92% or more, even more preferably 93% or more, even more preferably 94% or more, even more preferably 95% or more, even more preferably 96% or more, even more preferably 97% or more, even more preferably 98% or more, even more preferably 99% or more, and most preferably 100%.

In the invention, a nucleic acid molecule encoding a taste receptor or a subunit thereof is fused to a luminescent protein such as a luciferase protein. In a preferred embodiment, a luminescent protein is a luciferase protein. A luminescent protein such as a luciferase protein is preferably fused at the C terminal part of the receptor which is its intracellular part. The skilled person will understand that a luminescent protein such as a luciferase protein may be fused anywhere in the intracellular part of a taste receptor. However, the protein hence obtained should be still functional; i.e. activatable. Therefore when a luminescent protein such as a luciferase protein has been fused somewhere in the intracellular part of a taste receptor, it is preferred that such a protein hence obtained which is preferably a recombinant protein is tested as to its functionality. In a preferred embodiment, a luminescent protein such as a luciferase protein is fused at the end of the C terminal part of a taste receptor or as close possible to the end of the C terminal part of said taste receptor. As close possible to the end of the C terminal part of said taste receptor preferably means that the first amino acid of a luminescent protein such as a luciferase protein is present at the place corresponding to the last amino acid of the C terminal part of a taste receptor or 1, 2, 3, 4, 5, 6, 7, 8, 9, 10, 11, 12, 13, 14, 15, 16, 17, 18, 19, 20 amino acid before the last amino acid of the C terminal part of a taste receptor. A luciferase may be a Firefly luciferase or may be from any *Renilla* species. A preferred nucleic acid molecule encoding a luciferase has been improved with humanized codon in order to improve its expression level in a mammalian cell. A more preferred nucleic acid molecule encoding a preferred luciferase is given as SEQ ID NO:77 A preferred encoded luciferase protein is identified as SEQ ID NO:78 The skilled person knows how to fuse two nucleic acid molecules in frame. In the case of a taste receptor having more than one distinct subunit as the preferred T1R1 and T1R3 subunits of a umami receptor, one may fuse each subunit with a luminescent protein such as a luciferase protein or only one of the subunits. This holds for each taste receptor, i.e. the skilled person will understand that this also holds for other (hetero)multimeric taste receptors. If a taste receptor has more than one distinct subunit, each subunit may have been fused to a luminescent protein such as a luciferase protein. Alternatively, only one or more type of subunit will have been fused to a luminescent protein such as a luciferase.

In the invention, a fluorescent protein is fused to a β-arrestin. A preferred fluorescent protein is a green fluorescent protein (GFP). More preferred is GFP2.

A preferred β-arrestin is a human or mammalian β-arrestin. More preferably the β-arrestin is a non-visual β-arrestin such as e.g. β-arrestin 2 or 3. Most preferably the β-arrestin is a β-arrestin 2 which is represented by SEQ ID NO:79. A preferred nucleic acid molecule encoding said β-arrestin 2 is represented by SEQ ID NO:80. An even more preferred β-arrestin 2 has been described in WO2004/065963 or in WO 2004/034054. The fusion between a fluorescent protein and a β-arrestin is also known to the skilled person. In a method of the invention, each nucleic acid molecule (i.e. the one encoding a taste receptor fused to a luciferase and the one encoding a fluorescent protein fused to a β-arrestin) is present in a nucleic acid construct. Each construct is introduced into a cell.

A cell of the invention therefore comprises a nucleic acid construct as defined herein. The skilled person will know that the choice of the cell depends largely on the origin of the nucleic acid sequence encoding the taste receptor. Any cell can be chosen as long as a taste receptor as expressed is functional. Preferably, the expression of a taste receptor and/or of a β-arrestin is stable, optionally inducible. Alternatively, the expression of a taste receptor and/or of a β-arrestin is transient. Inducible expression is extensively explained in the section "expression of a taste receptor". Preferably, a cell is a prokaryote or an eukaryote cell. More preferably, the cell is an insect or a mammalian cell. Even more preferably, the mammalian cell is a human cell. Examples of mammalian cells are HEK293, HEK293T, MDCK, CHO, COS, NIH3T3, Swiss3T3, BHK, and A549. Even more preferably, a cell is a mammalian cell such as HEK293. A cell of the invention may be seen as a recombinant cell. A cell of the invention is advantageously used in a method of the invention.

Depending on the type of expression system chosen, the skilled person may possibly adapt the culture conditions to obtain a most favorable expression level of a taste receptor and of a β-arrestin. In the case of an inducible expression system, the skilled person may also possibly optimize an inducing condition. The time period of induction of the expression and the temperature during induction of the expression could also possibly be optimized. According to a preferred embodiment, at the onset of the induction of expression of a taste receptor, sub-confluent cells are placed in a 96 well plate with a suitable culture medium. Sub-confluent preferably means 70% confluent, more preferably 80% confluent. In a preferred embodiment, the inducing agent added is tetracycline or doxycyclin when using an inducible expression system, preferably a tetracyclin-regulated promoter.

In an embodiment, cells may be transiently transfected with a nucleic acid molecule encoding a taste receptor fused to a luminescent protein such as a luciferase protein and a nucleic acid molecule encoding a fluorescent protein fused to a β-arrestin. If a taste receptor has more than one distinct subunit, one may use one nucleic acid molecule per subunit. Alternatively one may use one single nucleic acid molecule comprising more than one type of subunit. Transient transfection may be carried out using Lipofectamine 2000 according to the manufacturers' protocol. Briefly, cells may be seeded at a density of $2 \times 10^5$ cells per well (12-wells plate, 1 ml medium/well), aiming at a confluency of about 80-90% the next day. After 24 h, a nucleic acid molecule encoding a taste receptor fused to a luminescent protein such as a luciferase may be co-transfected with a nucleic acid molecule encoding a fluorescent protein fused to a β-arrestin. A total of 15 μg of total DNA may be used per well. A mixture comprising said DNA may be incubated for 30 minutes at room temperature, added to each well and the cells allowed to grow for 48 hours. A BRET measurement may be carried out 48 h-52 h after transfection. Alternatively, a nucleic acid molecule encoding a taste receptor fused to a luminescent protein such as a luciferase protein may be transfected into cells stably expressing a fluorescent protein fused to a β-arrestin using the same protocol as described above. A preferred transfection protocol is described in the experimental part for HEK293 cells.

In a preferred embodiment, a taste receptor comprises a T1R1 and a T1R3 subunit and at least one of the subunits is fused to a luminescent protein such as a luciferase: T1R1 or T1R3 or both subunits. Preferably, a luciferase protein is a *Renilla* luciferase. A preferred nucleic acid sequence encoding a preferred T1R1 subunit fused to a *Renilla* luciferase is represented by SEQ ID NO:5. A corresponding preferred encoded amino acid sequence is represented by SEQ ID NO:6. A preferred nucleic acid sequence encoding a preferred T1R3 subunit fused to a *Renilla* luciferase is represented by SEQ ID NO:7. A corresponding preferred encoded amino acid sequence is represented by SEQ ID NO:8.

In a further preferred embodiment, a fluorescent protein fused to a β-arrestin is a GFP protein, preferably a GFP2 and β-arrestin is a β-arrestin 2.

Even more preferably, a taste receptor comprises a T1R1 and a T1R3 subunit and each subunit is fused to a luminescent protein such as a luciferase protein, preferably to a luciferase, more preferably to a *Renilla* luciferase and a fluorescent protein fused to a β-arrestin is a GFP protein, preferably a GFP2 and β-arrestin is a β-arrestin 2.

It is further encompassed by the present invention that a luminescent protein may be a luciferase protein. Alternatively, a luminescent protein may be another suitable energy donor. It is also encompassed by the present invention that a GFP may be replaced by another suitable energy acceptor. Theoretically any fluorescent protein or molecule defined as being a member of a structurally homologous class of proteins that can form a visible wavelength chromophore within its own polypeptide sequence could be used. Several fluorescent proteins have already been used in a BRET technology (see Bacart J. Et al, (2008) Biotechnol. J. 3:311-324 and Pfleger K. D., et al, (2006), Nature Methods, 3: 165-174).

A luminescent protein such as a luciferase and a GFP are herein presented as a preferred energy donor and energy acceptor respectively. Each of the features defined for a luminescent protein such as a luciferase or a GFP also holds for any other energy donor or energy acceptor respectively.

Therefore, in a method of the invention:
(a) at least one of the subunits of a taste receptor, preferably at least one of T1R1 and T1R3 is fused to a luminescent protein such as a luciferase protein or each subunit of a taste receptor, preferably T1R1 and T1R3 are each fused to a luminescent protein such as a luciferase protein
and/or
(b) a fluorescent protein fused to a β-arrestin is a GFP protein, preferably the GFP is a GFP2 and/or β-arrestin is a β-arrestin 2.

Alternatively, in a method of the invention:
(a) at least one of the subunits of a taste receptor, preferably at least one of T1R1 and T1R3 is fused to a fluorescent protein or each subunit of a taste receptor, preferably T1R1 and T1R3 are fused to a fluorescent protein
and/or
(b) a luminescent protein is fused to a β-arrestin.

Alternatively, in a method of the invention:
(a) the taste receptor is a T1R1, T1R3 heterodimer, wherein at least one of the subunits T1R1 and T1R3 is fused to a luminescent protein, and wherein a fluorescent protein is fused to a β-arrestin; or,
(b) the taste receptor is a T1R1, T1R3 heterodimer, wherein at least one of the subunits T1R1 and T1R3 is fused to a fluorescent protein, and wherein a luminescent protein is fused to a β-arrestin.

Preferably in a method of the invention at least one of: (a) the luminescent protein is a luciferase; (b) the fluorescent protein is a GFP; and, (c) the β-arrestin is a non-visual β-arrestin. More preferably, at least one of: (a) the luciferase is a *Renilla* luciferase; and, (b) the non-visual β-arrestin is a β-arrestin 2.

Step b) comprises challenging a cell as obtained in step a) with a potential modulator compound.

In this context, challenging may mean contacting a cell obtained in step a) with a potential modulator compound.

A potential modulator compound of a taste receptor is herein defined as a compound that can block, inhibit, modulate or enhance a taste perception by blocking, inhibiting, modulating or enhancing the capacity of a taste receptor to be activated and therefore to transduce an intracellular signal into a cell. Any molecule, e.g. any organic molecule, either naturally occurring or synthetic, e.g., protein, oligopeptide, small organic molecule, polysaccharide, lipid (e.g. sphingolipid), fatty acid, polynucleotide, oligonucleotide, etc can be tested in a method of the invention. The potential modulator compound can be in the form of a library of compounds, such as a combinatorial or randomized library that provides a sufficient range of diversity.

The potential modulator compound will usually be present in an aqueous sample solution. Such an aqueous sample solution can comprise at least one of (a) a food product; (b) an extract of a food product; and (c) an extract of biomass, preferably an extract of edible biomass. Thus, the sample solution may comprise a liquid food product or a dilution thereof. The liquid food product may e.g. be a beverage or sauce like e.g. a soy sauce. The aqueous sample solution may also comprise an extract of a food product e.g. an extract of a solid food product (e.g. cheese) or a fat food product. Or the aqueous sample solution may comprise an extract of biomass from at least one of a plant, an animal and a microorganism. Thus, the aqueous sample solution may be an comprising soluble molecules from at least one of a plant, an animal and a microorganism. The aqueous sample solution may thus comprise an extract from a fermented food product. In a preferred embodiment the sample solution comprises a tomato extract. The extracts are further as defined herein below and may be prepared as defined herein below.

A advantage of the method of the invention is that it allows identification of potential modulators in complex samples. Thus preferably the aqueous sample solution is a complex sample solution. The aqueous sample solution can be a mixture comprising at least two distinct organic molecules, preferably comprising at least 3, 4, 5, 6, 7, 8, 9, 10, 11, 12, 13, 14, 15, 16, 17, 18, 19, 20 or more than 50 or more than 100. The number of compounds is preferably assessed as identified below. An aqueous sample solution may be defined as a complex sample solution when it comprises more than 10 distinct organic molecules, preferably more than 10 distinct potential modulators. It is further understood that the aqueous sample solution will usually be a solution of undefined composition, as opposed to e.g. reference solution comprising a predetermined amount of one or more defined modulators.

Thus a solution of undefined composition is a solution comprising compounds whose identity and/or concentration is not known or defined.

The aqueous sample solution preferably is a solution comprising only solubles. Insolubles may be removed from the sample solution by means known in the art and described herein below for extracts. The aqueous sample solution further can be adjusted to be physiologically compatible with the cells provide in step a) by adjusting the solution to a physiologically acceptable pH and osmotic value.

In a preferred embodiment, such a modulator is present in an extract. An extract is a mixture comprising at least two distinct molecules, at least 3, 4, 5, 6, 7, 8, 9, 10, 11, 12, 13, 14, 15, 16, 17, 18, 19, 20 or more than 50 or more than 100. The number of compounds is preferably assessed as identified below. An extract may be defined as a complex extract when it comprises more than 10 distinct molecules. An extract is a mixture comprising at least two distinct organic molecules, at least 3, 4, 5, 6, 7, 8, 9, 10, 11, 12, 13, 14, 15, 16, 17, 18, 19, 20 or more than 50 or more than 100. The number of compounds is preferably assessed as identified below. An extract may be defined as a complex extract when it comprises more than 10 distinct organic molecules. An extract may not be purified and may be a plant-based extract, preferably a tomato extract or an animal-based extract and/or a food-based extract. An extract may be a food-based or food-derived extract. A food-based or food-derived extract may be seen as a food composition or a food product or as based on or derived from a food composition or food product. The identity of the extract, its composition and the way an extract has been prepared is not important for the invention. On the contrary, the advantages of the invention is that potentially from each extract, one may identify a potential modulator of a taste receptor using a method of the invention.

An extract may be a not-purified mixture obtained by using a solvent (e.g. water) or a solvent mix (e.g. water/alcohol) for extraction of plant, animal and/or microbial biomass, e.g. fresh, processed, fermented and/or dried plant or animal or food material containing all the soluble compounds from said material, preferably in a similar ratio as present in the original material and preferably corrected according to their solubility.

The number and concentration of compounds in an extract may be assessed knowing their presence in the original plant or animal or food material, their solubility in the solvent system used and known techniques to the skilled person such as using chromatography (HPLC, GC) and/or spectroscopic technique (NMR, Mass).

The preparation of extracts to be used in the invention usually involves at least two steps: 1) a solubilisation and/or homogenisation step; and 2) a step wherein insolubles, and optionally non-aqueous phases or solvents, are removed. A possible way of producing a suitable extract may be the treatment of a plant or animal or food material, which can be pre-processed (e.g. by cutting, macerating, drying, powdering etc.) by a suitable solvent (e.g. water, alcohol) or solvent mix (e.g. water/alcohol) under usual process conditions (e.g. heating, stirring, grinding,) and downstream processed (e.g. filtration, centrifugation, drying).

In a preferred method, a known activator of a taste receptor is further added in step b). Preferred known activators of a taste receptor have already been identified in table 1. An activator may be used in the search for an inhibitor: a taste receptor is first contacted with an activator to generate a BRET signal (i.e. a higher signal than the basal activity of said receptor). Subsequently, a potential inhibitor compound is contacted together with said activator. If a generated signal is reduced, said potential inhibitor compound is an inhibitor. An activator is preferably used in this context to increase the level of receptor activation which will then be lowered by the inhibitor; this increases the readout window and thereby the sensitivity.

Step c) comprises comparing a BRET signal of the cell obtained in step b) with a BRET signal of the cell obtained in b) in the absence of a potential modulator compound. Alternatively, step c) comprises comparing the BRET signal obtained in step b) with a BRET signal obtained from the cell in the absence of the potential modulator compound, wherein a difference between the BRET signal as obtained in b) and the BRET signal obtained in the absence of the potential modulator compound, is indicative of the potential modulator compound being a compound which modulates a taste receptor.

A BRET technique or assay leading to the generation of a BRET signal may be any BRET technique known to the skilled person. Any known variant of a luminescent donor luminescent protein such as a luciferase protein which is fused to a taste receptor may be used. The same holds for a luminescent acceptor also called fluorophore or fluorescent protein or energy acceptor protein such as a β-arrestin fused to a fluorescent protein. Depending on the identity of the luminescent donor and the luminescent acceptor, one will use a BRET 1 or BRET2 or BRET3 technique. The identity of proteins, conditions and wave lengths used for several BRET assays are known to the skilled person, see for example in Bacart J. et al (2008), Biotechnol. J. 3: 311-324. However, each of the proteins used in a BRET technique may be modified to improve their spectrum properties, making them more suitable to a BRET technique. Preferably a BRET2 technique is used since it is expected to provide a better sensitivity and efficiency: better separation of the involved wavelength leading to an easier detection of a BRET signal.

Upon receptor stimulation with a potential modulator compound preferably present in an extract, a β-arrestin protein fused to a fluorescent protein interacts with the activated taste receptor thus bringing a fluorescent protein in close proximity with a luminescent protein such as a luciferase fused to said activated taste receptor, making energy transfer between these two proteins possible and generating a BRET signal. In the case of BRET2, the assay is preferably as follows: in the presence of oxygen, a luciferase catalyses the transformation of the substrate DeepBlueC into coelenteramide, which can be measured at 395-410 nm. If a fluorescent protein is in close proximity to a luminescent protein such as a luciferase and energy transfer takes place, the emission will shift to 510 nm; this is referred to as a BRET signal and is expressed as a ratio between the acceptor (a fluorescent protein) and the donor (a luminescent protein such as a luciferase). A BRET signal is herein defined as a detectable BRET signal: a ratio which is higher than 0. In order to ensure that a BRET signal is exclusively caused by a specific activation of a taste receptor, we preferably compare a BRET signal obtained with cells expressing a taste receptor fused to a luminescent protein such as a luciferase protein and a fluorescent protein fused to a β-arrestin to a BRET signal obtained with cells not expressing said receptor and/or with cells not expressing a taste receptor fused to a luminescent protein such as a luciferase protein and/or with cells not expressing a fluorescent protein fused to a β-arrestin. The skilled person knows how to carry out a BRET assay. Fluorescence is typically measured on a fluorescence plate reader. In one embodiment, we may use a Mithras LB 940 plate reader (Berthold Technologies). The protocol we may use is essentially the same as described by Packard BioOne or published protocols[13] with slight modifications: cells may be transfected as described earlier herein. 48 h after transfection cells may be harvested and taken up in a BRET buffer (D-PBS containing 2 μg/ml Aprotinin) at a density of $2 \times 10^6$ cells/ml. After leaving the cells for 1 hour at room temperature for equilibration, 30 μl containing approximately $1 \times 10^5$ cells may be transferred to each well of a white 96 well plate. 10 μl of a potential modulating compound or extract (or buffer) and 10 μl of the substrate coelenterazine (final concentration 5 μM) may be added simultaneously to the cells using the injectors.

Immediately after the final injections, repeated sequential readings will be taken at the specific emission wavelength of the donor and the specific emission wavelength of the acceptor, taking the substrate used for generating the luminescent signal into account. A BRET signal may be determined as the ratio between the light signal measured for an acceptor protein and the light signal measured for a donor protein.

If the BRET technique is a BRET1 technique, the donor is *Renilla* luciferase [Rluc] and coelenterazine h as substrate; the acceptor is enhanced yellow fluorescent protein [enhanced YFP], YFP topaz, YFP citrine, YFP venus, YPet.).

Immediately after the final injections, repeated sequential readings will be taken at a wavelength covering the peak of the specific emission wavelength of the Rluc/coleneterazine h (480 nm) and the peak of the specific emission wavelength of the acceptor (530 nm). A BRET signal may be determined as the ratio between the light signal measured for an acceptor protein and the light signal measured for the donor protein.

If the technique is a BRET2 technique, the donor is *Renilla* luciferase [Rluc] or *Renilla* luciferase mutant 8 [Rluc8] (Loening A M, et al, *Protein Eng Des Sel* 2006 September; 19(9):391-400 and Bacart J, et al, *Biotechnol J* 2008 March; 3(3):311-24.) and DeepBlueC™ or coelenterazine 400a as substrate; the acceptor is Green fluorescent protein-2 [GFP2] or green fluorescent protein 10 [GFP10]).

Immediately after the final injections, repeated sequential readings will be taken at a wavelength covering the peak of the specific emission wavelength of the Rluc/coleneterazine 400a (395 nm) and the peak of the specific emission wavelength of the acceptor (510 nm). A BRET signal may be determined as the ratio between the light signal measured for an acceptor protein and the light signal measured for the donor protein.

A BRET signal of a cell obtained in step c) is compared with corresponding absence of a BRET signal of a cell obtained in c) in the absence of a potential modulator compound. Alternatively, a change in a BRET signal of a cell obtained in step c) is compared with a corresponding original BRET signal of a cell obtained in c) in the absence of a potential modulator compound.

Alternatively, the BRET signal obtained in step b) is compared with the background (or absence of a) BRET signal obtained from the cell in the absence of the potential modulator compound. A difference between the BRET signal as obtained in b) and the BRET signal obtained in the absence of the potential modulator compound, is indicative of the potential modulator compound being a compound which modulates a taste receptor. Alternatively, the BRET signal obtained in step b) may compared with a corresponding original BRET signal of a cell obtained in step b) in the absence of a potential modulator compound. A difference between the BRET signal as obtained in b) and the BRET signal obtained in the absence of the potential modulator compound, is indicative of the potential modulator compound being a compound which modulates a taste receptor. Likewise, the BRET signals obtained with two or more different sample solution may be compared whereby the different sample solution may contain different fractions of a food products, extracts of a food product, and/or extracts of biomass as described above.

A compound that increases a BRET signal or that induces a detectable BRET signal is a potential enhancer of a taste. In contrast, a compound that decreases a BRET signal is a potential masker of a taste.

According to a preferred embodiment, a potential enhancer of a taste has been identified when the comparison performed in step c) indicates the presence of a BRET signal or a detectable BRET signal or a detectable increase of a BRET signal of at least 2%. More preferably, a potential enhancer of a taste has been identified when the comparison performed in step c) indicates an increase of at least 4%, of at least 6%, of at least 8%, of at least 10%, of at least 12%, of at least 14%, of at least 16%, of at least 18%, of at least 20%, of at least 22%, of at least 24%, of at least 26%, of at least 28%, of at least 30%, of at least 32%, of at least 34%, of at least 36%, of at least 38%, of at least 40%, of at least 42% or more, of a BRET signal.

According to another preferred embodiment, a potential masker of a taste has been identified when the comparison performed in step c) indicates a decrease of at least 2% of a BRET signal. More preferably, a potential masker of a taste has been identified when the comparison performed in step c) indicates a decrease of at least 4%, of at least 6%, of at least 8%, of at least 10%, of at least 12%, of at least 14%, of at least 16%, of at least 18%, of at least 20%, of at least 22%, of at least 24%, of at least 26%, of at least 28%, of at least 30%, of at least 32%, of at least 34%, of at least 36%, of at least 38%, of at least 40%, of at least 42% or more of a BRET signal.

If a known inhibitor or activator of a taste receptor is present, the increase or decrease respectively of a BRET signal is compared to the BRET signal obtained in the absence of said potential modulator compound.

In a further aspect, there is provided a potential modulator compound of a taste receptor identified by a method as identified herein.

In another aspect, the invention pertains to a method for producing a compound which modulates a taste receptor. The method comprises the steps of identifying the compound which modulates a taste receptor in a method as defined herein, and recovery of the compound. Methods for recovering and/or (partial) purification of compound modulating taste are known to the skilled person per se.

In yet another aspect, the invention pertains to the use of a BRET technique or assay for identification of a compound which modulates a taste receptor. The BRET technique or assay may be used in accordance with the methods of the invention described herein.

General Technical Information

Nucleic Acid Molecule Defined by a SEQ ID NO and Sequence Identity

It is to be understood that each gene or nucleic acid molecule as identified herein by a given Sequence Identity Number (for example SEQ ID NO 1) is not limited to this specific sequence as disclosed. Each gene sequence or nucleotide sequence as identified herein encodes a given protein or polypeptide as identified herein. Throughout this application, each time one refers to a specific nucleotide sequence SEQ ID NO (take SEQ ID NO:1 as example), one may replace it by:

i. a nucleotide sequence comprising a nucleotide sequence that has at least 60% sequence identity with SEQ ID NO:1, ii. a nucleotide sequences the complementary strand of which hybridizes to a nucleic acid molecule of sequence of (i) or (ii);

iii. a nucleotide sequence the sequence of which differs from the sequence of a nucleic acid molecule of (i) due to the degeneracy of the genetic code.

iv. a nucleotide sequence that encodes an amino acid sequence that has at least 60% amino acid identity with an amino acid sequence encoded by a nucleotide sequence SEQ ID NO:1.

Each nucleotide sequence or amino acid sequence described herein by virtue of its identity percentage (at least 60%) with a given nucleotide sequence or amino acid sequence respectively has in a further preferred embodiment an identity of at least 65%, 70%, 75%, 80%, 85%, 90%, 95%, 97%, 98%, 99% or more identity with the given nucleotide or amino acid sequence respectively. In a preferred embodiment, sequence identity is determined by comparing the whole length of the sequences as identified herein.

"Sequence identity" is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Expression of a Taste Receptor in a Cell

A taste receptor and a β-arrestin for use in a method of the present invention can be prepared using recombinant techniques, in which a nucleotide sequence encoding a taste receptor fused to a luciferase protein and another one encoding a β-arrestin fused to a fluorescent protein are expressed in a suitable cell. The present invention thus also concerns the use of a vector comprising said nucleic acid molecule represented by said nucleotide sequence as defined above. Preferably a vector is a replicative vector comprising an origin of replication (or autonomously replication sequence) that ensures multiplication of a vector in a suitable host for the vector. Alternatively a vector is capable of integrating into a cell's genome, e.g. through homologous recombination or otherwise. A particularly preferred vector is an expression vector wherein a nucleotide sequence encoding a polypeptide as defined above, is operably linked to a promoter capable of directing expression of a coding sequence in a cell for the vector.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one skilled in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. An expression vector allows a polypeptide as defined above to be prepared using recombinant techniques in which a nucleotide sequence encoding said polypeptide is expressed in a suitable cell, e.g. cultured cells.

Preferably the expression of each of the nucleic acid sequence of the invention defined above is inducible. The inducibility of the expression of each nucleic acid sequence can be fulfilled by any way known to the skilled person. For example, the Invitrogen T-Rex system (Tetracycline-Regulated Expression, based on the tet operon, expression of the inserted gene is repressed until an inducer is added to the media), the Invitrogen Gene-Switch System (based on activation of the GaW-EIb promoter), the Stratagene Complete Control Inducible mammalian Expression system (based on transcription activation by the insect hormone ecdysone or its analog ponasterone A (ponA) in mammalian cells harboring both the gene for the *Drosophila melanogaster* ecdysone receptor and a promoter containing a binding site for the ecdysone receptor), the New England Biolabs RheoSwitch® Mammalian Inducible Expression System (based on the highly specific interaction of a synthetic inducer, RheoSwitch Ligand RSLI, and a chimeric bipartite nuclear receptor), the Qbiogene Q-mate™ Inducible Expression System, or Q-mate™ CymR system (based on repression of gene expression by the cumate repressor protein CymR bound to operator sites in the absence of the inducer molecule cumate. With cumate present, CymR binds to cumate and undergoes a conformational change resulting in its release from the operator sites.), the Stratagene's LacSwitch® II inducible mammalian expression system (based on the lac operon, expression of the inserted gene is repressed until an inducer is added to the media). Even more preferably, the expression of each nucleic acid sequence is rendered inducible by the presence of an inducible promoter operably linked to each of the nucleic acid subsequence present in the nucleic acid sequence of the invention. In the context of the invention, "operably linked" is defined as a configuration in which a control sequence, here a promoter sequence, is appropriately placed at a position relative to the nucleic acid subsequence such that the control sequence directs the expression of the nucleic acid subsequence.

An inducible promoter may be any promoter or parts thereof functional for a given nucleic acid subsequence as defined above and in a given cell, wherein the transcription initiation activity of the promoter can be induced in a cell upon the addition of a given inducing agent during culture of the cells. More preferably, the inducible promoter is a tetracycline-regulated promoter. Even more preferably, the inducible promoter is a tetracyclin-regulated hybrid human cytomegalovirus promoter as described in Yao et al (Yao, F. et al. (1998) Hum. Gene Therapy 9: 1939-1950 and Yao, F. and Eriksson, E. (1999) Hum. Gene Therapy 10: 419-427). This system can be purchased from Invitrogen as the T-Rex expression system). The use of an inducible expression system may circumvent the toxicity problem described using a stable expression system.

Typically, a nucleic acid encoding a polypeptide as defined above is used in an expression vector. The phrase "expression vector" generally refers to a nucleotide sequence that is capable of effecting expression of a gene in a host compatible with such sequences. These expression vectors typically include at least a suitable promoter sequence and optionally, a transcription termination signal. Additional factors necessary or helpful in effecting expression can also be used as described herein. A nucleic acid or DNA encoding a polypeptide is incorporated into a DNA construct capable of introduction into and expression in an in vitro cell culture. Specifically, a DNA construct is suitable for replication in a prokaryotic host, such as bacteria, e.g., *E. coli*, or can be introduced into a cultured mammalian, plant, insect, e.g., Sf9, yeast, fungi or another eukaryotic cell line.

A DNA construct prepared for introduction into a particular cell typically includes a replication system recognized by the host, the intended DNA segment encoding a desired polypeptide, and transcriptional and translational initiation and termination regulatory sequences operably linked to a polypeptide-encoding segment. A DNA segment is "operably linked" when it is placed into a functional relationship with another DNA segment. For example, a promoter or enhancer is operably linked to a coding sequence if it stimulates the transcription of the sequence. However, an enhancer need not be contiguous with a coding sequence whose transcription it controls. Linking is accomplished by ligation at convenient restriction sites or at adapters or linkers inserted in lieu thereof.

The selection of an appropriate promoter sequence generally depends upon the cell type selected for the expression of a DNA segment. Examples of suitable promoter sequences include prokaryotic and eukaryotic promoters well known in the art (see, e.g. Sambrook and Russell, 2001, supra). A transcriptional regulatory sequence typically includes a heterologous enhancer or promoter that is recognised by the host. The selection of an appropriate promoter depends upon the cell, but promoters such as the trp, lac and phage promoters, tRNA promoters and glycolytic enzyme promoters are known and available (see, e.g. Sambrook and Russell, 2001, supra). An expression vector including the replication system and transcriptional and translational regulatory sequences together with the insertion site for a polypeptide encoding segment can be employed. Examples of workable combinations of cell lines and expression vectors are described in Sambrook and Russell (2001, supra) and in Metzger et al. (1988) Nature 334: 31-36. For example, a suitable expression vector can be expressed in, yeast, e.g. *S. cerevisiae*, e.g., insect cells, e.g., Sf9 cells, mammalian cells, e.g., CHO cells and bacterial cells, e.g., *E. coli*. A cell may thus be a prokaryotic or eukarotic host cell. A cell may be a cell that is suitable for culture in liquid or on solid media. A cell is preferably used in a method of the invention as defined above.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a method as defined herein may comprise additional step(s) than the ones specifically identified, said additional step(s) not altering the unique characteristic of the invention. In addition, reference to an element by the indefinite article "a" or "an" does not exclude the possibility that more than one of the elements is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Example 1

Figure 1:
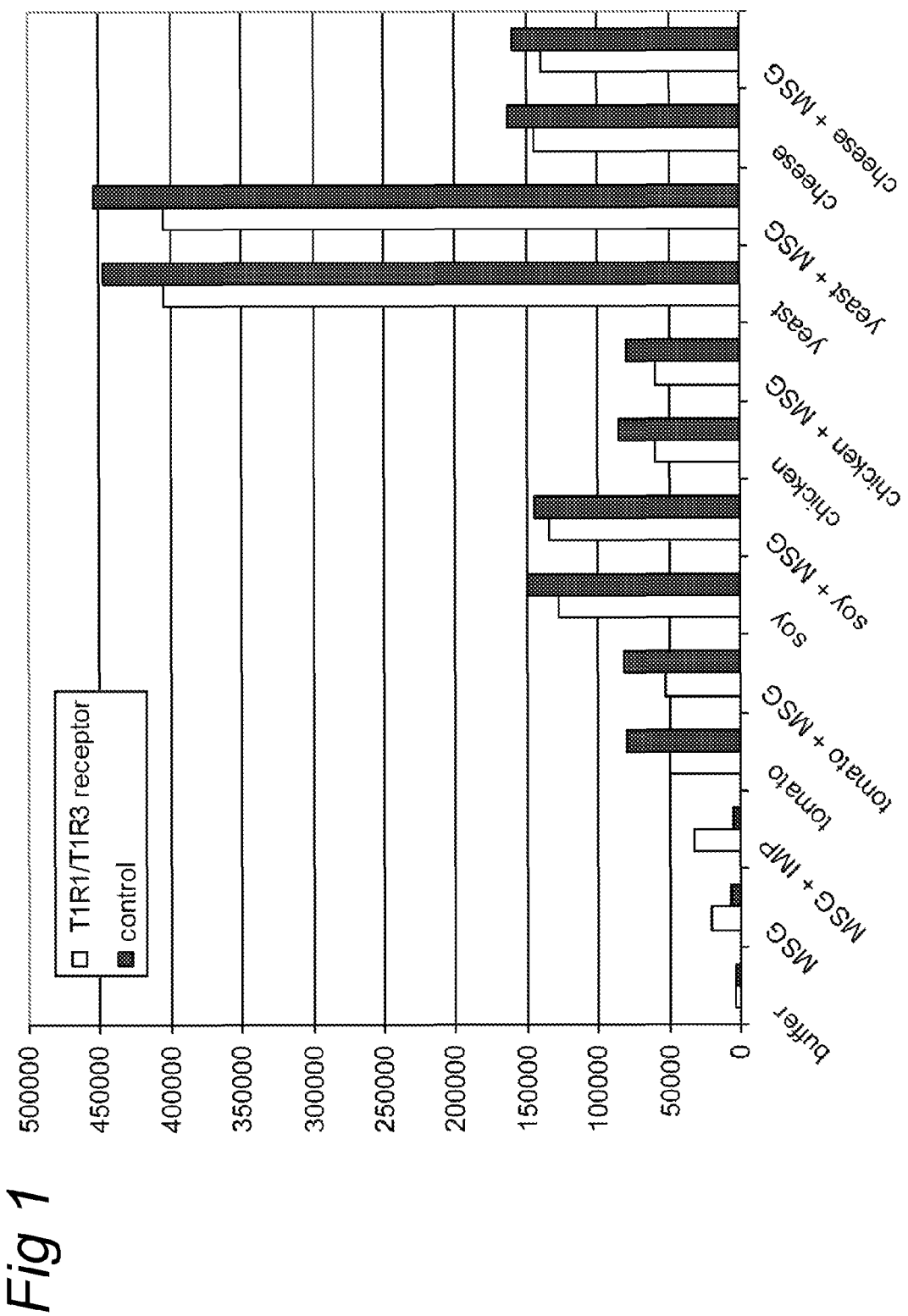
FIG. 1 Activation of the T1R1/T1R3 umami receptor expressed in HEK293-Gα15 cells as measured by monitoring the release of intracellular calcium using the calcium fluorescent marker Fluo-4-AM as described in Example 2. Activity of the umami receptor was measured as the change in fluorescence which was calculated by subtracting the maximum fluorescence after the addition of the test solution from the baseline fluorescence measured before addition of the test solution. Test solutions comprise extracts as indicated and prepared as described in Example 2. MSG=10 mM; MSG+IMP=1 mM MSG+500 µM IMP.
Figure 2A:
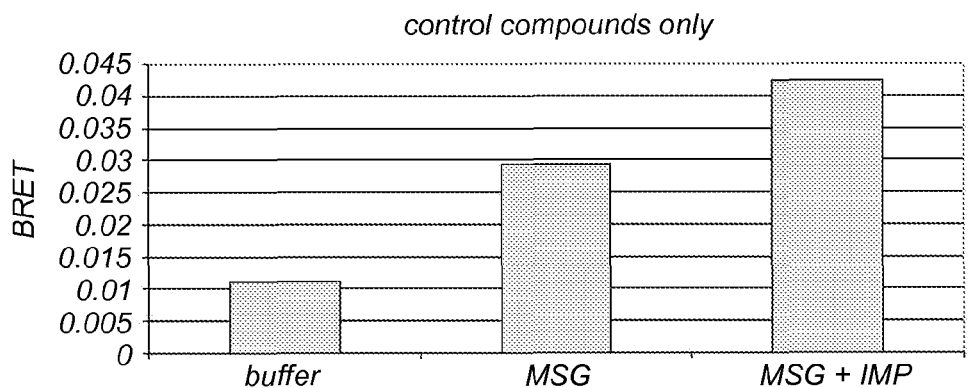
FIG. 2 Activation of the T1R1/T1R3 umami receptor expressed in HEK293-Gα15 cells as measured by BRET assays as described in Example 2. Test solutions (or buffer) as indicated and substrate were added to the cells. The BRET signals were determined as the ratio between readings taken at the acceptor wavelength (515 nm) divided by the signals determined for the donor (400 nm). To correct for background signal due to overlap of donor emission at the acceptor wavelength, the BRET ratio was determined in parallel for cells expressing the donor alone (T1R1/T1R3-Rluc). This BRET background value was subtracted from the BRET value obtained for the cells expressing both BRET partners (BRET=BRET ratio−background ratio). A BRET signal above the values achieved for buffer alone was defined as umami receptor-specific (see also table 2B).
Figure 2B:
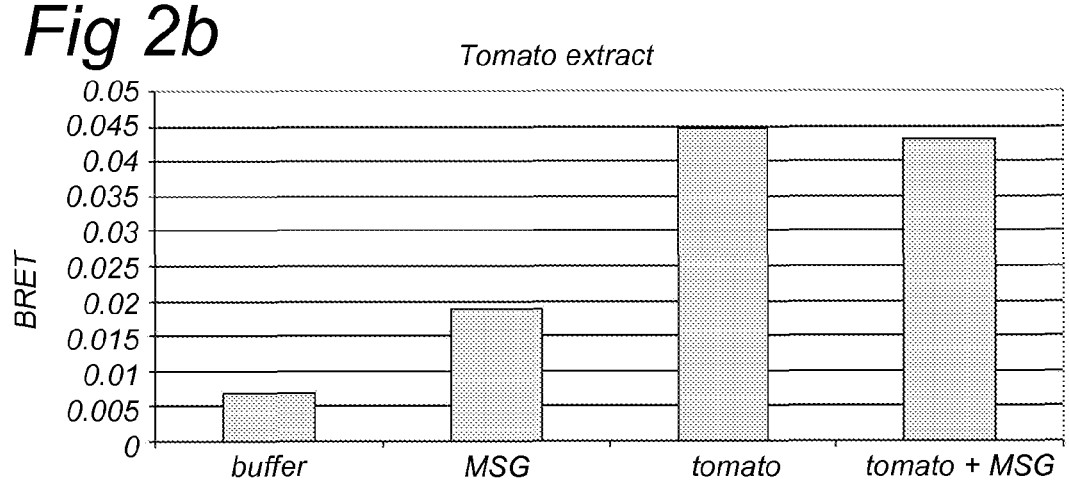
Figure 2C:
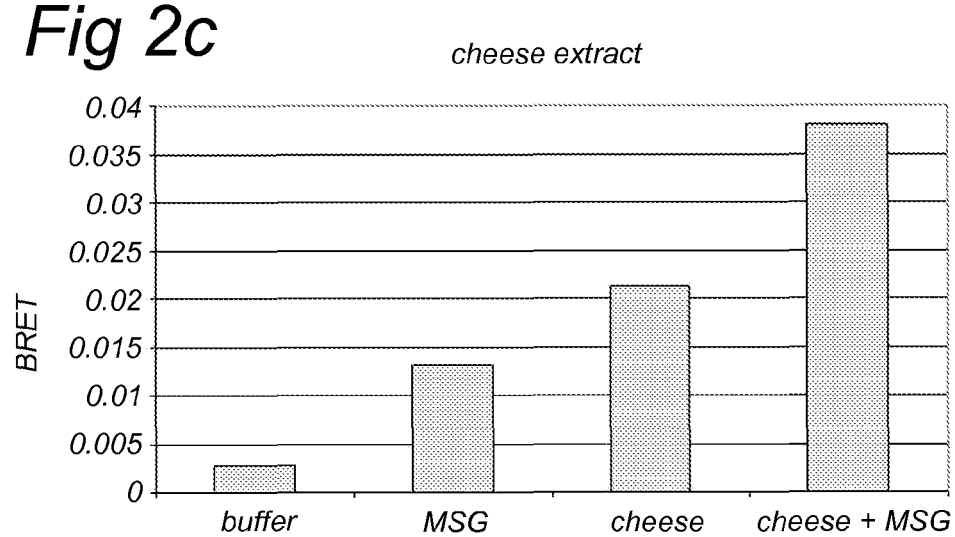
Figure 2D:
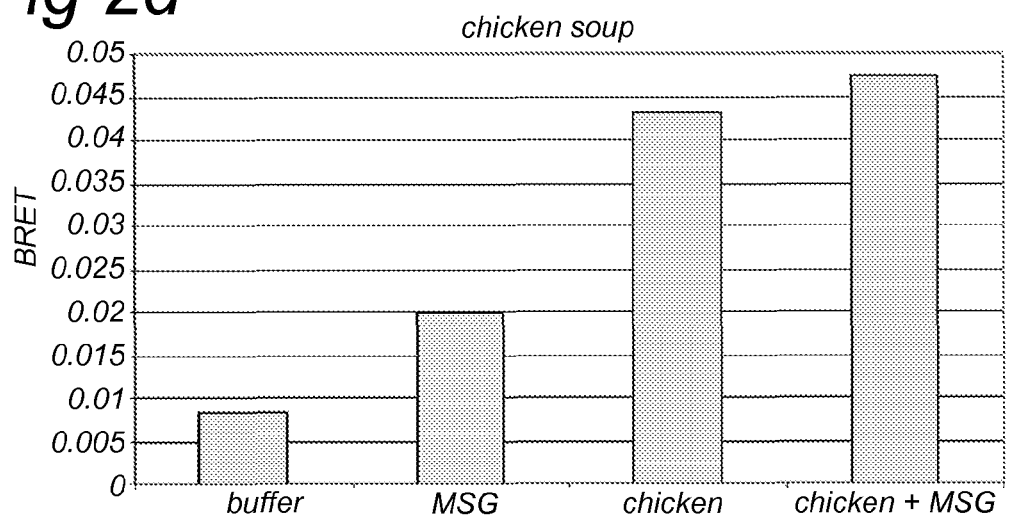
Figure 2E:
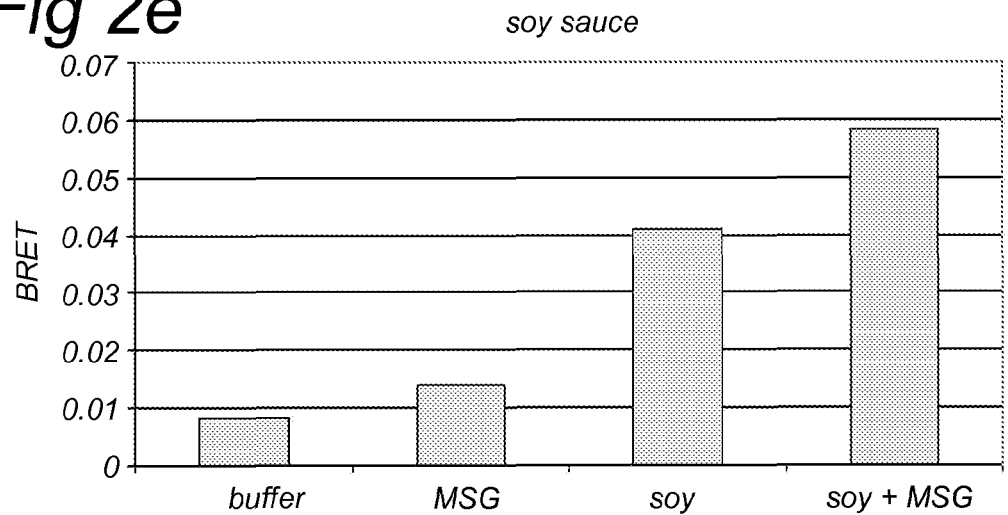
Figure 2F:
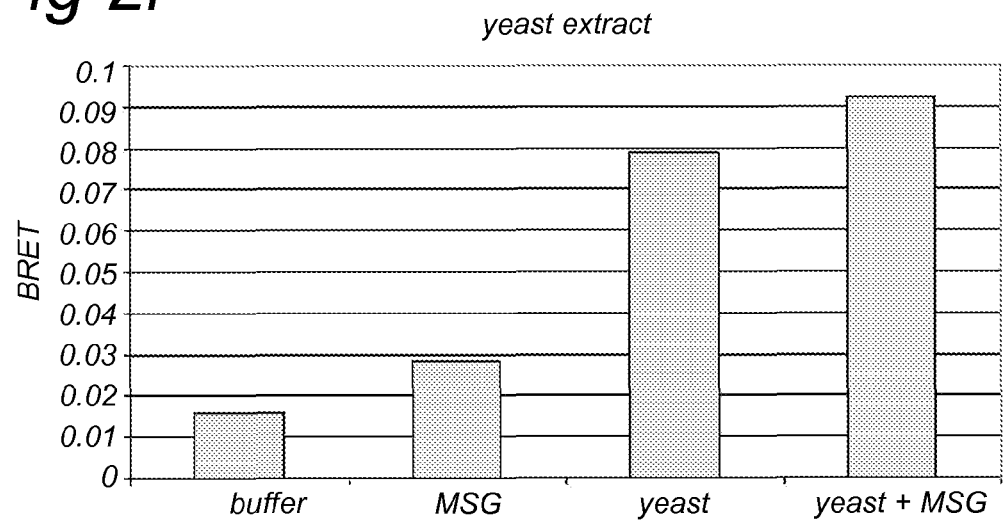

Proof of Principle Using the Human Umami Receptor T1R1/T1R3

We developed a unique functional umami receptor assay to evaluate and quantify umami in tomato and other crude plant or food extracts using the BRET technique: to test the principle we used the donor and acceptor proteins relating to BRET-2. In short, the human T1R1 and T1R3 taste receptors were cloned and fused with *Renilla* luciferase (Rluc) as donor protein; green fluorescent protein-2 (GFP2) served as acceptor protein and was fused to β-arrestin-2. Both constructs were transfected into a HEK293 cell line cells) for heterologous expression of the proteins. Various mammalian cell lines have been reported to be highly suitable for expression of receptors or other proteins, with HEK293 (human embryonic kidney) cells and CHO (Chinese hamster ovary) cells being some of the most versatile and suitable ones[12]. Similarly, GPCRs can be expressed in various ways as described in multiple publications, such as transient[6, 8, 13-15] or stable (constitutive or inducible)[6, 9, 16, 17] expression, depending on the nature of the experiment, the respective receptor or the available time.

Upon receptor stimulation with an agonist or crude extracts, the β-arrestin-2/GFP-2 protein interacts with the activated receptor thus bringing GFP-2 in close proximity with luciferase, making energy transfer between these two proteins possible and generating a BRET signal. In the presence of oxygen the luciferase catalyses the transformation of the substrate DeepBlueC into coelenteramide, which can be measured at 395-410 nm. If GFP-2 is in close proximity to the luciferase and energy transfer takes place, the emission will shift to 510 nm; this is referred to as the BRET signal and is expressed as ratio between the acceptor (GFP-2) and the donor (*Renilla* luciferase).

The following experiments are designed to illustrate that conventional calcium-based functional receptor assays are not suitable for measuring the effects of crude extracts; in contrast, the BRET assay (as indicated here with umami) can clearly measure specific receptor responses using crude natural extracts. Moreover, the assay is also sensitive enough for detecting differences of receptor activation between the different tomato samples.

Materials & Methods:

Chemicals and Media:

Fluo-4 AM was from Molecular Probes (# F-14202, prepared as 5 mM stock in DMSO), DMEM (with 4.5 g/l glucose and ultraglutamine, # BE12-604F) was from Lonza, trypsin-EDTA, Lipofectamine 2000, OptiMem and FCS were obtained from Life Technologies Invitrogen. Monosodium glutamate (MSG), Inosine 5'-monophosphate as well as all other chemicals were from Sigma-Aldrich. The plasmid encoding GFP2-β-arrestin-2 was purchased from BioSignal Packard (#6310176).

Coelenterazine 400A (a DeepBlueC derivative) and Coelenterazine-H were from VWR International (# BTIU10125-1 and 233903-50, respectively).

All other cell culture supplies were from Greiner BioOne.

Receptor Fusion Constructs, Cell Lines, and Media:

The human T1R1 and human T1R3 umami receptors were fused at their C-terminal in frame to *Renilla* Luciferase (Rluc) using standard molecular cloning techniques and the codon-humanized pRluc-N3 vector from PerkinElmer (#6310220). For expression of the umami receptors and the construct encoding GFP-2/β-arrestin-2, HEK293 cells (human embryonic kidney cells, ATCC) were used using traditional transfection methods (see also below).

HEK293 cells were maintained in DMEM and 10% FBS at 37° C./5% $CO_2$.

Tomato Extracts:

The tomato extracts which served as representative natural, complex test material were prepared as follows: Frozen tomato samples (in −80° C.) were weighed and dissolved in an equal amount of water. After the seeds and locular tissues (pulp) were removed and put aside, the tomato pericarp (flesh) was ground using a mortar and pestle. The seeds and pulp were then added back to the mixture ensuring that they are well mixed and the seeds were not crushed. The mixture was centrifuged for 15 minutes at 4000 rpm, the supernatant (serum) removed and freeze-dried in 10 ml aliquots. Before the measurements, an equal volume of water was added to dissolve the sample.

Generation of the T1R1/T1R3 and Rluc Fusion Constructs:

As mentioned above, we have generated the C-terminal Rluc receptor fusion constructs of the human T1R1 and human T1R3 umami receptor using standard molecular cloning techniques. This resulted in 2 different constructs: T1R1-Rluc and T1R3-Rluc. They can be either transfected together, resulting in a functional receptor heterodimer containing two Rluc moieties; alternatively either construct can be transfected in combination with the wild type receptor, thus resulting in T1R1-Rluc combined with T1R3 or T1R1 combined with T1R3-Rluc.

The sequences (cDNA and protein) for the wild type receptors as well as the fusion constructs and the *Renilla* luciferase are given in the sequence listing (SEQ ID NO:5-8).

Transfections:

HEK293 cells will be transiently transfected with the plasmids encoding the T1R1/T1R3 receptors (containing the Rluc-fusion protein) as well the GFP-2-β-arrestin-2 using Lipofectamine 2000 according to the manufacturers' protocol. In short, HEK293 cells will be seeded at a density of $2 \times 10^5$ cells per well (12-wells plate, 1 ml medium/well), aiming at a confluency of about 80-90% the next day. After 24 h the umami receptor constructs (T1R1-Rluc, T1R3-Rluc, or wild type receptors) will be co-transfected with the plasmid encoding GFP-2-β-arrestin-2 using 15 µg of total DNA per well. We will dissolve the DNA in 100 µl of OptiMem and combine it with 100 µl of OptiMem containing 4 µl of lipofectamine 2000. The mixture will then be incubated for 30 minutes at room temperature, added to each well and the cells allowed to grow for 48 hours. BRET measurements will be carried out 48 h-52 h after transfection. Alternatively, the plasmids encoding the umami receptors can be transfected into HEK293 cells stably expressing the GFP-2-β-arrestin-2 using the same protocol as described above.

For the calcium-based receptor assay, HEK293 cells stably expressing Gα15 are transfected with the T1R1 and T1R3 receptors according to the procedure described above, but scaling down the protocol for 96 well plate format (10-fold reduction using a poly-Lysine coated μClear 96-wells plate).

Calcium-Based Receptor Assay:

Activation of the T1R1/T1R3 umami receptor expressed in HEK293-Gα15 cells has been measured by monitoring the release of intracellular calcium. The growth medium was removed and the cells were loaded for 1 hour with 50 μl Tyrode's buffer (140 mM NaCl, 5 mM KCl, 10 mM glucose, 1 mM $CaCl_2$. 2 $H_2O$, 1 mM $MgCl_2$. 6 $H_2O$, 10 mM Na-pyruvate and 50 mM HEPES pH 7.4) containing 2.5 μM of the fluorescent marker of calcium, Fluo-4-AM, supplemented with 0.5 mM probenicide to prevent leakage of Fluo-4 from the cells and 0.5% FCS, followed by a 1-hr incubation at 37° C. The mixture was removed, and 150 μl of Tyrode's buffer containing 0.5 mM probenicide was added. Intracellular calcium levels were monitored using a Flexstation II 384 (Molecular Devices). Fluorescence measurements were carried out at 37° C. at an excitation wavelength of 485 nm and an emission wavelength of 520 nm. 50 μl of compounds or tomato extracts were added to the cells at a pipettor speed of 104 μl per sec after a baseline measurement of 20 s. Activity of the umami receptor was measured as the change in fluorescence (ΔF) which was calculated by subtracting the maximum fluorescence after the addition of the test solution from the baseline fluorescence measured before addition of the test solution.

The data indicated in table 2A show very clearly that using pure umami compounds results in umami receptor-specific responses (control cells not expressing the receptor give no increase); in contrast, using various tomato extracts results in high non-specific responses in the control cells, making it impossible to indentify signals indicating umami.

BRET Assay:

For the BRET assay we will use a Mithras LB 940 plate reader (Berthold Technologies). The protocol we will use is essentially the same as described by Packard BioOne or published protocols[13] with slight modifications: HEK 293 cells will be transfected as described above. 48 h after transfection they will be harvested and taken up in BRET buffer (D-PBS containing 2 μg/ml Aprotinin) at a density of $2\times10^6$ cells/ml. After leaving the cells for 1 hour at room temperature for equilibration, 30 μl containing approximately $1\times10^5$ cells will be transferred to each well of a white 96 well plate. 10 μl of test compounds (or buffer) and 10 μl of the substrate coelenterazine (final concentration 5 μM) will be added simultaneously to the cells using the injectors. Immediately after the final injections, sequential readings will be taken at 410 nm and 515 nm. The BRET signals will be determined as the ratio between GFP-2 emission (515 nm) and Rluc/coelenterazine emission (410 nm).

Example 2

Detection of Taste Modulators in Complex Samples

Preparation and Selection of Test Samples (Extracts)

The extracts or crude mixtures described below are examples for natural samples unsuitable for testing with a calcium-based receptor assay due to their high non-specific background signal. They are from different origin and are selected to illustrate a wide range of potential test samples. The selected samples are also known to contain glutamate, ribotides or both and are therefore good candidates to examine in a BRET assay using the umami receptor T1R1/T1R3 as example.

Tomato: The preparation of tomato extract is already been described in Example 1
  Yeast extract: Commercially available yeast extract enriched for 5'-ribotides (DSM, Maxarome Select yeast extract). The yeast extract was dissolved in water (10× weight of yeast extract).
  Soy sauce: commercially available soy sauce was used (Conimex ketjap manis).
  Chicken bouillon: A commercially available chicken bouillon cube (Knorr) was dissolved in hot water as indicated by the manufacturers. To remove particles from the test sample the bouillon was centrifuged at 5000 rpm for 10 minutes and the supernatant transferred to a fresh tube.
  Cheese extract: commercially available Roquefort cheese was weighed and dissolved in an equal amount of water and homogenized using a mortar and pestle. The mixture was centrifuged for 10 minutes at 5000 rpm to remove particles and the supernatant transferred to a fresh tube.

Experimental Procedures

Transfections:

HEK293 cells were transiently transfected with the plasmids encoding the T1R1 and T1R3 receptors (the T1R3 receptor contained the Rluc-fusion protein in this experiment) as well the GFP-2-β-arrestin-2 using Lipofectamine 2000 according to the manufacturers' protocol. In short, HEK293 cells will be seeded at a density of $2\times10^5$ cells per well (12-wells plate, 1 ml medium/well), aiming at a confluency of about 80-90% the next day. After 24 h the umami receptor constructs (T1R1 and T1R3-Rluc receptors) were co-transfected with the plasmid encoding GFP-2-β-arrestin-2 using 15 μg of total DNA per well. The DNA was dissolved in 100 μl of OptiMem and combined with 100 μl of OptiMem containing 4 μl of lipofectamine 2000. The mixture was incubated for 30 minutes at room temperature, added to each well and the cells allowed to grow for 48 hours. BRET measurements were carried out 48 h-52 h after transfection.

Alternatively, the plasmids encoding the umami receptors were transfected into HEK293 cells stably expressing the GFP-2-β-arrestin-2 using the same protocol as described above.

For the calcium-based receptor assay, HEK293 cells stably expressing Gα15 are transfected with the T1R1 and T1R3 receptors according to the procedure described above, but scaling down the protocol for 96 well plate format (10-fold reduction using a poly-Lysine coated pClear 96-wells plate).

Calcium-Based Receptor Assay:

Activation of the T1R1/T1R3 umami receptor expressed in HEK293-Gα15 cells has been measured by monitoring the release of intracellular calcium. The growth medium was removed and the cells were loaded for 1 hour with 50 μl Tyrode's buffer (140 mM NaCl, 5 mM KCl, 10 mM glucose, 1 mM $CaCl_2$. 2 $H_2O$, 1 mM $MgCl_2$. 6 $H_2O$, 10 mM Na-pyruvate and 50 mM HEPES pH 7.4) containing 2.5 μM of the fluorescent marker of calcium, Fluo-4-AM, supplemented with 0.5 mM probenicide to prevent leakage of Fluo-4 from the cells and 0.5% FCS, followed by a 1-hr incubation at 37° C. The mixture was removed, and 150 μl of Tyrode's buffer containing 0.5 mM probenicide was added. Intracellular calcium levels were monitored using a Flexstation II 384 (Molecular Devices). Fluorescence measurements were carried out at 37° C. at an excitation wavelength of 485 nm and an emission wavelength of 520 nm. 50 µl of compounds or extracts were added to the cells at a pipettor speed of 104 µl per sec after a baseline measurement of 20 s. Activity of the umami receptor was measured as the change in fluorescence (ΔF) which was calculated by subtracting the maximum fluorescence after the addition of the test solution from the baseline fluorescence measured before addition of the test solution.

Table 2B and FIG. 1 illustrate that using pure umami compounds (MSG and MSG+IMP) results in umami receptor-specific responses; in contrast, using various extracts and natural mixtures results in high non-specific responses in control cells not expressing the umami receptor as well, thereby making it impossible to calculate receptor-specific signals indicating umami.

BRET Assay:

For the BRET assay we used a Mithras LB 940 plate reader (Berthold Technologies). The assay protocol is essentially the same as described by Packard BioOne or other published protocols[10, 13] with slight modifications: HEK 293 cells were transfected as described above. 40 h after transfection they were harvested and taken up in BRET buffer (D-PBS containing 1 g/l D-glucose and 2 µg/ml Aprotinin) at a density of $2 \times 10^6$ cells/ml. After leaving the cells for 1 hour at room temperature for equilibration, 30 µl containing $1 \times 10^5$ cells were transferred to each well of a white 96 well plate. 10 µl of test compounds (or buffer) and 10 µl of the substrate coelenterazine 400 (DeepBlueC, final concentration 5 µM) were added to the cells using the injectors. Immediately after the final injections, sequential readings were taken at 400 nm and 515 nm. Alternatively, compounds were added to the cells manually and were incubated for 5 minutes before injection of the substrate. The BRET signals were determined as the ratio between readings taken at the acceptor wavelength (GFP-2; 515 nm) divided by the signals determined for the donor (Rluc/coelenterazine 400; 400 nm). To correct for background signal due to overlap of donor emission at the acceptor wavelength, the BRET ratio was determined in parallel for cells expressing the donor alone (T1R1/T1R3-Rluc). This BRET background value was subtracted from the BRET value obtained for the cells expressing both BRET partners (BRET=BRET ratio−background ratio). A BRET signal above the values achieved for buffer alone was defined as umami receptor-specific (see table 2B).

Results:

As indicated in table 2B and FIG. 1, it was not possible to achieve umami receptor-specific signals using representative extracts and other complex mixtures using the calcium-based receptor assay. In contrast, FIG. 2 shows that using the described BRET assay it was possible to specifically measure umami receptor activation for these complex samples.

The definition of receptor-specific signals differs slightly for technical reasons: For the calcium assay, cells expressing the umami receptor and Gα15 are compared with cells expressing Gα15 only; the difference between these signals is defined as umami receptor-specific signal. For the BRET assay the background is determined using cells expressing the donor only (T1R1/T1R3-Rluc); a positive value indicates a specific BRET signal.

TABLE 1 non-exhaustive list of agonist of several taste receptors as identified

| Receptor | agonist |
| --- | --- |
| T1R1/T1R3 | MSG, (L-glutamate), positive allosteric modulator: IMP (inosine monophosphate) |
| mGluR4 | MSG, L-AP4 (L-(+)-2-Amino-4-phosphonobutyric acid) |
| T1R2/T1R3 | Sweeteners (natural and artificial): Glucose, sucrose, saccharose |
| GPR120 | Medium and long-chain fatty acids (linoleic acid) |
| GPR93 | LPA (lysophosphatidic acid), proteolytic degradation products |
| FFAR1 | Medium and long-chain fatty acids (eicosatrienoic acid, linoleic acid) |
| FFAR2 | Short chain fatty acids (acetate, propionate) |
| FFAR3 | Short chain fatty acids (acetate, propionate) |
| GPRC6A | L-amino acids (most potent L-arginine) |
| GPR84 | Medium chain fatty acids (Capric acid, Undecanoic acid) |
| TAS2R7 | Quinacrine, chloroquine, papaverine, strychnine |
| TAS2R14 | Picrotoxin, picrotoxinin, α-thujone, naphthoic acid (8 in total) |
| TAS2R161 | β-glucopyranosides (e.g. salicin, phenyl-β-D-glucopyranoside) |
| TAS2R381 | Phenylthiocarbamide, PROP, acetylthiourea and others |
| TAS2R43 | Saccharin, acesulfame K, aristolochic acid 6-Nitrosaccharin |
| TAS2R44 | Saccharin, acesulfame K, aristolochic acid |
| TAS2R461 | Sesquiterpenes Absinthine, denatonium benzoate |
| TAS2R47 | 6-nitrosaccharin and saccharin |
| TAS2R4 | Quinine, denatonium benzoate |
| TAS2R8 | Ranitidine, denatonium benzoate |
| TAS2R10 | Strychnine, brucine, denatonium benzoate, absinthine |
| TAS2R39 | Acetaminophen, ranitidine, denatonium benzoate |
| TAS2R45 | Absinthine |
| TAS2R48 | Absinthine |
| T2R1/TAS2R1 | chloroquine, dexamethasone, quinine |
| T2R3/TAS2R3 | chloroquine, 2-acetylpyrazine |
| T2R4/TAS2R4 | quinine, denatonium benzoate |
| T2R5/TAS2R5 | dimethylbiguanide, oleuropein |
| T2R7/TAS2R7 | quinacrine, chloroquine, papaverine, strychnine |
| T2R8/TAS2R8 | ranitidine, denatonium benzoate |
| T2R9/TAS2R9 | ranitidine, ofloxacin |
| T2R10/TAS2R10 | strychnine, brucine, denatonium benzoate, absinthine |
| T2R13/TAS2R13 | ethylpyrazine, quinacrine |
| T2R14/TAS2R14 | picrotoxin, picrotoxinin, α-thujone, naphthoic acid |
| T2R16/TAS2R16 | β-glucopyranosides (e.g. salicin, phenyl-β-D-glucopyranoside) |
| T2R24/TAS2R42 | Not known |
| T2R44/TAS2R47 | 6-nitrosaccharin and saccharin |
| T2R50/TAS2R45 | absinthine |
| T2R51/TAS2R38 | phenylthiocarbamide, PROP, acetylthiourea |
| T2R54/TAS2R39 | acetaminophen, ranitidine, denatonium benzoate |
| T2R55/TAS2R40 | linamarin, oxybutynin chloride |
| T2R61/TAS2R43 | saccharin, acesulfame K, aristolochic acid 6-Nitrosaccharin |
| T2R63/TAS2R49 | Not known |
| T2R64/TAS2R44 | saccharin, acesulfame K, aristolochic acid |
| T2R65/TAS2R48 | Absinthine, ethylpyrazine |
| T2R67/TAS2R50 | ethylpyrazine, oxybutynin chloride |
| T2R71/TAS2R41 | Nitrosaccharin |
| T2R75/TAS2R46 | sesquiterpenes absinthine, denatonium benzoate |
| T2R76 | brucine |

TABLE 2A

Specific activation of a T1R1/T1R3 umami receptor measured by the release of intracellular calcium: average values are shown

| | T1R1/T1R3 umami receptor | | | Control cells (no T1R1/T1R3) | | |
|---|---|---|---|---|---|---|
| Compounds | meas. 1 | meas. 2 | average | meas. 1 | meas. 2 | average |
| 100 µM MSG | 1146 | 1193 | 1170 | 1102 | 1168 | 1135 |
| 1 mM MSG | 2548 | 3990 | 3269 | 1100 | 1020 | 1060 |
| 10 mM MSG | 5766 | 7732 | 6749 | 1200 | 1030 | 1115 |
| extract 1 | 4649 | 7985 | 6317 | 6420 | 3449 | 4934 |
| extract 2 | 4552 | 6461 | 5506 | 7435 | 6061 | 6748 |
| extract 3 | 5980 | 5080 | 5530 | 4369 | 5431 | 4900 |
| extract 4 | 5394 | 4285 | 4839 | 5848 | 5784 | 5816 |
| extract 5 | 6338 | 9179 | 7759 | 6423 | 6318 | 6370 |
| extract 6 | 9285 | 10503 | 9894 | 10708 | 9785 | 10247 |

TABLE 2B

T1R1/T1R3 receptor-specific signals using the calcium or BRET assay

| Test samples | Calcium assay | BRET assay |
|---|---|---|
| MSG 10 mM | + | + |
| MSG 1 mM + IMP 500 µM | + | + |
| Tomato extract | − | + |
| Yeast extract | − | + |
| Chicken bouillon | − | + |
| Soy sauce | − | + |
| Cheese extract | − | + |

TABLE 3

SEQ ID NO of the DNA/amino acid sequences of taste receptors identified in the sequence listing

| Taste receptor subunit | SEQ ID NO of human DNA sequence | SEQ ID NO of human amino acid sequence |
|---|---|---|
| T1R1 | 1 | 2 |
| T1R3 | 3 | 4 |
| T1R2 | 9 | 10 |
| mGluR4a | 11 | 12 |
| GPR120 | 13 | 14 |
| GPR93 | 15 | 16 |
| FFA receptor 1 | 17 | 18 |
| FFA receptor 2 | 19 | 20 |
| FFA receptor 3 | 21 | 22 |
| GPR84 | 23 | 24 |
| mGluR4c | 25 | 26 |
| T2R1 (=TAS2R1) | 27 | 28 |
| T2R3 (=TAS2R3) | 29 | 30 |
| T2R4 (=TAS2R4) | 31 | 32 |
| T2R5 (=TAS2R5) | 33 | 34 |
| T2R7 (=TAS2R7) | 35 | 36 |
| T2R8 (=TAS2R8) | 37 | 38 |
| T2R9 (=TAS2R9) | 39 | 40 |
| T2R10 (=TAS2R10) | 41 | 42 |
| T2R13 (=TAS2R13) | 43 | 44 |
| T2R14 (=TAS2R14) | 45 | 46 |
| T2R16 (=TAS2R16) | 47 | 48 |
| T2R24 (=TAS2R42) | 49 | 50 |
| T2R44 (=TAS2R47) | 51 | 52 |
| T2R50 (=TAS2R45) | 53 | 54 |
| T2R51 (=TAS2R38 = T2R61) | 55 | 56 |
| T2R54 (=TAS2R39 = T2R57) | 57 | 58 |
| T2R55 (=TAS2R40 = T2R58) | 59 | 60 |
| T2R61 (=TAS2R43 = T2R52) | 61 | 62 |
| T2R63 (TAS2R49 = T2R56) | 63 | 64 |
| T2R64 (=TAS2R44 = T2R53) | 65 | 66 |
| T2R65 (=TAS2R48 = T2R55) | 67 | 68 |
| T2R67 (=TAS2R50 = T2R51) | 69 | 70 |
| T2R71 (=TAS2R41 = T2R59) | 71 | 72 |
| T2R75 (=TAS2R46 = T2R54) | 73 | 74 |
| T2R76 (=TAS2R60 = T2R56) | 75 | 76 |

REFERENCES (1) Scott T R, Verhagen J V. Taste as a factor in the management of nutrition. *Nutrition* 2000 October; 16(10):874-85.

(2) Zhao G Q, Zhang Y F, Hoon M A, Chandrashekar J, Erlenbach I, Ryba N J P, Zuker C S. The receptors for mammalian sweet and umami taste. *Cell* 2003 Oct. 31; 115(3):255-66.

(3) Chandrashekar J, Hoon M A, Ryba N J, Zuker C S. The receptors and cells for mammalian taste. *Nature* 2006 Nov. 16; 444(7117):288-94.

(4) Breslin P A, Spector A C. Mammalian taste perception. *Curr Biol* 2008 Feb. 26; 18(4):R148-R155.

(5) Kinnamon S C, Vandenbeuch A. Receptors and transduction of umami taste stimuli. *Ann N Y Acad Sci* 2009 July; 1170:55-9.

(6) Zhang F, Klebansky B, Fine R M, Xu H, Pronin A, Liu H, Tachdjian C, Li X. Molecular mechanism for the umami taste synergism. *Proc Natl Acad Sci USA* 2008 Dec. 30; 105(52):20930-4.

(7) Shigemura N, Shirosaki S, Sanematsu K, Yoshida R, Ninomiya Y. Genetic and molecular basis of individual differences in human umami taste perception. *PLoS One* 2009; 4(8):e6717.

(8) Li X, Staszewski L, Xu H, Durick K, Zoller M, Adler E. Human receptors for sweet and umami taste 1. *Proc Natl Acad Sci USA* 2002 Apr. 2; 99(7):4692-6.

(9) Ozeck M, Brust P, Xu H, Servant G. Receptors for bitter, sweet and umami taste couple to inhibitory G protein signaling pathways. *European Journal of Pharmacology* 2004 Apr. 12; 489(3):139-49.

(10) Bacart J, Corbel C, Jockers R, Bach S, Couturier C. The BRET technology and its application to screening assays. *Biotechnol J* 2008 March; 3(3):311-24.

(11) Pfleger K D, Dalrymple M B, Dromey J R, Eidne K A. Monitoring interactions between G-protein-coupled receptors and beta-arrestins. *Biochem Soc Trans* 2007 August; 35(Pt 4):764-6.

(12) Eglen R M, Gilchrist A, Reisine T. The use of immortalized cell lines in GPCR screening: the good, bad and ugly. *Comb Chem High Throughput Screen* 2008 August; 11(7): 560-5.

(13) Vrecl M, Jorgensen R, Pogacnik A, Heding A. Development of a BRET2 screening assay using beta-arrestin 2 mutants. *J Biomol Screen* 2004 June; 9(4):322-33.

(14) Nelson G, Hoon M A, Chandrashekar J, Zhang Y, Ryba N J, Zuker C S. Mammalian sweet taste receptors. *Cell* 2001 Aug. 10; 106(3):381-90.

(15) Jiang P, Cui M, Zhao B, Snyder L A, Benard L M, Osman R, Max M, Margolskee R F. Identification of the cyclamate interaction site within the transmembrane domain of the human sweet taste receptor subunit T1R3. *J Biol Chem* 2005 Oct. 7; 280(40):34296-305.

(16) Stoddart L A, Smith N J, Jenkins L, Brown A J, Milligan G. Conserved polar residues in transmembrane domains V, VI, and VII of free fatty acid receptor 2 and free fatty acid receptor 3 are required for the binding and function of short chain fatty acids. *J Biol Chem* 2008 Nov. 21; 283(47): 32913-24.

(17) Xu H, Staszewski L, Tang H X, Adler E, Zoller M, Li X D. Different functional roles of T1R subunits in the heterorneric taste receptors. *Proceedings of the National Academy of Sciences of the United States of America* 2004 Sep. 28; 101(39):14258-63.

The invention claimed is:

1. A method for identifying a compound which modulates a taste receptor, wherein the method comprises the steps of:
   a) providing a cell expressing (i) a taste receptor fused to a luminescent protein and (ii) a fluorescent protein fused to a β-arrestin, wherein said taste receptor is functional such that a detectable BRET signal is present when a substance known to activate this taste receptor is added to said cell, and wherein the BRET signal is exclusively caused by specific activation of the taste receptor;
   b) contacting the cell with a complex sample solution comprising a potential modulator compound and determining the BRET signal;
   c) comparing the BRET signal obtained in step b) with a BRET signal obtained from the cell in the absence of the potential modulator compound, wherein a difference between the BRET signal as obtained in b) and the BRET signal obtained in the absence of the potential modulator compound, is indicative of said complex sample solution comprising a compound which modulates a taste receptor;
wherein said taste receptor is a G Protein Coupled Receptor, wherein said complex sample solution an aqueous solution, and wherein said aqueous sample solution is a complex sample solution defined as comprising more than 10 chemically different organic molecules, and wherein the complex sample solution comprises at least one of
   (a) a food product;
   (b) an extract of a food product; and
   (c) an extract of edible biomass; and
wherein the BRET signals are obtained in a BRET1 or BRET2 technique.

2. A method according to claim 1, wherein the extract is a tomato extract.

3. A method according to claim 1, wherein a taste receptor is selected from the group consisting of an MSG or umami receptor, a sweet receptor, a bitter receptor, a fat receptor and a nutrient/fatty acid sensing gut receptor.

4. A method according to claim 3, wherein
   (a) the taste receptor is a T1R1, T1R3 heterodimer, wherein at least one of the subunits T1R1 and T1R3 is fused to a luminescent protein, and wherein a fluorescent protein is fused to a β-arrestin; or,
   (b) the taste receptor is a T1R1, T1R3 heterodimer, wherein at least one of the subunits T1R1 and T1R3 is fused to a fluorescent protein, and wherein a luminescent protein is fused to a β-arrestin.

5. A method according to claim 1, wherein at least one of:
   (a) the luminescent protein is a luciferase;
   (b) the fluorescent protein is a GFP; and,
   (e) the β-arrestin is a non-visual β-arrestin.

6. A method according to claim 5, wherein at least one of:
   (a) the luciferase is a *Renilla* luciferase; and,
   (b) the non-visual β-arrestin is a β-arrestin 2.

7. A method according to claim 1, the method comprising the further step of recovering the compound.

* * * * *

SEQUENCE LISTING

```
<160> NUMBER OF SEQ ID NOS: 80

<210> SEQ ID NO 1
<211> LENGTH: 2526
<212> TYPE: DNA
<213> ORGANISM: homo sapiens

<400> SEQUENCE: 1
atgctgctct gcacggctcg cctggtcggc ctgcagcttc tcatttcctg ctgctgggcc      60
tttgcctgcc atagcacgga gtcttctcct gacttcaccc tccccggaga ttacctcctg     120
gcaggcctgt tccctctcca ttctggctgt ctgcaggtga ggcacagacc cgaggtgacc     180
ctgtgtgaca ggtcttgtag cttcaatgag catggctacc acctcttcca ggctatgcgg     240
cttggggttg aggagataaa caactccacg gccctgctgc caacatcac cctggggtac     300 cagctgtatg atgtgtgttc tgactctgcc aatgtgtatg ccacgctgag agtgctctcc     360
ctgccagggc aacaccacat agagctccaa ggagaccttc tccactattc ccctacggtg     420
ctggcagtga ttgggcctga cagcaccaac cgtgctgcca ccacagccgc cctgctgagc     480
cctttcctgg tgcccatgat tagctatgcg gccagcagcg agacgctcag cgtgaagcgg     540 cagtatcct ctttcctgcg caccatcccc aatgacaagt accaggtgga gaccatggtg     600
ctgctgctgc agaagttcgg gtggacctgg atctctctgg ttggcagcag tgacgactat     660
gggcagctag gggtgcaggc actggagaac caggccactg gtcaggggat ctgcattgct     720
ttcaaggaca tcatgccctt ctctgcccag gtgggcgatg agaggatgca gtgcctcatg     780
cgccacctgg cccaggccgg ggccaccgtc gtggttgttt tttccagccg gcagttggcc     840
agggtgtttt tcgagtccgt ggtgctgacc aacctgactg gcaaggtgtg ggtcgcctca     900
gaagcctggg ccctctccag gcacatcact ggggtgcccg ggatccagcg cattgggatg     960
gtgctgggcg tggccatcca agaggggct gtccctggcc tgaaggcgtt tgaagaagcc    1020
tatgcccggg cagacaagaa ggcccctagg ccttgccaca agggctcctg gtgcagcagc    1080
aatcagctct gcagagaatg ccaagctttc atggcacaca cgatgcccaa gctcaaagcc    1140
ttctccatga gttctgccta caacgcatac cgggctgtgt atgcggtggc ccatggcctc    1200
caccagctcc tgggctgtgc ctctggagct tgttccaggg gccgagtcta ccctggcag    1260 cttttggagc agatccacaa ggtgcatttc cttctacaca aggacactgt ggcgtttaat    1320
gacaacagag atcccctcag tagctataac ataattgcct gggactggaa tggacccaag    1380
tggaccttca cggtcctcgg ttcctccaca tggtctccag ttcagctaaa cataaatgag    1440
accaaaatcc agtggcacgg aaaggacaac caggtgccta gtctgtgtg ttccagcgac    1500 tgtcttgaag gcaccagcg agtggttacg ggtttccatc actgctgctt tgagtgtgtg    1560
ccctgtgggg ctgggacctt cctcaacaag agtgacctct acagatgcca gccttgtggg    1620
aaagaagagt gggcacctga gggaagccag acctgcttcc cgcgcactgt ggtgttttg    1680 gctttgcgtg agcacacctc ttgggtgctg ctggcagcta acacgctgct gctgctgctg    1740
ctgcttggga ctgctggcct gttgcctggg cacctagaca cccctgtggt gaggtcagca    1800
gggggccgcc tgtgctttct tatgctgggc tccctggcag caggtagtgg cagcctctat    1860
```

```
ggcttctttg gggaacccac aaggcctgcg tgcttgctac gccaggccct ctttgccctt    1920
ggtttcacca tcttcctgtc ctgcctgaca gttcgctcat tccaactaat catcatcttc    1980
aagttttcca ccaaggtacc tacattctac cacgcctggg tccaaaacca cggtgctggc    2040
ctgtttgtga tgatcagctc agcggcccag ctgcttatct gtctaacttg gctggtggtg    2100
tggaccccac tgcctgctag ggaataccag cgcttccccc atctggtgat gcttgagtgc    2160
acagagacca actccctggg cttcatactg gccttcctct acaatggcct cctctccatc    2220
agtgcctttg cctgcagcta cctgggtaag gacttgccag agaactacaa cgaggccaaa    2280
tgtgtcacct tcagcctgct cttcaacttc gtgtcctgga tcgccttctt caccacggcc    2340
agcgtctacg acggcaagta cctgcctgcg ccaacatga tggctgggct gagcagcctg    2400
agcagcggct tcggtgggta ttttctgcct aagtgctacg tgatcctctg ccgcccagac    2460
ctcaacagca cagagcactt ccaggcctcc attcaggact cacgaggcg ctgcggctcc     2520 acctaa                                                                2526

<210> SEQ ID NO 2
<211> LENGTH: 841
<212> TYPE: PRT
<213> ORGANISM: homo sapiens

<400> SEQUENCE: 2

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Leu Gln Lys Phe Gly Trp
        195                 200                 205

Thr Trp Ile Ser Leu Val Gly Ser Ser Asp Asp Tyr Gly Gln Leu Gly
    210                 215                 220

Val Gln Ala Leu Glu Asn Gln Ala Thr Gly Gln Gly Ile Cys Ile Ala
225                 230                 235                 240

Phe Lys Asp Ile Met Pro Phe Ser Ala Gln Val Gly Asp Glu Arg Met
```

```
              245                 250                 255
Gln Cys Leu Met Arg His Leu Ala Gln Ala Gly Ala Thr Val Val Val
            260                 265                 270

Val Phe Ser Ser Arg Gln Leu Ala Arg Val Phe Phe Glu Ser Val Val
        275                 280                 285

Leu Thr Asn Leu Thr Gly Lys Val Trp Val Ala Ser Glu Ala Trp Ala
    290                 295                 300

Leu Ser Arg His Ile Thr Gly Val Pro Gly Ile Gln Arg Ile Gly Met
305                 310                 315                 320

Val Leu Gly Val Ala Ile Gln Lys Arg Ala Val Pro Gly Leu Lys Ala
                325                 330                 335

Phe Glu Glu Ala Tyr Ala Arg Ala Asp Lys Lys Ala Pro Arg Pro Cys
            340                 345                 350

His Lys Gly Ser Trp Cys Ser Ser Asn Gln Leu Cys Arg Glu Cys Gln
        355                 360                 365

Ala Phe Met Ala His Thr Met Pro Lys Leu Lys Ala Phe Ser Met Ser
    370                 375                 380

Ser Ala Tyr Asn Ala Tyr Arg Ala Val Tyr Ala Val Ala His Gly Leu
385                 390                 395                 400

His Gln Leu Leu Gly Cys Ala Ser Gly Ala Cys Ser Arg Gly Arg Val
                405                 410                 415

Tyr Pro Trp Gln Leu Leu Glu Gln Ile His Lys Val His Phe Leu Leu
            420                 425                 430

His Lys Asp Thr Val Ala Phe Asn Asp Asn Arg Asp Pro Leu Ser Ser
        435                 440                 445

Tyr Asn Ile Ile Ala Trp Asp Trp Asn Gly Pro Lys Trp Thr Phe Thr
    450                 455                 460

Val Leu Gly Ser Ser Thr Trp Ser Pro Val Gln Leu Asn Ile Asn Glu
465                 470                 475                 480

Thr Lys Ile Gln Trp His Gly Lys Asp Asn Gln Val Pro Lys Ser Val
                485                 490                 495

Cys Ser Ser Asp Cys Leu Glu Gly His Gln Arg Val Val Thr Gly Phe
            500                 505                 510

His His Cys Cys Phe Glu Cys Val Pro Cys Gly Ala Gly Thr Phe Leu
        515                 520                 525

Asn Lys Ser Asp Leu Tyr Arg Cys Gln Pro Cys Gly Lys Glu Glu Trp
    530                 535                 540

Ala Pro Glu Gly Ser Gln Thr Cys Phe Pro Arg Thr Val Val Phe Leu
545                 550                 555                 560

Ala Leu Arg Glu His Thr Ser Trp Val Leu Leu Ala Ala Asn Thr Leu
                565                 570                 575

Leu Leu Leu Leu Leu Leu Gly Thr Ala Gly Leu Phe Ala Trp His Leu
            580                 585                 590

Asp Thr Pro Val Val Arg Ser Ala Gly Gly Arg Leu Cys Phe Leu Met
        595                 600                 605

Leu Gly Ser Leu Ala Ala Gly Ser Gly Ser Leu Tyr Gly Phe Phe Gly
    610                 615                 620

Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
                645                 650                 655

Ile Ile Ile Phe Lys Phe Ser Thr Lys Val Pro Thr Phe Tyr His Ala
            660                 665                 670
```

```
Trp Val Gln Asn His Gly Ala Gly Leu Phe Val Met Ile Ser Ser Ala
            675                 680                 685
Ala Gln Leu Leu Ile Cys Leu Thr Trp Leu Val Val Trp Thr Pro Leu
        690                 695                 700
Pro Ala Arg Glu Tyr Gln Arg Phe Pro His Leu Val Met Leu Glu Cys
705                 710                 715                 720
Thr Glu Thr Asn Ser Leu Gly Phe Ile Leu Ala Phe Leu Tyr Asn Gly
                725                 730                 735
Leu Leu Ser Ile Ser Ala Phe Ala Cys Ser Tyr Leu Gly Lys Asp Leu
            740                 745                 750
Pro Glu Asn Tyr Asn Glu Ala Lys Cys Val Thr Phe Ser Leu Leu Phe
        755                 760                 765
Asn Phe Val Ser Trp Ile Ala Phe Phe Thr Thr Ala Ser Val Tyr Asp
    770                 775                 780
Gly Lys Tyr Leu Pro Ala Ala Asn Met Met Ala Gly Leu Ser Ser Leu
785                 790                 795                 800
Ser Ser Gly Phe Gly Gly Tyr Phe Leu Pro Lys Cys Tyr Val Ile Leu
                805                 810                 815
Cys Arg Pro Asp Leu Asn Ser Thr Glu His Phe Gln Ala Ser Ile Gln
            820                 825                 830
Asp Tyr Thr Arg Arg Cys Gly Ser Thr
        835                 840

<210> SEQ ID NO 3
<211> LENGTH: 2559
<212> TYPE: DNA
<213> ORGANISM: homo sapiens

<400> SEQUENCE: 3
atgctgggcc ctgctgtcct gggcctcagc ctctgggctc tcctgcaccc tgggacgggg      60
gccccattgt gcctgtcaca gcaacttagg atgaaggggg actacgtgct ggggggggctg    120 ttccccctgg gcgaggccga ggaggctggc ctccgcagcc ggacacggcc cagcagccct     180
gtgtgcacca ggttctcctc aaacggcctg ctctgggcac tggccatgaa atggccgtg      240 gaggagatca caacaagtc ggatctgctg ccgggctgc gcctgggcta cgacctcttt        300
gatacgtgct cggagcctgt ggtggccatg aagcccagcc tcatgttcct ggccaaggca     360
ggcagccgcg acatcgccgc tactgcaac tacacgcagt accagccccg tgtgctggct      420
gtcatcgggc ccactcgtc agagctgccc atggtcaccg caagttctt cagcttcttc       480 ctcatgcccc aggtcagcta cggtgctagc atggagctgc tgagcgcccg ggagaccttc    540
ccctccttct tccgcaccgt gcccagcgac cgtgtgcagc tgacggccgc cgcggagctg   600
ctgcaggagt tcggctggaa ctgggtggcc gccctgggca gcgacgacga gtacggccgg   660
cagggcctga gcatcttctc ggccctggcc gcggcacgcg gcatctgcat cgcgcacgag    720
ggcctggtgc cgctgccccg tgccgatgac tcgcggctgg ggaaggtgca ggacgtcctg    780
caccaggtga accagagcag cgtgcaggtg gtgctgctgt tcgcctccgt gcacgccgcc    840
cacgccctct tcaactacag catcagcagc aggctctcgc ccaaggtgtg ggtgccagc     900 gaggcctggc tgacctctga cctggtcatg gggctgcccg gcatggccca gatgggcacg    960
gtgcttggct tcctccagag gggtgcccag ctgcacgagt tcccccagta cgtgaagacg   1020
cacctggccc tggccaccga cccggccttc tgctctgccc tgggcgagag ggagcagggt    1080
ctggaggagg acgtggtggg ccagcgctgc ccgcagtgtg actgcatcac gctgcagaac    1140
```

```
gtgagcgcag ggctaaatca ccaccagacg ttctctgtct acgcagctgt gtatagcgtg    1200
gcccaggccc tgcacaacac tcttcagtgc aacgcctcag gctgccccgc gcaggacccc    1260
gtgaagccct ggcagctcct ggagaacatg tacaacctga ccttccacgt gggcgggctg    1320
ccgctgcggt tcgacagcag cggaaacgtg acatggagt  acgacctgaa gctgtgggtg    1380
tggcagggct cagtgcccag gctccacgac gtgggcaggt tcaacggcag cctcaggaca    1440
gagcgcctga agatccgctg gcacacgtct gacaaccaga agcccgtgtc ccggtgctcg    1500
cggcagtgcc aggagggcca ggtgcgccgg tcaagggggt tccactcctg ctgctacgac    1560
tgtgtggact gcgaggcggg cagctaccgg caaaacccag acgacatcgc ctgcaccttt    1620
tgtggccagg atgagtggtc cccggagcga agcacacgct gcttccgccg caggtctcgg    1680
ttcctggcat ggggcgagcc ggctgtgctg ctgctgctcc tgctgctgag cctggcgctg    1740
ggccttgtgc tggctgcttt ggggctgttc gttcaccatc gggacagccc actggttcag    1800
gcctcggggg ggcccctggc ctgctttggc ctggtgtgcc tgggcctggt ctgcctcagc    1860
gtcctcctgt tccctggcca gcccagccct gcccgatgcc tggcccagca gcccttgtcc    1920
cacctcccgc tcacgggctg cctgagcaca ctcttcctgc aggcggccga gatcttcgtg    1980
gagtcagaac tgcctctgag ctgggcagac cggctgagtg gctgcctgcg ggggccctgg    2040
gcctggctgg tggtgctgct ggccatgctg gtggaggtcg cactgtgcac ctggtacctg    2100
gtggccttcc cgccggaggt ggtgacggac tggcacatgc tgcccacgga ggcgctggtg    2160
cactgccgca cacgctcctg ggtcagcttc ggcctagcgc acgccaccaa tgccacgctg    2220
gcctttctct gcttcctggg cactttcctg gtgcggagcc agccgggccg ctacaaccgt    2280
gcccgtggcc tcacctttgc catgctggcc tacttcatca cctgggtctc ctttgtgccc    2340
ctcctggcca atgtgcaggt ggtcctcagg cccgccgtgc agatgggcgc cctcctgctc    2400
tgtgtcctgg gcatcctggc tgccttccac ctgcccaggt gttacctgct catgcggcag    2460
ccagggctca acaccccccga gttcttcctg gaggggggcc ctggggatgc ccaaggccag    2520
aatgacggga acacaggaaa tcagggggaaa catgagtaa                          2559
```

<210> SEQ ID NO 4
<211> LENGTH: 852
<212> TYPE: PRT
<213> ORGANISM: homo sapiens

<400> SEQUENCE: 4

Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr

```
                115                 120                 125
Cys Asn Tyr Thr Gln Tyr Gln Pro Arg Val Leu Ala Val Ile Gly Pro
        130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
    290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365

Arg Cys Pro Gln Cys Asp Cys Ile Thr Leu Gln Asn Val Ser Ala Gly
    370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
        435                 440                 445

Asn Val Asp Met Glu Tyr Asp Leu Lys Leu Trp Val Trp Gln Gly Ser
    450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Val Lys
            500                 505                 510

Gly Phe His Ser Cys Cys Tyr Asp Cys Val Asp Cys Glu Ala Gly Ser
        515                 520                 525

Tyr Arg Gln Asn Pro Asp Asp Ile Ala Cys Thr Phe Cys Gly Gln Asp
    530                 535                 540
```

```
Glu Trp Ser Pro Glu Arg Ser Thr Arg Cys Phe Arg Arg Ser Arg
545                 550                 555                 560

Phe Leu Ala Trp Gly Glu Pro Ala Val Leu Leu Leu Leu Leu Leu
            565                 570                 575

Ser Leu Ala Leu Gly Leu Val Leu Ala Ala Leu Gly Leu Phe Val His
        580                 585                 590

His Arg Asp Ser Pro Leu Val Gln Ala Ser Gly Gly Pro Leu Ala Cys
        595                 600                 605

Phe Gly Leu Val Cys Leu Gly Leu Val Cys Leu Ser Val Leu Leu Phe
        610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
            645                 650                 655

Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
        675                 680                 685

Met Leu Val Glu Val Ala Leu Cys Thr Trp Tyr Leu Val Ala Phe Pro
        690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
            725                 730                 735

Asn Ala Thr Leu Ala Phe Leu Cys Phe Leu Gly Thr Phe Leu Val Arg
            740                 745                 750

Ser Gln Pro Gly Arg Tyr Asn Arg Ala Arg Gly Leu Thr Phe Ala Met
        755                 760                 765

Leu Ala Tyr Phe Ile Thr Trp Val Ser Phe Val Pro Leu Leu Ala Asn
        770                 775                 780

Val Gln Val Val Leu Arg Pro Ala Val Gln Met Gly Ala Leu Leu Leu
785                 790                 795                 800

Cys Val Leu Gly Ile Leu Ala Ala Phe His Leu Pro Arg Cys Tyr Leu
            805                 810                 815

Leu Met Arg Gln Pro Gly Leu Asn Thr Pro Glu Phe Phe Leu Gly Gly
        820                 825                 830

Gly Pro Gly Asp Ala Gln Gly Gln Asn Asp Gly Asn Thr Gly Asn Gln
        835                 840                 845

Gly Lys His Glu
    850

<210> SEQ ID NO 5
<211> LENGTH: 3510
<212> TYPE: DNA
<213> ORGANISM: artificial
<220> FEATURE:
<223> OTHER INFORMATION: hT1R1-Rluc

<400> SEQUENCE: 5
atgctgctct gcacggctcg cctggtcggc ctgcagcttc tcatttcctg ctgctgggcc    60
tttgcctgcc atagcacgga gtcttctcct gacttcaccc tccccggaga ttacctcctg    120
gcaggcctgt tccctctcca ttctggctgt ctgcaggtga ggcacagacc cgaggtgacc    180
ctgtgtgaca ggtcttgtag cttcaatgag catggctacc acctcttcca ggctatgcgg    240
```

-continued

| | | | | | |
|---|---|---|---|---|---|
| cttggggttg | aggagataaa | caactccacg | gccctgctgc | ccaacatcac | cctggggtac | 300 |
| cagctgtatg | atgtgtgttc | tgactctgcc | aatgtgtatg | ccacgctgag | agtgctctcc | 360 |
| ctgccagggc | aacaccacat | agagctccaa | ggagaccttc | tccactattc | ccctacggtg | 420 |
| ctggcagtga | ttgggcctga | cagcaccaac | cgtgctgcca | ccacagccgc | cctgctgagc | 480 |
| cctttcctgg | tgcccatgat | tagctatgcg | gccagcagcg | agacgctcag | cgtgaagcgg | 540 |
| cagtatccct | ctttcctgcg | caccatcccc | aatgacaagt | accaggtgga | gaccatggtg | 600 |
| ctgctgctgc | agaagttcgg | gtggacctgg | atctctctgg | ttggcagcag | tgacgactat | 660 |
| gggcagctag | gggtgcaggc | actggagaac | caggccactg | gtcaggggat | ctgcattgct | 720 |
| ttcaaggaca | tcatgccctt | ctctgcccag | gtgggcgatg | agaggatgca | gtgcctcatg | 780 |
| cgccacctgg | cccaggccgg | ggccaccgtc | gtggttgttt | tttccagccg | gcagttggcc | 840 |
| agggtgtttt | tcgagtccgt | ggtgctgacc | aacctgactg | gcaaggtgtg | ggtcgcctca | 900 |
| gaagcctggg | ccctctccag | gcacatcact | ggggtgcccg | ggatccagcg | cattgggatg | 960 |
| gtgctgggcg | tggccatcca | gaagagggct | gtccctggcc | tgaaggcgtt | tgaagaagcc | 1020 |
| tatgcccggg | cagacaagaa | ggcccctagg | ccttgccaca | agggctcctg | gtgcagcagc | 1080 |
| aatcagctct | gcagagaatg | ccaagctttc | atggcacaca | cgatgcccaa | gctcaaagcc | 1140 |
| ttctccatga | gttctgccta | caacgcatac | cgggctgtgt | atgcggtggc | ccatggcctc | 1200 |
| caccagctcc | tgggctgtgc | ctctggagct | tgttccaggg | gccgagtcta | cccctggcag | 1260 |
| cttttggagc | agatccacaa | ggtgcatttc | cttctacaca | aggacactgt | ggcgtttaat | 1320 |
| gacaacagag | atccccctcag | tagctataac | ataattgcct | gggactggaa | tggacccaag | 1380 |
| tggaccttca | cggtcctcgg | ttcctccaca | tggtctccag | ttcagctaaa | cataaatgag | 1440 |
| accaaaatcc | agtggcacgg | aaaggacaac | caggtgccta | agtctgtgtg | ttccagcgac | 1500 |
| tgtcttgaag | ggcaccagcg | agtggttacg | ggtttccatc | actgctgctt | tgagtgtgtg | 1560 |
| ccctgtgggg | ctgggacctt | cctcaacaag | agtgacctct | acagatgcca | gccttgtggg | 1620 |
| aaagaagagt | gggcacctga | gggaagccag | acctgcttcc | cgcgcactgt | ggtgttttg | 1680 |
| gctttgcgtg | agcacacctc | ttgggtgctg | ctggcagcta | acacgctgct | gctgctgctg | 1740 |
| ctgcttggga | ctgctggcct | gttttgcctgg | cacctagaca | ccctgtggt | gaggtcagca | 1800 |
| gggggccgcc | tgtgctttct | tatgctgggc | tccctggcag | caggtagtgg | cagcctctat | 1860 |
| ggcttctttg | gggaacccac | aaggcctgcg | tgcttgctac | gccaggccct | ctttgccctt | 1920 |
| ggtttcacca | tcttcctgtc | ctgcctgaca | gttcgctcat | tccaactaat | catcatcttc | 1980 |
| aagttttcca | ccaaggtacc | tacattctac | cacgcctggg | tccaaaacca | cggtgctggc | 2040 |
| ctgtttgtga | tgatcagctc | agcggcccag | ctgcttatct | gtctaacttg | gctggtggtg | 2100 |
| tggacccac | tgcctgctag | ggaataccag | cgcttccccc | atctggtgat | gcttgagtgc | 2160 |
| acagagacca | actccctggg | cttcatactg | gccttcctct | acaatggcct | cctctccatc | 2220 |
| agtgcctttg | cctgcagcta | cctgggtaag | gacttgccag | agaactacaa | cgaggccaaa | 2280 |
| tgtgtcacct | tcagcctgct | cttcaacttc | gtgtcctgga | tcgccttctt | caccacggcc | 2340 |
| agcgtctacg | acggcaagta | cctgcctgcg | gccaacatga | tggctgggct | gagcagcctg | 2400 |
| agcagcggct | tcggtgggta | ttttctgcct | aagtgctacg | tgatcctctg | ccgcccagac | 2460 |
| ctcaacagca | cagagcactt | ccaggcctcc | attcaggact | acacgaggcg | ctgcggctcc | 2520 |
| accgatatca | agcttgcggt | accgcgggcc | cgggatccac | cggctagagc | caccatgacc | 2580 |
| agcaaggtgt | acgaccccga | gcagaggaag | aggatgatca | ccggcccca | gtggtgggcc | 2640 |

```
aggtgcaagc agatgaacgt gctggacagc ttcatcaact actacgacag cgagaagcac   2700
gccgagaacg ccgtgatctt cctgcacggc aacgccgcta gcagctacct gtggaggcac   2760
gtggtgcccc acatcgagcc cgtggccagg tgcatcatcc ccgatctgat cggcatgggc   2820
aagagcggca agagcggcaa cggcagctac aggctgctgg accactacaa gtacctgacc   2880
gcctggttcg agctcctgaa cctgcccaag aagatcatct tcgtgggcca cgactgggc    2940 gcctgcctgg ccttccacta cagctacgag caccaggaca agatcaaggc catcgtgcac   3000
gccgagagcg tggtggacgt gatcgagagc tgggacgagt ggccagacat cgaggaggac   3060
atcgccctga tcaagagcga ggagggcgag aagatggtgc tggagaacaa cttcttcgtg   3120
gagaccatgc tgcccagcaa gatcatgaga aagctggagc ccgaggagtt cgccgcctac   3180
ctggagccct tcaaggagaa gggcgaggtg agaagaccca ccctgagctg cccagagag    3240 atccccctgg tgaagggcgg caagcccgac gtggtgcaga tcgtgagaaa ctacaacgcc   3300
tacctgagag ccagcgacga cctgcccaag atgttcatcg agagcgaccc cggcttcttc   3360
agcaacgcca tcgtggaggg cgccaagaag ttccccaaca ccgagttcgt gaaggtgaag   3420
ggcctgcact tcagccagga ggacgccccc gacgagatgg gcaagtacat caagagcttc   3480
gtggagagag tgctgaagaa cgagcagtaa                                    3510

<210> SEQ ID NO 6
<211> LENGTH: 1169
<212> TYPE: PRT
<213> ORGANISM: artificial
<220> FEATURE:
<223> OTHER INFORMATION: hT1R1-Rluc

<400> SEQUENCE: 6

Met Leu Leu Cys Thr Ala Arg Leu Val Gly Leu Gln Leu Leu Ile Ser
1               5                   10                  15

Cys Cys Trp Ala Phe Ala Cys His Ser Thr Glu Ser Ser Pro Asp Phe
            20                  25                  30

Thr Leu Pro Gly Asp Tyr Leu Leu Ala Gly Leu Phe Pro Leu His Ser
        35                  40                  45

Gly Cys Leu Gln Val Arg His Arg Pro Glu Val Thr Leu Cys Asp Arg
    50                  55                  60

Ser Cys Ser Phe Asn Glu His Gly Tyr His Leu Phe Gln Ala Met Arg
65                  70                  75                  80

Leu Gly Val Glu Glu Ile Asn Asn Ser Thr Ala Leu Leu Pro Asn Ile
                85                  90                  95

Thr Leu Gly Tyr Gln Leu Tyr Asp Val Cys Ser Asp Ser Ala Asn Val
            100                 105                 110

Tyr Ala Thr Leu Arg Val Leu Ser Leu Pro Gly Gln His His Ile Glu
        115                 120                 125

Leu Gln Gly Asp Leu Leu His Tyr Ser Pro Thr Val Leu Ala Val Ile
    130                 135                 140

Gly Pro Asp Ser Thr Asn Arg Ala Ala Thr Thr Ala Ala Leu Leu Ser
145                 150                 155                 160

Pro Phe Leu Val Pro Met Ile Ser Tyr Ala Ala Ser Ser Glu Thr Leu
                165                 170                 175

Ser Val Lys Arg Gln Tyr Pro Ser Phe Leu Arg Thr Ile Pro Asn Asp
            180                 185                 190

Lys Tyr Gln Val Glu Thr Met Val Leu Leu Leu Gln Lys Phe Gly Trp
        195                 200                 205
```

-continued

```
Thr Trp Ile Ser Leu Val Gly Ser Ser Asp Tyr Gly Gln Leu Gly
    210                 215                 220
Val Gln Ala Leu Glu Asn Gln Ala Thr Gly Gln Gly Ile Cys Ile Ala
225                 230                 235                 240
Phe Lys Asp Ile Met Pro Phe Ser Ala Gln Val Gly Asp Glu Arg Met
                    245                 250                 255
Gln Cys Leu Met Arg His Leu Ala Gln Ala Gly Ala Thr Val Val Val
                260                 265                 270
Val Phe Ser Ser Arg Gln Leu Ala Arg Val Phe Phe Glu Ser Val Val
            275                 280                 285
Leu Thr Asn Leu Thr Gly Lys Val Trp Val Ala Ser Glu Ala Trp Ala
    290                 295                 300
Leu Ser Arg His Ile Thr Gly Val Pro Gly Ile Gln Arg Ile Gly Met
305                 310                 315                 320
Val Leu Gly Val Ala Ile Gln Lys Arg Ala Val Pro Gly Leu Lys Ala
                325                 330                 335
Phe Glu Glu Ala Tyr Ala Arg Ala Asp Lys Lys Ala Pro Arg Pro Cys
                340                 345                 350
His Lys Gly Ser Trp Cys Ser Ser Asn Gln Leu Cys Arg Glu Cys Gln
            355                 360                 365
Ala Phe Met Ala His Thr Met Pro Lys Leu Lys Ala Phe Ser Met Ser
    370                 375                 380
Ser Ala Tyr Asn Ala Tyr Arg Ala Val Tyr Ala Val Ala His Gly Leu
385                 390                 395                 400
His Gln Leu Leu Gly Cys Ala Ser Gly Ala Cys Ser Arg Gly Arg Val
                405                 410                 415
Tyr Pro Trp Gln Leu Leu Glu Gln Ile His Lys Val His Phe Leu Leu
                420                 425                 430
His Lys Asp Thr Val Ala Phe Asn Asp Asn Arg Asp Pro Leu Ser Ser
            435                 440                 445
Tyr Asn Ile Ile Ala Trp Asp Trp Asn Gly Pro Lys Trp Thr Phe Thr
    450                 455                 460
Val Leu Gly Ser Ser Thr Trp Ser Pro Val Gln Leu Asn Ile Asn Glu
465                 470                 475                 480
Thr Lys Ile Gln Trp His Gly Lys Asp Asn Gln Val Pro Lys Ser Val
                485                 490                 495
Cys Ser Ser Asp Cys Leu Glu Gly His Gln Arg Val Val Thr Gly Phe
            500                 505                 510
His His Cys Cys Phe Glu Cys Val Pro Cys Gly Ala Gly Thr Phe Leu
    515                 520                 525
Asn Lys Ser Asp Leu Tyr Arg Cys Gln Pro Cys Gly Lys Glu Glu Trp
530                 535                 540
Ala Pro Glu Gly Ser Gln Thr Cys Phe Pro Arg Thr Val Val Phe Leu
545                 550                 555                 560
Ala Leu Arg Glu His Thr Ser Trp Val Leu Leu Ala Ala Asn Thr Leu
                565                 570                 575
Leu Leu Leu Leu Leu Leu Gly Thr Ala Gly Leu Phe Ala Trp His Leu
                580                 585                 590
Asp Thr Pro Val Val Arg Ser Ala Gly Gly Arg Leu Cys Phe Leu Met
            595                 600                 605
Leu Gly Ser Leu Ala Ala Gly Ser Gly Ser Leu Tyr Gly Phe Phe Gly
    610                 615                 620
```

```
Glu Pro Thr Arg Pro Ala Cys Leu Leu Arg Gln Ala Leu Phe Ala Leu
625                 630                 635                 640

Gly Phe Thr Ile Phe Leu Ser Cys Leu Thr Val Arg Ser Phe Gln Leu
            645                 650                 655

Ile Ile Ile Phe Lys Phe Ser Thr Lys Val Pro Thr Phe Tyr His Ala
            660                 665                 670

Trp Val Gln Asn His Gly Ala Gly Leu Phe Val Met Ile Ser Ser Ala
        675                 680                 685

Ala Gln Leu Leu Ile Cys Leu Thr Trp Leu Val Val Trp Thr Pro Leu
690                 695                 700

Pro Ala Arg Glu Tyr Gln Arg Phe Pro His Leu Val Met Leu Glu Cys
705                 710                 715                 720

Thr Glu Thr Asn Ser Leu Gly Phe Ile Leu Ala Phe Leu Tyr Asn Gly
                725                 730                 735

Leu Leu Ser Ile Ser Ala Phe Ala Cys Ser Tyr Leu Gly Lys Asp Leu
            740                 745                 750

Pro Glu Asn Tyr Asn Glu Ala Lys Cys Val Thr Phe Ser Leu Leu Phe
        755                 760                 765

Asn Phe Val Ser Trp Ile Ala Phe Phe Thr Thr Ala Ser Val Tyr Asp
770                 775                 780

Gly Lys Tyr Leu Pro Ala Ala Asn Met Met Ala Gly Leu Ser Ser Leu
785                 790                 795                 800

Ser Ser Gly Phe Gly Gly Tyr Phe Leu Pro Lys Cys Tyr Val Ile Leu
                805                 810                 815

Cys Arg Pro Asp Leu Asn Ser Thr Glu His Phe Gln Ala Ser Ile Gln
            820                 825                 830

Asp Tyr Thr Arg Arg Cys Gly Ser Thr Asp Ile Lys Leu Ala Val Pro
        835                 840                 845

Arg Ala Arg Asp Pro Pro Ala Arg Ala Thr Met Thr Ser Lys Val Tyr
850                 855                 860

Asp Pro Glu Gln Arg Lys Arg Met Ile Thr Gly Pro Gln Trp Trp Ala
865                 870                 875                 880

Arg Cys Lys Gln Met Asn Val Leu Asp Ser Phe Ile Asn Tyr Tyr Asp
                885                 890                 895

Ser Glu Lys His Ala Glu Asn Ala Val Ile Phe Leu His Gly Asn Ala
            900                 905                 910

Ala Ser Ser Tyr Leu Trp Arg His Val Val Pro His Ile Glu Pro Val
        915                 920                 925

Ala Arg Cys Ile Ile Pro Asp Leu Ile Gly Met Gly Lys Ser Gly Lys
930                 935                 940

Ser Gly Asn Gly Ser Tyr Arg Leu Leu Asp His Tyr Lys Tyr Leu Thr
945                 950                 955                 960

Ala Trp Phe Glu Leu Leu Asn Leu Pro Lys Lys Ile Ile Phe Val Gly
                965                 970                 975

His Asp Trp Gly Ala Cys Leu Ala Phe His Tyr Ser Tyr Glu His Gln
            980                 985                 990

Asp Lys Ile Lys Ala Ile Val His Ala Glu Ser Val Val Asp Val Ile
        995                 1000                 1005

Glu Ser Trp Asp Glu Trp Pro Asp Ile Glu Glu Asp Ile Ala Leu
        1010                 1015                 1020

Ile Lys Ser Glu Glu Gly Glu Lys Met Val Leu Glu Asn Asn Phe
        1025                 1030                 1035

Phe Val Glu Thr Met Leu Pro Ser Lys Ile Met Arg Lys Leu Glu
```

-continued

```
               1040                1045                1050
Pro Glu Glu Phe Ala Ala Tyr Leu Glu Pro Phe Lys Glu Lys Gly
        1055                1060                1065

Glu Val Arg Arg Pro Thr Leu Ser Trp Pro Arg Glu Ile Pro Leu
    1070                1075                1080

Val Lys Gly Gly Lys Pro Asp Val Val Gln Ile Val Arg Asn Tyr
1085                1090                1095

Asn Ala Tyr Leu Arg Ala Ser Asp Asp Leu Pro Lys Met Phe Ile
    1100                1105                1110

Glu Ser Asp Pro Gly Phe Phe Ser Asn Ala Ile Val Glu Gly Ala
    1115                1120                1125

Lys Lys Phe Pro Asn Thr Glu Phe Val Lys Val Lys Gly Leu His
    1130                1135                1140

Phe Ser Gln Glu Asp Ala Pro Asp Glu Met Gly Lys Tyr Ile Lys
    1145                1150                1155

Ser Phe Val Glu Arg Val Leu Lys Asn Glu Gln
    1160                1165
```

<210> SEQ ID NO 7
<211> LENGTH: 3543
<212> TYPE: DNA
<213> ORGANISM: artificial
<220> FEATURE:
<223> OTHER INFORMATION: hT1R3-Rluc

<400> SEQUENCE: 7

```
atgctgggcc ctgctgtcct gggcctcagc ctctgggctc tcctgcaccc tgggacgggg      60
gccccattgt gcctgtcaca gcaacttagg atgaaggggg actacgtgct ggggggggctg    120
ttccccctgg gcgaggccga ggaggctggc ctccgcagcc ggacacggcc cagcagccct    180
gtgtgcacca ggttctcctc aaacggcctg ctctgggcac tggccatgaa aatggccgtg    240
gaggagatca caacaagtc ggatctgctg cccgggctgc gctgggcta cgacctcttt    300
gatacgtgct cggagcctgt ggtggccatg aagcccagcc tcatgttcct ggccaaggca    360
ggcagccgcg acatcgccgc ctactgcaac tacacgcagt accagccccg tgtgctggct    420
gtcatcgggc ccactcgtc agagctcgcc atggtcaccg gcaagttctt cagcttcttc    480
ctcatgcccc aggtcagcta cggtgctagc atggagctgc tgagcgcccg ggagaccttc    540
ccctccttct tccgcaccgt gcccagcgac cgtgtgcagc tgacggccgc cgcggagctg    600
ctgcaggagt cggctggaa ctgggtggcc ccctgggca cgacgacga gtacggccgg    660
cagggcctga gcatcttctc gccctggcc gcggcacgcg gcatctgcat cgcgcacgag    720
ggcctggtgc cgctgccccg tgccgatgac tcgcggctgg ggaaggtgca ggacgtcctg    780
caccaggtga accagagcag cgtgcaggtg gtgctgctgt tcgcctccgt gcacgccgcc    840
cacgccctct tcaactacag catcagcagc aggctctcgc caaggtgtg ggtggccagc    900
gaggcctggc tgacctctga cctggtcatg ggcctgcccg gcatggccca gatgggcacg    960
gtgcttggct tcctccagag gggtgcccag ctgcacgagt tccccccagta cgtgaagacg   1020
cacctggccc tggccaccga cccggccttc tgctctgccc tgggcgagag ggagcagggt   1080
ctggaggagg acgtggtggg ccagcgctgc ccgcagtgtg actgcatcac gctgcagaac   1140
gtgagcgcag gctaaatca ccaccagacg ttctctgtct acgcagctgt gtatagcgtg   1200
gcccaggccc tgcacaacac tcttcagtgc aacgcctcag ctgccccgc gcaggacccc   1260
gtgaagccct ggcagctcct ggagaacatg tacaacctga ccttccacgt gggcgggctg   1320
```

```
ccgctgcggt tcgacagcag cggaaacgtg gacatggagt acgacctgaa gctgtgggtg    1380
tggcagggct cagtgcccag gctccacgac gtgggcaggt caacggcag cctcaggaca     1440 gagcgcctga agatccgctg gcacacgtct gacaaccaga agcccgtgtc ccggtgctcg    1500
cggcagtgcc aggagggcca ggtgcgccgg gtcaaggggt ccactcctg ctgctacgac     1560 tgtgtggact gcgaggcggg cagctaccgg caaaacccag acgacatcgc ctgcaccttt    1620
tgtggccagg atgagtggtc cccggagcga agcacacgct gcttccgccg caggtctcgg   1680
ttcctggcat ggggcgagcc ggctgtgctg ctgctgctcc tgctgctgag cctggcgctg    1740
ggccttgtgc tggctgcttt ggggctgttc gttcaccatc gggacagccc actggttcag    1800
gcctcggggg ggcccctggc ctgctttggc ctggtgtgcc tgggcctggt ctgcctcagc    1860
gtcctcctgt tccctggcca gcccagccct gcccgatgcc tggcccagca gcccttgtcc    1920
cacctcccgc tcacgggctg cctgagcaca ctcttcctgc aggcggccga gatcttcgtg    1980
gagtcagaac tgcctctgag ctgggcagac cggctgagtg gctgcctgcg ggggccctgg    2040
gcctggctgg tggtgctgct ggccatgctg gtggaggtcg cactgtgcac ctggtacctg    2100
gtggccttcc cgccggaggt ggtgacggac tggcacatgc tgcccacgga ggcgctggtg    2160
cactgccgca cacgctcctg ggtcagcttc ggcctagcgc acgccaccaa tgccacgctg    2220
gcctttctct gcttcctggg cactttcctg gtgcggagcc agccgggccg ctacaaccgt    2280
gcccgtggcc tcacctttgc catgctggcc tacttcatca cctgggtctc ctttgtgccc    2340
ctcctggcca atgtgcaggt ggtcctcagg cccgccgtgc agatgggcgc cctcctgctc    2400
tgtgtcctgg gcatcctggc tgccttccac ctgcccaggt gttacctgct catgcggcag    2460
ccagggctca acacccccga gttcttcctg gaggggggcc ctggggatgc caaggccag    2520 aatgacggga acacaggaaa tcaggggaaa catgaggata tcaagcttgc ggtaccgcgg    2580
gcccgggatc caccggctag agccaccatg accagcaagg tgtacgaccc cgagcagagg    2640
aagaggatga tcaccggccc ccagtggtgg gccaggtgca agcagatgaa cgtgctggac    2700
agcttcatca actactacga cagcgagaag cacgccgaga cgccgtgat cttcctgcac   2760 ggcaacgccg ctagcagcta cctgtggagg cacgtggtgc cccacatcga gcccgtggcc    2820
aggtgcatca tccccgatct gatcggcatg ggcaagagcg gcaagagcgg caacggcagc    2880
tacaggctgc tggaccacta caagtacctg accgcctggt tcgagctcct gaacctgccc    2940
aagaagatca tcttcgtggg ccacgactgg ggcgcctgcc tggccttcca ctacagctac    3000
gagcaccagg acaagatcaa ggccatcgtg cacgccgaga gcgtggtgga cgtgatcgag    3060
agctgggacg agtggccaga catcgaggag gacatcgccc tgatcaagag cgaggagggc    3120
gagaagatgg tgctggagaa caacttcttc gtggagacca tgctgcccag caagatcatg    3180
agaaagctgg agcccgagga gttcgccgcc tacctggagc ccttcaagga agggcgag    3240 gtgagaagac ccaccctgag ctggcccaga gagatccccc tggtgaaggg cggcaagccc    3300
gacgtggtgc agatcgtgag aaactacaac gcctacctga gagccagcga cgacctgccc    3360
aagatgttca tcgagagcga ccccggcttc ttcagcaacg ccatcgtgga gggcgccaag    3420
aagttcccca acaccgagtt cgtgaaggtg aagggcctgc acttcagcca ggaggacgcc    3480
cccgacgaga tggcaagta catcaagagc ttcgtggaga gagtgctgaa gaacgagcag    3540
taa                                                                 3543
```

<210> SEQ ID NO 8

<211> LENGTH: 1180
<212> TYPE: PRT
<213> ORGANISM: artificial
<220> FEATURE:
<223> OTHER INFORMATION: hT1R3-Rluc

<400> SEQUENCE: 8

```
Met Leu Gly Pro Ala Val Leu Gly Leu Ser Leu Trp Ala Leu Leu His
1               5                   10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

Phe Ser Ser Asn Gly Leu Leu Trp Ala Leu Ala Met Lys Met Ala Val
65                  70                  75                  80

Glu Glu Ile Asn Asn Lys Ser Asp Leu Leu Pro Gly Leu Arg Leu Gly
                85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
    290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365

Arg Cys Pro Gln Cys Asp Cys Ile Thr Leu Gln Asn Val Ser Ala Gly
    370                 375                 380
```

```
Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
            405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
            435                 440                 445

Asn Val Asp Met Glu Tyr Asp Leu Lys Leu Trp Val Trp Gln Gly Ser
            450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
            515                 520                 525

Tyr Arg Gln Asn Pro Asp Asp Ile Ala Cys Thr Phe Cys Gly Gln Asp
            530                 535                 540

Glu Trp Ser Pro Glu Arg Ser Thr Arg Cys Phe Arg Arg Ser Arg
545                 550                 555                 560

Phe Leu Ala Trp Gly Glu Pro Ala Val Leu Leu Leu Leu Leu Leu Leu
                565                 570                 575

Ser Leu Ala Leu Gly Leu Val Leu Ala Leu Gly Leu Phe Val His
            580                 585                 590

His Arg Asp Ser Pro Leu Val Gln Ala Ser Gly Gly Pro Leu Ala Cys
            595                 600                 605

Phe Gly Leu Val Cys Leu Gly Leu Val Cys Leu Ser Val Leu Leu Phe
            610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
                645                 650                 655

Glu Ile Phe Val Glu Ser Glu Leu Pro Leu Ser Trp Ala Asp Arg Leu
                660                 665                 670

Ser Gly Cys Leu Arg Gly Pro Trp Ala Trp Leu Val Val Leu Leu Ala
            675                 680                 685

Met Leu Val Glu Val Ala Leu Cys Thr Trp Tyr Leu Val Ala Phe Pro
            690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
                725                 730                 735

Asn Ala Thr Leu Ala Phe Leu Cys Phe Leu Gly Thr Phe Leu Val Arg
                740                 745                 750

Ser Gln Pro Gly Arg Tyr Asn Arg Ala Arg Gly Leu Thr Phe Ala Met
            755                 760                 765

Leu Ala Tyr Phe Ile Thr Trp Val Ser Phe Val Pro Leu Leu Ala Asn
            770                 775                 780

Val Gln Val Val Leu Arg Pro Ala Val Gln Met Gly Ala Leu Leu Leu
785                 790                 795                 800
```

```
Cys Val Leu Gly Ile Leu Ala Ala Phe His Leu Pro Arg Cys Tyr Leu
                805                 810                 815

Leu Met Arg Gln Pro Gly Leu Asn Thr Pro Glu Phe Phe Leu Gly Gly
        820                 825                 830

Gly Pro Gly Asp Ala Gln Gly Asn Asp Gly Asn Thr Gly Asn Gln
            835                 840                 845

Gly Lys His Glu Asp Ile Lys Leu Ala Val Pro Arg Ala Arg Asp Pro
    850                 855                 860

Pro Ala Arg Ala Thr Met Thr Ser Lys Val Tyr Asp Pro Glu Gln Arg
865                 870                 875                 880

Lys Arg Met Ile Thr Gly Pro Gln Trp Trp Ala Arg Cys Lys Gln Met
                885                 890                 895

Asn Val Leu Asp Ser Phe Ile Asn Tyr Tyr Asp Ser Glu Lys His Ala
                900                 905                 910

Glu Asn Ala Val Ile Phe Leu His Gly Asn Ala Ala Ser Ser Tyr Leu
            915                 920                 925

Trp Arg His Val Val Pro His Ile Glu Pro Val Ala Arg Cys Ile Ile
    930                 935                 940

Pro Asp Leu Ile Gly Met Gly Lys Ser Gly Lys Ser Gly Asn Gly Ser
945                 950                 955                 960

Tyr Arg Leu Leu Asp His Tyr Lys Tyr Leu Thr Ala Trp Phe Glu Leu
                965                 970                 975

Leu Asn Leu Pro Lys Lys Ile Ile Phe Val Gly His Asp Trp Gly Ala
                980                 985                 990

Cys Leu Ala Phe His Tyr Ser Tyr Glu His Gln Asp Lys Ile Lys Ala
            995                 1000                1005

Ile Val His Ala Glu Ser Val Val Asp Val Ile Glu Ser Trp Asp
    1010                1015                1020

Glu Trp Pro Asp Ile Glu Glu Asp Ile Ala Leu Ile Lys Ser Glu
    1025                1030                1035

Glu Gly Glu Lys Met Val Leu Glu Asn Asn Phe Phe Val Glu Thr
    1040                1045                1050

Met Leu Pro Ser Lys Ile Met Arg Lys Leu Glu Pro Glu Glu Phe
    1055                1060                1065

Ala Ala Tyr Leu Glu Pro Phe Lys Glu Lys Gly Glu Val Arg Arg
    1070                1075                1080

Pro Thr Leu Ser Trp Pro Arg Glu Ile Pro Leu Val Lys Gly Gly
    1085                1090                1095

Lys Pro Asp Val Val Gln Ile Val Arg Asn Tyr Asn Ala Tyr Leu
    1100                1105                1110

Arg Ala Ser Asp Asp Leu Pro Lys Met Phe Ile Glu Ser Asp Pro
    1115                1120                1125

Gly Phe Phe Ser Asn Ala Ile Val Glu Gly Ala Lys Lys Phe Pro
    1130                1135                1140

Asn Thr Glu Phe Val Lys Val Lys Gly Leu His Phe Ser Gln Glu
    1145                1150                1155

Asp Ala Pro Asp Glu Met Gly Lys Tyr Ile Lys Ser Phe Val Glu
    1160                1165                1170

Arg Val Leu Lys Asn Glu Gln
    1175                1180

<210> SEQ ID NO 9
<211> LENGTH: 2521
<212> TYPE: DNA
```

<213> ORGANISM: homo sapiens

<400> SEQUENCE: 9

```
catgggccc agggcaaaga ccatctcctc cctgttcttc ctcctatggg tcctggctga      60
gccggctgag aactcggact tctacctgcc tggggattac ctcctgggtg gcctcttctc     120
cctccatgcc aacatgaagg gcattgttca ccttaacttc ctgcaggtgc ccatgtgcaa     180
ggagtatgaa gtgaaggtga taggctacaa cctcatgcag gccatgcgct ttgcggtgga     240
ggagatcaac aatgacagca gcctgctgcc tggtgtgctg ctgggctatg agatcgtgga     300
tgtgtgctac atctccaaca atgtccagcc ggtgctctac ttcctggcac acgaggacaa     360
cctccttccc atccaagagg actacagtaa ctacatttcc cgtgtggtgg ctgtcattgg     420
ccctgacaac tccgagtctg tcatgactgt ggccaacttc ctctccctat ttctccttcc     480
acagatcacc tacagcgcca tcagcgatga gctgcgagac aaggtgcgct cccggctttt     540
gctgcgtacc acacccagcg ccgaccacca catcgaggcc atggtgcagc tgatgctgca     600
cttccgctgg aactggatca ttgtgctggt gagcagcgac acctatggcc gcgacaatgg     660
ccagctgctt ggcgagcgcg tggccggcg cgacatctgc atcgccttcc aggagacgct     720
gcccacactg cagcccaacc agaacatgac gtcagaggag cgccagcgcc tggtgaccat     780
tgtggacaag ctgcagcaga gcacagcgcg cgtcgtggtc gtgttctcgc ccgacctgac     840
cctgtaccac ttcttcaatg aggtgctgcg ccagaacttc actggcgccg tgtggatcgc     900
ctccgagtcc tgggccatcg acccggtcct gcacaacctc acggagctgc gccacttggg     960
caccttcctg ggcatcacca tccagagcgt gcccatcccg gcttcagtg agttccgcga    1020
gtggggccca caggctgggc cgccacccct cagcaggacc agccagagct atacctgcaa    1080
ccaggagtgc gacaactgcc tgaacgccac cttgtccttc aacaccattc tcaggctctc    1140
tggggagcgt gtcgtctaca gcgtgtactc tgcggtctat gctgtggccc atgccctgca    1200
cagcctcctc ggctgtgaca aaagcacctg caccaagagg gtggtctacc cctggcagct    1260
gcttgaggag atctggaagg tcaacttcac tctcctggac caccaaatct tcttcgaccc    1320
gcaaggggac gtggctctgc acttggagat tgtccagtgg caatgggacc ggagccagaa    1380
tcccttccag agcgtcgcct cctactaccc cctgcagcga cagctgaaga acatccaaga    1440
catctcctgg cacaccatca acaacacgat ccctatgtcc atgtgttcca agaggtgcca    1500
gtcagggcaa aagaagaagc tgtgggcat ccacgtctgc tgcttcgagt gcatcgactg    1560
ccttcccggc accttcctca accacactga agatgaatat gaatgccagg cctgcccgaa    1620
taacgagtgg tcctaccaga gtgagacctc ctgcttcaag cggcagctgg tcttcctgga    1680
atggcatgag gcacccacca tcgctgtggc cctgctggcc gccctgggct tcctcagcac    1740
cctggccatc ctggtgatat tctggaggca cttccagaca cccatagttc gctcggctgg    1800
gggccccatg tgcttcctga tgctgacact gctgctggtg gcatacatgg tggtcccggt    1860
gtacgtgggg ccgcccaagg tctccacctg cctctgccgc caggccctct ttccctctg    1920
cttcacaatc tgcatctcct gtatcgccgt gcgttctttc cagatcgtct gcgccttcaa    1980
gatgccagc cgcttccac gcgcctacag ctactgggtc cgctaccagg ggccctacgt    2040
ctctatggca tttatcacgg tactcaaaat ggtcattgtg gtaattggca tgctggccac    2100
gggcctcagt cccaccaccc gtactgaccc cgatgacccc aagatcacaa ttgtctcctg    2160
taaccccaac taccgcaaca gcctgctgtt caacaccagc ctggacctgc tgctctcagt    2220
ggtgggtttc agcttcgcct acatgggcaa agagctgccc accaactaca acgaggccaa    2280
```

-continued

```
gttcatcacc ctcagcatga ccttctattt cacctcatcc gtctccctct gcaccttcat    2340
gtctgcctac agcggggtgc tggtcaccat cgtggacctc ttggtcactg tgctcaacct    2400
cctggccatc agcctgggct acttcggccc caagtgctac atgatcctct tctacccgga    2460
gcgcaacacg cccgcctact tcaacagcat gatccagggc tacaccatga ggagggacta    2520
g                                                                    2521
```

<210> SEQ ID NO 10
<211> LENGTH: 789
<212> TYPE: PRT
<213> ORGANISM: homo sapiens

<400> SEQUENCE: 10

```
Leu Asn Phe Leu Gln Val Pro Met Cys Lys Glu Tyr Glu Val Lys Val
1               5                   10                  15

Ile Gly Tyr Asn Leu Met Gln Ala Met Arg Phe Ala Val Glu Glu Ile
            20                  25                  30

Asn Asn Asp Ser Ser Leu Leu Pro Gly Val Leu Leu Gly Tyr Glu Ile
        35                  40                  45

Val Asp Val Cys Tyr Ile Ser Asn Asn Val Gln Pro Val Leu Tyr Phe
    50                  55                  60

Leu Ala His Glu Asp Asn Leu Leu Pro Ile Gln Glu Asp Tyr Ser Asn
65                  70                  75                  80

Tyr Ile Ser Arg Val Val Ala Val Ile Gly Pro Asp Asn Ser Glu Ser
                85                  90                  95

Val Met Thr Val Ala Asn Phe Leu Ser Leu Phe Leu Leu Pro Gln Ile
            100                 105                 110

Thr Tyr Ser Ala Ile Ser Asp Glu Leu Arg Asp Lys Val Arg Phe Pro
        115                 120                 125

Ala Leu Leu Arg Thr Thr Pro Ser Ala Asp His His Ile Glu Ala Met
    130                 135                 140

Val Gln Leu Met Leu His Phe Arg Trp Asn Trp Ile Ile Val Leu Val
145                 150                 155                 160

Ser Ser Asp Thr Tyr Gly Arg Asp Asn Gly Gln Leu Leu Gly Glu Arg
                165                 170                 175

Val Ala Arg Arg Asp Ile Cys Ile Ala Phe Gln Glu Thr Leu Pro Thr
            180                 185                 190

Leu Gln Pro Asn Gln Asn Met Thr Ser Glu Glu Arg Gln Arg Leu Val
        195                 200                 205

Thr Ile Val Asp Lys Leu Gln Gln Ser Thr Ala Arg Val Val Val Val
    210                 215                 220

Phe Ser Pro Asp Leu Thr Leu Tyr His Phe Phe Asn Glu Val Leu Arg
225                 230                 235                 240

Gln Asn Phe Thr Gly Ala Val Trp Ile Ala Ser Glu Ser Trp Ala Ile
                245                 250                 255

Asp Pro Val Leu His Asn Leu Thr Glu Leu Arg His Leu Gly Thr Phe
            260                 265                 270

Leu Gly Ile Thr Ile Gln Ser Val Pro Ile Pro Gly Phe Ser Glu Phe
        275                 280                 285

Arg Glu Trp Gly Pro Gln Ala Gly Pro Pro Leu Ser Arg Thr Ser
    290                 295                 300

Gln Ser Tyr Thr Cys Asn Gln Glu Cys Asp Asn Cys Leu Asn Ala Thr
305                 310                 315                 320
```

-continued

```
Leu Ser Phe Asn Thr Ile Leu Arg Leu Ser Gly Glu Arg Val Val Tyr
                325                 330                 335
Ser Val Tyr Ser Ala Val Tyr Ala Val Ala His Ala Leu His Ser Leu
            340                 345                 350
Leu Gly Cys Asp Lys Ser Thr Cys Thr Lys Arg Val Val Tyr Pro Trp
        355                 360                 365
Gln Leu Leu Glu Glu Ile Trp Lys Val Asn Phe Thr Leu Leu Asp His
    370                 375                 380
Gln Ile Phe Phe Asp Pro Gln Gly Asp Val Ala Leu His Leu Glu Ile
385                 390                 395                 400
Val Gln Trp Gln Trp Asp Arg Ser Gln Asn Pro Phe Gln Ser Val Ala
                405                 410                 415
Ser Tyr Tyr Pro Leu Gln Arg Gln Leu Lys Asn Ile Gln Asp Ile Ser
            420                 425                 430
Trp His Thr Ile Asn Asn Thr Ile Pro Met Ser Met Cys Ser Lys Arg
        435                 440                 445
Cys Gln Ser Gly Gln Lys Lys Lys Pro Val Gly Ile His Val Cys Cys
    450                 455                 460
Phe Glu Cys Ile Asp Cys Leu Pro Gly Thr Phe Leu Asn His Thr Glu
465                 470                 475                 480
Asp Glu Tyr Glu Cys Gln Ala Cys Pro Asn Asn Glu Trp Ser Tyr Gln
                485                 490                 495
Ser Glu Thr Ser Cys Phe Lys Arg Gln Leu Val Phe Leu Glu Trp His
            500                 505                 510
Glu Ala Pro Thr Ile Ala Val Ala Leu Leu Ala Ala Leu Gly Phe Leu
        515                 520                 525
Ser Thr Leu Ala Ile Leu Val Ile Phe Trp Arg His Phe Gln Thr Pro
    530                 535                 540
Ile Val Arg Ser Ala Gly Gly Pro Met Cys Phe Leu Met Leu Thr Leu
545                 550                 555                 560
Leu Leu Val Ala Tyr Met Val Val Pro Val Tyr Val Gly Pro Pro Lys
                565                 570                 575
Val Ser Thr Cys Leu Cys Arg Gln Ala Leu Phe Pro Leu Cys Phe Thr
            580                 585                 590
Ile Cys Ile Ser Cys Ile Ala Val Arg Ser Phe Gln Ile Val Cys Ala
        595                 600                 605
Phe Lys Met Ala Ser Arg Phe Pro Arg Ala Tyr Ser Tyr Trp Val Arg
    610                 615                 620
Tyr Gln Gly Pro Tyr Val Ser Met Ala Phe Ile Thr Val Leu Lys Met
625                 630                 635                 640
Val Ile Val Val Ile Gly Met Leu Ala Thr Gly Leu Ser Pro Thr Thr
                645                 650                 655
Arg Thr Asp Pro Asp Pro Lys Ile Thr Ile Val Ser Cys Asn Pro
            660                 665                 670
Asn Tyr Arg Asn Ser Leu Leu Phe Asn Thr Ser Leu Asp Leu Leu Leu
        675                 680                 685
Ser Val Val Gly Phe Ser Phe Ala Tyr Met Gly Lys Glu Leu Pro Thr
    690                 695                 700
Asn Tyr Asn Glu Ala Lys Phe Ile Thr Leu Ser Met Thr Phe Tyr Phe
705                 710                 715                 720
Thr Ser Ser Val Ser Leu Cys Thr Phe Met Ser Ala Tyr Ser Gly Val
                725                 730                 735
Leu Val Thr Ile Val Asp Leu Leu Val Thr Val Leu Asn Leu Leu Ala
```

```
        740             745             750
Ile Ser Leu Gly Tyr Phe Gly Pro Lys Cys Tyr Met Ile Leu Phe Tyr
        755             760             765

Pro Glu Arg Asn Thr Pro Ala Tyr Phe Asn Ser Met Ile Gln Gly Tyr
        770             775             780

Thr Met Arg Arg Asp
785

<210> SEQ ID NO 11
<211> LENGTH: 2739
<212> TYPE: DNA
<213> ORGANISM: homo sapiens

<400> SEQUENCE: 11
atgcctggga agagaggctt gggctggtgg tgggcccggc tgccccttg cctgctcctc    60 agcctttacg gccctggat gccttcctcc ctgggaaagc ccaaggcca ccctcacatg    120 aattccatcc gcatagatgg ggacatcaca ctgggaggcc tgttcccggt gcatggccgg    180
ggctcagagg gcaagccctg tggagaactt aagaaggaaa agggcatcca ccggctggag    240
gccatgctgt tcgccctgga tcgcatcaac aacgacccgg acctgctgcc taacatcacg    300
ctgggcgccc gcattctgga cacctgctcc agggacaccc atgccctcga gcagtcgctg    360
acctttgtgc aggcgctcat cgagaaggat ggcacagagg tccgctgtgg cagtggcggc    420
ccacccatca tcaccaagcc tgaacgtgtg gtgggtgtca tcggtgcttc agggagctcg    480
gtctccatca tggtggccaa catccttcgc ctcttcaaga taccccagat cagctacgcc    540
tccacagcgc cagacctgag tgacaacagc cgctacgact tcttctcccg cgtggtgccc    600
tcggacacgt accaggccca ggccatggtg gacatcgtcc gtgccctcaa gtggaactat    660
gtgtccacag tggcctcgga gggcagctat ggtgagagcg tgtggaggc cttcatccag    720 aagtcccgtg aggacggggg cgtgtgcatc gcccagtcgg tgaagatacc acgggagccc    780
aaggcaggcg agttcgacaa gatcatccgc cgcctcctgg agacttcgaa cgccagggca    840
gtcatcatct tgccaacga ggatgacatc aggcgtgtgc tggaggcagc acgaagggcc    900
aaccagacag gccatttctt ctggatgggc tctgacagct ggggctccaa gattgcacct    960
gtgctgcacc tggaggaggt ggctgagggt gctgtcacga tcctccccaa gaggatgtcc   1020
gtacgaggct tcgaccgcta cttctccagc cgcacgctgg acaacaaccg cgcgaacatc   1080
tggtttgccg agttctggga ggacaacttc cactgcaagc tgagccgcca cgccctcaag   1140
aagggcagcc acgtcaagaa gtgcaccaac cgtgagcgaa ttgggcagga ttcagcttat   1200
gagcaggagg ggaaggtgca gtttgtgatc gatgccgtgt acgccatggg ccacgcgctg   1260
cacgccatgc accgtgacct gtgtccccgg cgcgtggggc tctgcccgcg catggaccct   1320
gtagatggca cccagctgct taagtacatc cgaaacgtca acttctcagg catcgcaggg   1380
aaccctgtga ccttcaatga gaatggagat gcgcctgggc gctatgacat ctaccaatac   1440
cagctgcgca acgattctgc cgagtacaag gtcattggct cctggactga ccacctgcac   1500
cttagaatag agcggatgca ctggccgggg agcgggcagc agctgccccg ctccatctgc   1560
agcctgccct gccaaccggg tgagcggaag aagacagtga agggcatgcc ttgctgctgg   1620
cactgcgagc cttgcacagg gtaccagtac caggtggacc gctacacctg taagacgtgt   1680
ccctatgaca tgcggcccac agagaaccgc acgggctgcc ggcccatccc catcatcaag   1740
cttgagtggg gctcgccctg ggcgtgctg ccctcttcc tggccgtggt gggcatcgct   1800
```

```
gccacgttgt tcgtggtgat cacctttgtg cgctacaacg acacgcccat cgtcaaggcc    1860
tcgggccgtg aactgagcta cgtgctgctg gcaggcatct tcctgtgcta tgccaccacc    1920
ttcctcatga tcgctgagcc cgaccttggc acctgctcgc tgcgccgaat cttcctggga    1980
ctagggatga gcatcagcta tgcagccctg ctcaccaaga ccaaccgcat ctaccgcatc    2040
ttcgagcagg gcaagcgctc ggtcagtgcc ccacgcttca tcagcccgc ctcacagctg     2100 gccatcacct tcagcctcat ctcgctgcag ctgctgggca tctgtgtgtg gtttgtggtg    2160 gaccctccc actcggtggt ggacttccag gaccagcgga cactcgaccc ccgcttcgcc      2220 agggtgtgc tcaagtgtga catctcggac ctgtcgctca tctgcctgct gggctacagc     2280
atgctgctca tggtcacgtg caccgtgtat gccatcaaga cacgcggcgt gcccgagacc    2340
ttcaatgagg ccaagcccat tggcttcacc atgtacacca cttgcatcgt ctggctggcc    2400
ttcatcccca tcttctttgg cacctcgcag tcggccgaca agctgtacat ccagacgacg    2460
acgctgacgg tctcggtgag tctgagcgcc tcggtgtccc tgggaatgct ctacatgccc    2520
aaagtctaca tcatcctctt ccacccggag cagaacgtgc ccaagcgcaa gcgcagcctc    2580
aaagccgtcg ttacggcggc caccatgtcc aacaagttca cgcagaaggg caacttccgg    2640
cccaacggag aggccaagtc tgagctctgc gagaaccttg aggccccagc gctggccacc    2700
aaacagactt acgtcactta caccaaccat gcaatctag                            2739
```

<210> SEQ ID NO 12
<211> LENGTH: 900
<212> TYPE: PRT
<213> ORGANISM: homo sapiens

<400> SEQUENCE: 12

```
Met Pro Gly Lys Arg Gly Leu Gly Trp Trp Ala Arg Leu Pro Leu
1               5                   10                  15

Cys Leu Leu Leu Ser Leu Tyr Gly Pro Trp Met Pro Ser Ser Leu Gly
            20                  25                  30

Lys Pro Lys Gly His Pro His Met Asn Ser Ile Arg Ile Asp Gly Asp
        35                  40                  45

Ile Thr Leu Gly Gly Leu Phe Pro Val His Gly Arg Gly Ser Glu Gly
    50                  55                  60

Lys Pro Cys Gly Glu Leu Lys Lys Glu Lys Gly Ile His Arg Leu Glu
65                  70                  75                  80

Ala Met Leu Phe Ala Leu Asp Arg Ile Asn Asn Asp Pro Asp Leu Leu
                85                  90                  95

Pro Asn Ile Thr Leu Gly Ala Arg Ile Leu Asp Thr Cys Ser Arg Asp
            100                 105                 110

Thr His Ala Leu Glu Gln Ser Leu Thr Phe Val Gln Ala Leu Ile Glu
        115                 120                 125

Lys Asp Gly Thr Glu Val Arg Cys Gly Ser Gly Gly Pro Pro Ile Ile
    130                 135                 140

Thr Lys Pro Glu Arg Val Val Gly Val Ile Ala Ser Gly Ser Ser
145                 150                 155                 160

Val Ser Ile Met Val Ala Asn Ile Leu Arg Leu Phe Lys Ile Pro Gln
                165                 170                 175

Ile Ser Tyr Ala Ser Thr Ala Pro Asp Leu Ser Asp Asn Ser Arg Tyr
            180                 185                 190

Asp Phe Phe Ser Arg Val Val Pro Ser Asp Thr Tyr Gln Ala Gln Ala
        195                 200                 205
```

Met Val Asp Ile Val Arg Ala Leu Lys Trp Asn Tyr Val Ser Thr Val
210                 215                 220

Ala Ser Glu Gly Ser Tyr Gly Glu Ser Gly Val Glu Ala Phe Ile Gln
225                 230                 235                 240

Lys Ser Arg Glu Asp Gly Gly Val Cys Ile Ala Gln Ser Val Lys Ile
            245                 250                 255

Pro Arg Glu Pro Lys Ala Gly Glu Phe Asp Lys Ile Ile Arg Arg Leu
        260                 265                 270

Leu Glu Thr Ser Asn Ala Arg Ala Val Ile Ile Phe Ala Asn Glu Asp
            275                 280                 285

Asp Ile Arg Arg Val Leu Glu Ala Ala Arg Arg Ala Asn Gln Thr Gly
290                 295                 300

His Phe Phe Trp Met Gly Ser Asp Ser Trp Gly Ser Lys Ile Ala Pro
305                 310                 315                 320

Val Leu His Leu Glu Glu Val Ala Glu Gly Ala Val Thr Ile Leu Pro
            325                 330                 335

Lys Arg Met Ser Val Arg Gly Phe Asp Arg Tyr Phe Ser Ser Arg Thr
        340                 345                 350

Leu Asp Asn Asn Arg Arg Asn Ile Trp Phe Ala Glu Phe Trp Glu Asp
            355                 360                 365

Asn Phe His Cys Lys Leu Ser Arg His Ala Leu Lys Lys Gly Ser His
370                 375                 380

Val Lys Lys Cys Thr Asn Arg Glu Arg Ile Gly Gln Asp Ser Ala Tyr
385                 390                 395                 400

Glu Gln Glu Gly Lys Val Gln Phe Val Ile Asp Ala Val Tyr Ala Met
            405                 410                 415

Gly His Ala Leu His Ala Met His Arg Asp Leu Cys Pro Gly Arg Val
        420                 425                 430

Gly Leu Cys Pro Arg Met Asp Pro Val Asp Gly Thr Gln Leu Leu Lys
            435                 440                 445

Tyr Ile Arg Asn Val Asn Phe Ser Gly Ile Ala Gly Asn Pro Val Thr
450                 455                 460

Phe Asn Glu Asn Gly Asp Ala Pro Gly Arg Tyr Asp Ile Tyr Gln Tyr
465                 470                 475                 480

Gln Leu Arg Asn Asp Ser Ala Glu Tyr Lys Val Ile Gly Ser Trp Thr
            485                 490                 495

Asp His Leu His Leu Arg Ile Glu Arg Met His Trp Pro Gly Ser Gly
        500                 505                 510

Gln Gln Leu Pro Arg Ser Ile Cys Ser Leu Pro Cys Gln Pro Gly Glu
            515                 520                 525

Arg Lys Lys Thr Val Lys Gly Met Pro Cys Cys Trp His Cys Glu Pro
530                 535                 540

Cys Thr Gly Tyr Gln Tyr Gln Val Asp Arg Tyr Thr Cys Lys Thr Cys
545                 550                 555                 560

Pro Tyr Asp Met Arg Pro Thr Glu Asn Arg Thr Gly Cys Arg Pro Ile
            565                 570                 575

Pro Ile Ile Lys Leu Glu Trp Gly Ser Pro Trp Ala Val Leu Pro Leu
        580                 585                 590

Phe Leu Ala Val Val Gly Ile Ala Ala Thr Leu Phe Val Ile Thr
            595                 600                 605

Phe Val Arg Tyr Asn Asp Thr Pro Ile Val Lys Ala Ser Gly Arg Glu
610                 615                 620

Leu Ser Tyr Val Leu Leu Ala Gly Ile Phe Leu Cys Tyr Ala Thr Thr

```
                625             630             635             640
        Phe Leu Met Ile Ala Glu Pro Asp Leu Gly Thr Cys Ser Leu Arg Arg
                        645             650             655

Ile Phe Leu Gly Leu Gly Met Ser Ile Ser Tyr Ala Ala Leu Leu Thr
                        660             665             670

Lys Thr Asn Arg Ile Tyr Arg Ile Phe Glu Gln Gly Lys Arg Ser Val
                        675             680             685

Ser Ala Pro Arg Phe Ile Ser Pro Ala Ser Gln Leu Ala Ile Thr Phe
                        690             695             700

Ser Leu Ile Ser Leu Gln Leu Leu Gly Ile Cys Val Trp Phe Val Val
        705             710             715             720

Asp Pro Ser His Ser Val Val Asp Phe Gln Asp Gln Arg Thr Leu Asp
                        725             730             735

Pro Arg Phe Ala Arg Gly Val Leu Lys Cys Asp Ile Ser Asp Leu Ser
                        740             745             750

Leu Ile Cys Leu Leu Gly Tyr Ser Met Leu Leu Met Val Thr Cys Thr
                        755             760             765

Val Tyr Ala Ile Lys Thr Arg Gly Val Pro Glu Thr Phe Asn Glu Ala
                        770             775             780

Lys Pro Ile Gly Phe Thr Met Tyr Thr Thr Cys Ile Val Trp Leu Ala
        785             790             795             800

Phe Ile Pro Ile Phe Phe Gly Thr Ser Gln Ser Ala Asp Lys Leu Tyr
                        805             810             815

Ile Gln Thr Thr Thr Leu Thr Val Ser Val Ser Leu Ser Ala Ser Val
                        820             825             830

Ser Leu Gly Met Leu Tyr Met Pro Lys Val Tyr Ile Ile Leu Phe His
                        835             840             845

Pro Glu Gln Asn Val Pro Lys Arg Lys Arg Ser Leu Lys Ala Val Val
                        850             855             860

Thr Ala Ala Thr Met Ser Asn Lys Phe Thr Gln Lys Gly Asn Phe Arg
        865             870             875             880

Pro Asn Gly Glu Ala Lys Ser Glu Leu Cys Glu Asn Leu Glu Ala Pro
                        885             890             895

Ala Leu Ala Thr
                        900

<210> SEQ ID NO 13
<211> LENGTH: 1123
<212> TYPE: DNA
<213> ORGANISM: homo sapiens

<400> SEQUENCE: 13
atgcgcgcgg gcagcgggcg acgcgccctt gcgcagcctg agcaagcca  accgcacccg      60 ctttcccttc ttctccgacg tcaagggcga ccaccggctg gtgctggccg cggtggagac     120
aaccgtgctg gtgctcatct ttgcagtgtc gctgctgggc aacgtgtgcg ccctggtgct     180
ggtggcgcgc cgacgacgcc gcggcgcgac tgcctgcctg gtactcaacc tcttctgcgc     240
ggacctgctc ttcatcagcg ctatccctct ggtgctggcc gtgcgctgga ctgaggcctg     300
gctgctgggc cccgttgcct gccacctgct cttctacgtg atgaccctga gcggcagcgt     360
caccatcctc acgctggccg cggtcagcct ggagcgcatg gtgtgcatcg tgcacctgca     420
gcgcggcgtg cggggtcctg gcggcgggc gcgggcagtg ctgctggcgc tcatctgggg     480
ctattcggcg gtcgccgctc tgcctctctg cgtcttcttc cgagtcgtcc cgcaacggct     540
```

```
ccccggcgcc gaccaggaaa tttcgatttg cacactgatt tggcccacca ttcctggaga      600
gatctcgtgg gatgtctctt ttgttacttt gaacttcttg gtgccaggac tggtcattgt      660
gatcagttac tccaaaattt tacagacctc ggaacacctc ctggatgcaa gagctgtcgt      720
gactcacagt gagatcacaa aggcatcaag gaagaggctc acggtaagcc tggcctactc      780
ggagagccac cagatccgcg tgtcccagca ggacttccgg ctcttccgca ccctcttcct      840
cctcatggtc tccttcttca tcatgtggag ccccatcatc atcaccatcc tcctcatcct      900
gatccagaac ttcaagcaag acctggtcat ctggccgtcc ctcttcttct gggtggtggc      960
cttcacattt gctaattcag ccctaaaccc catcctctac aacatgacac tgtgcaggaa     1020
tgagtggaag aaaatttttt gctgcttctg gttcccagaa aagggagcca ttttaacaga     1080
cacatctgtc aaaagaaatg acttgtcgat tatttctggc taa                       1123
```

<210> SEQ ID NO 14
<211> LENGTH: 377
<212> TYPE: PRT
<213> ORGANISM: homo sapiens

<400> SEQUENCE: 14

```
Met Ser Pro Glu Cys Ala Arg Ala Ala Gly Asp Ala Pro Leu Arg Ser
1               5                   10                  15

Leu Glu Gln Ala Asn Arg Thr Arg Phe Pro Phe Phe Ser Asp Val Lys
            20                  25                  30

Gly Asp His Arg Leu Val Leu Ala Ala Val Glu Thr Thr Val Leu Val
        35                  40                  45

Leu Ile Phe Ala Val Ser Leu Leu Gly Asn Val Cys Ala Leu Val Leu
    50                  55                  60

Val Ala Arg Arg Arg Arg Gly Ala Thr Ala Cys Leu Val Leu Asn
65                  70                  75                  80

Leu Phe Cys Ala Asp Leu Leu Phe Ile Ser Ala Ile Pro Leu Val Leu
                85                  90                  95

Ala Val Arg Trp Thr Glu Ala Trp Leu Leu Gly Pro Val Ala Cys His
            100                 105                 110

Leu Leu Phe Tyr Val Met Thr Leu Ser Gly Ser Val Thr Ile Leu Thr
        115                 120                 125

Leu Ala Ala Val Ser Leu Glu Arg Met Val Cys Ile Val His Leu Gln
    130                 135                 140

Arg Gly Val Arg Gly Pro Gly Arg Arg Ala Arg Ala Val Leu Leu Ala
145                 150                 155                 160

Leu Ile Trp Gly Tyr Ser Ala Val Ala Ala Leu Pro Leu Cys Val Phe
                165                 170                 175

Phe Arg Val Val Pro Gln Arg Leu Pro Gly Ala Asp Gln Glu Ile Ser
            180                 185                 190

Ile Cys Thr Leu Ile Trp Pro Thr Ile Pro Gly Glu Ile Ser Trp Asp
        195                 200                 205

Val Ser Phe Val Thr Leu Asn Phe Leu Val Pro Gly Leu Val Ile Val
    210                 215                 220

Ile Ser Tyr Ser Lys Ile Leu Gln Thr Ser Glu His Leu Leu Asp Ala
225                 230                 235                 240

Arg Ala Val Val Thr His Ser Glu Ile Thr Lys Ala Ser Arg Lys Arg
                245                 250                 255

Leu Thr Val Ser Leu Ala Tyr Ser Glu Ser His Gln Ile Arg Val Ser
            260                 265                 270
```

```
Gln Gln Asp Phe Arg Leu Phe Arg Thr Leu Phe Leu Leu Met Val Ser
            275                 280                 285

Phe Phe Ile Met Trp Ser Pro Ile Ile Ile Thr Ile Leu Leu Ile Leu
290                 295                 300

Ile Gln Asn Phe Lys Gln Asp Leu Val Ile Trp Pro Ser Leu Phe Phe
305                 310                 315                 320

Trp Val Val Ala Phe Thr Phe Ala Asn Ser Ala Leu Asn Pro Ile Leu
                325                 330                 335

Tyr Asn Met Thr Leu Cys Arg Asn Glu Trp Lys Lys Ile Phe Cys Cys
            340                 345                 350

Phe Trp Phe Pro Glu Lys Gly Ala Ile Leu Thr Asp Thr Ser Val Lys
            355                 360                 365

Arg Asn Asp Leu Ser Ile Ile Ser Gly
    370                 375

<210> SEQ ID NO 15
<211> LENGTH: 1119
<212> TYPE: DNA
<213> ORGANISM: homo sapiens

<400> SEQUENCE: 15
atgttagcca acagctcctc aaccaacagt tctgttctcc cgtgtcctga ctaccgacct       60
acccaccgcc tgcacttggt ggtctacagc ttggtgctgg ctgccgggct ccccctcaac      120
gcgctagccc tctgggtctt cctgcgcgcg ctgcgcgtgc actcggtggt gagcgtgtac      180
atgtgtaacc tggcggccag cgacctgctc ttcaccctct cgctgcccgt tcgtctctcc      240
tactacgcac tgcaccactg gcccttcccc gacctcctgt gccagacgac gggcgccatc      300
ttccagatga acatgtacgg cagctgcatc ttcctgatgc tcatcaacgt ggaccgctac      360
gccgccatcg tgcacccgct cgactgcgc cacctgcggc ggccccgcgt ggcgcggctg      420
ctctgcctgg gcgtgtgggc gctcatcctg tgtttgccg tgcccgccgc ccgcgtgcac       480
aggccctcgc gttgccgcta ccgggacctc gaggtgcgcc tatgcttcga gagcttcagc      540
gacgagctgt ggaaaggcag gctgctgccc ctcgtgctgc tggccgaggc gctgggcttc      600
ctgctgcccc tggcggcggt ggtctactcg tcgggccgag tcttctggac gctggcgcgc      660
cccgacgcca cgcagagcca gcggcggcgg aagaccgtgc gcctcctgct ggctaacctc      720
gtcatcttcc tgctgtgctt cgtgcccac aacagcacgc tggcggtcta cgggctgctg      780
cggagcaagc tggtggcggc cagcgtgcct gcccgcgatc gcgtgcgcgg ggtgctgatg      840
gtgatggtgc tgctggccgg cgccaactgc gtgctggacc gctggtgta ctactttagc      900 gccgagggct ccgcaacac cctgcgcggc ctgggcactc cgcaccgggc caggacctcg      960
gccaccaacg gacgcgggc ggcgctcgcg caatccgaaa ggtccgccgt caccaccgac     1020
gccaccaggc cggatgccgc cagtcagggg ctgctccgac cctccgactc ccactctctg     1080
tcttccttca cacagtgtcc ccaggattcc gccctctga                            1119

<210> SEQ ID NO 16
<211> LENGTH: 372
<212> TYPE: PRT
<213> ORGANISM: homo sapiens

<400> SEQUENCE: 16

Met Leu Ala Asn Ser Ser Ser Thr Asn Ser Ser Val Leu Pro Cys Pro
1               5                   10                  15

Asp Tyr Arg Pro Thr His Arg Leu His Leu Val Val Tyr Ser Leu Val
```

```
                        20                  25                  30
Leu Ala Ala Gly Leu Pro Leu Asn Ala Leu Ala Leu Trp Val Phe Leu
             35                  40                  45
Arg Ala Leu Arg Val His Ser Val Val Ser Val Tyr Met Cys Asn Leu
     50                  55                  60
Ala Ala Ser Asp Leu Leu Phe Thr Leu Ser Leu Pro Val Arg Leu Ser
 65                  70                  75                  80
Tyr Tyr Ala Leu His His Trp Pro Phe Pro Asp Leu Leu Cys Gln Thr
                 85                  90                  95
Thr Gly Ala Ile Phe Gln Met Asn Met Tyr Gly Ser Cys Ile Phe Leu
            100                 105                 110
Met Leu Ile Asn Val Asp Arg Tyr Ala Ala Ile Val His Pro Leu Arg
        115                 120                 125
Leu Arg His Leu Arg Arg Pro Arg Val Ala Arg Leu Leu Cys Leu Gly
    130                 135                 140
Val Trp Ala Leu Ile Leu Val Phe Ala Val Pro Ala Ala Arg Val His
145                 150                 155                 160
Arg Pro Ser Arg Cys Arg Tyr Arg Asp Leu Glu Val Arg Leu Cys Phe
                165                 170                 175
Glu Ser Phe Ser Asp Glu Leu Trp Lys Gly Arg Leu Leu Pro Leu Val
            180                 185                 190
Leu Leu Ala Glu Ala Leu Gly Phe Leu Leu Pro Leu Ala Ala Val Val
        195                 200                 205
Tyr Ser Ser Gly Arg Val Phe Trp Thr Leu Ala Arg Pro Asp Ala Thr
    210                 215                 220
Gln Ser Gln Arg Arg Arg Lys Thr Val Arg Leu Leu Leu Ala Asn Leu
225                 230                 235                 240
Val Ile Phe Leu Leu Cys Phe Val Pro Tyr Asn Ser Thr Leu Ala Val
                245                 250                 255
Tyr Gly Leu Leu Arg Ser Lys Leu Val Ala Ala Ser Val Pro Ala Arg
            260                 265                 270
Asp Arg Val Arg Gly Val Leu Met Val Met Val Leu Leu Ala Gly Ala
        275                 280                 285
Asn Cys Val Leu Asp Pro Leu Val Tyr Tyr Phe Ser Ala Glu Gly Phe
    290                 295                 300
Arg Asn Thr Leu Arg Gly Leu Gly Thr Pro His Arg Ala Arg Thr Ser
305                 310                 315                 320
Ala Thr Asn Gly Thr Arg Ala Ala Leu Ala Gln Ser Glu Arg Ser Ala
                325                 330                 335
Val Thr Thr Asp Ala Thr Arg Pro Asp Ala Ala Ser Gln Gly Leu Leu
            340                 345                 350
Arg Pro Ser Asp Ser His Ser Leu Ser Ser Phe Thr Gln Cys Pro Gln
        355                 360                 365
Asp Ser Ala Leu
    370

<210> SEQ ID NO 17
<211> LENGTH: 903
<212> TYPE: DNA
<213> ORGANISM: homo sapiens

<400> SEQUENCE: 17
atggacctgc cccgcagct ctccttcggc ctctatgtgg ccgcctttgc gctgggcttc      60
ccgctcaacg tcctggccat ccgaggcgcg acggcccacg cccggctccg tctcacccct    120
```

```
agcctggtct acgccctgaa cctgggctgc tccgacctgc tgctgacagt ctctctgccc    180
ctgaaggcgg tggaggcgct agcctccggg gcctggcctc tgccggcctc gctgtgcccc    240
gtcttcgcgg tggcccactt cttcccactc tatgccggcg ggggcttcct ggccgccctg    300
agtgcaggcc gctacctggg agcagccttc cccttgggct accaagcctt ccggaggccg    360
tgctattcct ggggggtgtg cgcggccatc tgggccctcg tcctgtgtca cctgggtctg    420
gtctttgggt tggaggctcc aggaggctgg ctggaccaca gcaacacctc cctgggcatc    480
aacacaccgg tcaacggctc tccggtctgc ctggaggcct gggacccggc tctgccggc     540
ccggcccgct tcagcctctc tctcctgctc ttttttctgc ccttggccat cacagccttc    600
tgctacgtgg gctgcctccg ggcactggcc cgctccggcc tgacgcacag cggaagctg     660
cgggccgcct gggtggccgg cggggccctc ctcacgctgc tgctctgcgt aggaccctac    720
aacgcctcca acgtggccag cttcctgtac cccaatctag gaggctcctg gcggaagctg    780
gggctcatca cggtgcctg gagtgtgtg cttaatccgc tggtgaccgg ttacttggga     840
aggggtcctg gcctgaagac agtgtgtgcg gcaagaacgc aagggggcaa gtcccagaag    900
taa                                                                  903

<210> SEQ ID NO 18
<211> LENGTH: 300
<212> TYPE: PRT
<213> ORGANISM: homo sapiens

<400> SEQUENCE: 18

Met Asp Leu Pro Pro Gln Leu Ser Phe Gly Leu Tyr Val Ala Ala Phe
1               5                   10                  15

Ala Leu Gly Phe Pro Leu Asn Val Leu Ala Ile Arg Gly Ala Thr Ala
            20                  25                  30

His Ala Arg Leu Arg Leu Thr Pro Ser Leu Val Tyr Ala Leu Asn Leu
        35                  40                  45

Gly Cys Ser Asp Leu Leu Leu Thr Val Ser Leu Pro Leu Lys Ala Val
    50                  55                  60

Glu Ala Leu Ala Ser Gly Ala Trp Pro Leu Pro Ala Ser Leu Cys Pro
65                  70                  75                  80

Val Phe Ala Val Ala His Phe Phe Pro Leu Tyr Ala Gly Gly Gly Phe
                85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

Ala Ile Trp Ala Leu Val Leu Cys His Leu Gly Leu Val Phe Gly Leu
    130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Phe Phe
            180                 185                 190

Leu Pro Leu Ala Ile Thr Ala Phe Cys Tyr Val Gly Cys Leu Arg Ala
        195                 200                 205

Leu Ala Arg Ser Gly Leu Thr His Arg Arg Lys Leu Arg Ala Ala Trp
    210                 215                 220
```

Val Ala Gly Gly Ala Leu Leu Thr Leu Leu Leu Cys Val Gly Pro Tyr
225                 230                 235                 240

Asn Ala Ser Asn Val Ala Ser Phe Leu Tyr Pro Asn Leu Gly Ser
            245                 250                 255

Trp Arg Lys Leu Gly Leu Ile Thr Gly Ala Trp Ser Val Val Leu Asn
        260                 265                 270

Pro Leu Val Thr Gly Tyr Leu Gly Arg Gly Pro Gly Leu Lys Thr Val
            275                 280                 285

Cys Ala Ala Arg Thr Gln Gly Gly Lys Ser Gln Lys
        290                 295                 300

<210> SEQ ID NO 19
<211> LENGTH: 993
<212> TYPE: DNA
<213> ORGANISM: homo sapiens

<400> SEQUENCE: 19
atgctgccgg actggaagag ctccttgatc tcatggctt acatcatcat cttcctcact      60
ggcctccctg ccaacctcct ggccctgcgg gcctttgtgg ggcggatccg ccagccccag    120
cctgcacctg tgcacatcct cctgctgagc ctgacgctgg ccgacctcct cctgctgctg    180
ctgctgccct tcaagatcat cgaggctgcg tcgaacttcc gctggtacct gcccaaggtc    240
gtctgcgccc tcacgagttt tggcttctac agcagcatct actgcagcac gtggctcctg    300
gcgggcatca gcatcgagcg ctacctggga gtggctttcc ccgtgcagta caagctctcc    360
cgccggcctc tgtatggagt gattgcagct ctggtggcct gggttatgtc ctttggtcac    420
tgcaccatcg tgatcatcgt tcaatacttg aacacgactg agcaggtcag aagtggcaat    480
gaaattacct gctacgagaa cttcaccgat aaccagttgg acgtggtgct gcccgtgcgg    540
ctggagctgt gcctggtgct cttcttcatc cccatggcag tcaccatctt ctgctactgg    600
cgttttgtgt ggatcatgct ctcccagccc cttgtgggg cccagaggcg cgccgagcc    660
gtggggctgg ctgtggtgac gctgctcaat ttcctggtgt gcttcggacc ttacaacgtg    720
tcccacctgg tggggtatca ccagagaaaa agccctggt ggcggtcaat agccgtggtg    780
ttcagttcac tcaacgccag tctggacccc ctgctcttct atttctcttc ttcagtggtg    840
cgcagggcat tgggagaggg ctgcaggtg ctgcggaatc agggctcctc cctgttggga    900
cgcagaggca aagacacagc agaggggaca aatgaggaca ggggtgtggg tcaaggagaa    960
gggatgccaa gttcggactt cactacagag tag                                 993

<210> SEQ ID NO 20
<211> LENGTH: 330
<212> TYPE: PRT
<213> ORGANISM: homo sapiens

<400> SEQUENCE: 20

Met Leu Pro Asp Trp Lys Ser Ser Leu Ile Leu Met Ala Tyr Ile Ile
1               5                   10                  15

Ile Phe Leu Thr Gly Leu Pro Ala Asn Leu Leu Ala Leu Arg Ala Phe
            20                  25                  30

Val Gly Arg Ile Arg Gln Pro Gln Pro Ala Pro Val His Ile Leu Leu
        35                  40                  45

Leu Ser Leu Thr Leu Ala Asp Leu Leu Leu Leu Leu Leu Pro Phe
    50                  55                  60

Lys Ile Ile Glu Ala Ala Ser Asn Phe Arg Trp Tyr Leu Pro Lys Val
65                  70                  75                  80

Val Cys Ala Leu Thr Ser Phe Gly Phe Tyr Ser Ser Ile Tyr Cys Ser
                85                  90                  95

Thr Trp Leu Leu Ala Gly Ile Ser Ile Glu Arg Tyr Leu Gly Val Ala
        100                 105                 110

Phe Pro Val Gln Tyr Lys Leu Ser Arg Arg Pro Leu Tyr Gly Val Ile
        115                 120                 125

Ala Ala Leu Val Ala Trp Val Met Ser Phe Gly His Cys Thr Ile Val
130                 135                 140

Ile Ile Val Gln Tyr Leu Asn Thr Thr Glu Gln Val Arg Ser Gly Asn
145                 150                 155                 160

Glu Ile Thr Cys Tyr Glu Asn Phe Thr Asp Asn Gln Leu Asp Val Val
                165                 170                 175

Leu Pro Val Arg Leu Glu Leu Cys Leu Val Leu Phe Phe Ile Pro Met
        180                 185                 190

Ala Val Thr Ile Phe Cys Tyr Trp Arg Phe Val Trp Ile Met Leu Ser
        195                 200                 205

Gln Pro Leu Val Gly Ala Gln Arg Arg Arg Arg Ala Val Gly Leu Ala
210                 215                 220

Val Val Thr Leu Leu Asn Phe Leu Val Cys Phe Gly Pro Tyr Asn Val
225                 230                 235                 240

Ser His Leu Val Gly Tyr His Gln Arg Lys Ser Pro Trp Trp Arg Ser
                245                 250                 255

Ile Ala Val Val Phe Ser Ser Leu Asn Ala Ser Leu Asp Pro Leu Leu
        260                 265                 270

Phe Tyr Phe Ser Ser Ser Val Val Arg Arg Ala Phe Gly Arg Gly Leu
        275                 280                 285

Gln Val Leu Arg Asn Gln Gly Ser Ser Leu Leu Gly Arg Arg Gly Lys
        290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330

<210> SEQ ID NO 21
<211> LENGTH: 1041
<212> TYPE: DNA
<213> ORGANISM: homo sapiens

<400> SEQUENCE: 21
atggatacag gccccgacca gtcctacttc tccggcaatc actggttcgt cttctcggtg     60
taccttctca ctttcctggt ggggctcccc ctcaacctgc tggccctggt ggtcttcgtg    120
ggcaagctgc agcgccgccc ggtggccgtg acgtgctcc tgctcaacct gaccgcctcg     180
gacctgctcc tgctgctgtt cctgcctttc gcatggtgg aggcagccaa tggcatgcac     240
tggcccctgc ccttcatcct ctgcccactc tctggattca tcttcttcac caccatctat    300
ctcaccgccc tcttcctggc agctgtgagc attgaacgct tcctgagtgt ggcccaccca    360
ctgtggtaca agaccccggcc gaggctgggg caggcaggtc tggtgagtgt ggcctgctgg    420
ctgttggcct ctgctcactg cagcgtggtc tacgtcatag aattctcagg gacatctcc     480 cacagccagg gcaccaatgg gacctgctac ctggagttcc ggaaggacca gctagccatc    540
ctcctgcccg tgcggctgga gatggctgtg gtcctctttg tggtcccgct gatcatcacc    600
agctactgct acagccgcct ggtgtggatc ctcggcagag ggggcagcca ccgccggcag    660

```
aggagggtgg cggggctgtt ggcggccacg ctgctcaact tccttgtctg ctttgggccc    720
tacaacgtgt cccatgtcgt gggctatatc tgcggtgaaa gcccggcgtg gaggatctac    780
gtgacgcttc tcagcaccct gaactcctgt gtcgacccct tgtctacta cttctcctcc    840 tccgggttcc aagccgactt tcatgagctg ctgaggaggt tgtgtgggct ctggggccag    900
tggcagcagg agagcagcat ggagctgaag gagcagaagg gagggagga gcagagagcg    960 gaccgaccag ctgaaagaaa gaccagtgaa cactcacagg gctgtggaac tggtggccag   1020
gtggcctgtg ctgaaagcta g                                             1041
```

<210> SEQ ID NO 22
<211> LENGTH: 346
<212> TYPE: PRT
<213> ORGANISM: homo sapiens

<400> SEQUENCE: 22

Met Asp Thr Gly Pro Asp Gln Ser Tyr Phe Ser Gly Asn His Trp Phe
1               5                   10                  15

Val Phe Ser Val Tyr Leu Leu Thr Phe Leu Val Gly Leu Pro Leu Asn
                20                  25                  30

Leu Leu Ala Leu Val Val Phe Val Gly Lys Leu Gln Arg Arg Pro Val
            35                  40                  45

Ala Val Asp Val Leu Leu Leu Asn Leu Thr Ala Ser Asp Leu Leu Leu
        50                  55                  60

Leu Leu Phe Leu Pro Phe Arg Met Val Glu Ala Ala Asn Gly Met His
65                  70                  75                  80

Trp Pro Leu Pro Phe Ile Leu Cys Pro Leu Ser Gly Phe Ile Phe Phe
                85                  90                  95

Thr Thr Ile Tyr Leu Thr Ala Leu Phe Leu Ala Ala Val Ser Ile Glu
            100                 105                 110

Arg Phe Leu Ser Val Ala His Pro Leu Trp Tyr Lys Thr Arg Pro Arg
        115                 120                 125

Leu Gly Gln Ala Gly Leu Val Ser Val Ala Cys Trp Leu Leu Ala Ser
    130                 135                 140

Ala His Cys Ser Val Val Tyr Val Ile Glu Phe Ser Gly Asp Ile Ser
145                 150                 155                 160

His Ser Gln Gly Thr Asn Gly Thr Cys Tyr Leu Glu Phe Arg Lys Asp
                165                 170                 175

Gln Leu Ala Ile Leu Leu Pro Val Arg Leu Glu Met Ala Val Val Leu
            180                 185                 190

Phe Val Val Pro Leu Ile Ile Thr Ser Tyr Cys Tyr Ser Arg Leu Val
        195                 200                 205

Trp Ile Leu Gly Arg Gly Gly Ser His Arg Arg Gln Arg Arg Val Ala
    210                 215                 220

Gly Leu Leu Ala Ala Thr Leu Leu Asn Phe Leu Val Cys Phe Gly Pro
225                 230                 235                 240

Tyr Asn Val Ser His Val Val Gly Tyr Ile Cys Gly Glu Ser Pro Ala
                245                 250                 255

Trp Arg Ile Tyr Val Thr Leu Leu Ser Thr Leu Asn Ser Cys Val Asp
            260                 265                 270

Pro Phe Val Tyr Tyr Phe Ser Ser Gly Phe Gln Ala Asp Phe His
        275                 280                 285

Glu Leu Leu Arg Arg Leu Cys Gly Leu Trp Gly Gln Trp Gln Gln Glu
    290                 295                 300

Ser Ser Met Glu Leu Lys Glu Gln Lys Gly Glu Glu Gln Arg Ala
305                 310                 315                 320

Asp Arg Pro Ala Glu Arg Lys Thr Ser Glu His Ser Gln Gly Cys Gly
                325                 330                 335

Thr Gly Gly Gln Val Ala Cys Ala Glu Ser
            340                 345

<210> SEQ ID NO 23
<211> LENGTH: 1191
<212> TYPE: DNA
<213> ORGANISM: homo sapiens

<400> SEQUENCE: 23
atgtggaaca gctctgacgc caacttctcc tgctaccatg agtctgtgct gggctatcgt      60
tatgttgcag ttagctgggg ggtggtggtg gctgtgacag gcaccgtggg caatgtgctc     120
accctactgg ccttggccat ccagcccaag ctccgtaccc gattcaacct gctcatagcc     180
aacctcacac tggctgatct cctctactgc acgctccttc agcccttctc tgtggacacc     240
tacctccacc tgcactggcg caccggtgcc accttctgca gggtatttgg gctcctcctt     300
tttgcctcca attctgtctc catcctgacc ctctgcctca tcgcactggg acgctacctc     360
ctcattgccc accctaagct tttcccccaa gttttcagtg ccaaggggat agtgctggca     420
ctggtgagca cctgggttgt gggcgtggcc agctttgctc ccctctggcc tatttatatc     480
ctggtacctg tagtctgcac ctgcagcttt gaccgcatcc gaggccggcc ttacaccacc     540
atcctcatgg gcatctactt tgtgcttggg ctcagcagtg ttggcatctt ctattgcctc     600
atccaccgcc aggtcaaacg agcagcacag gcactggacc aatacaagtt gcgacaggca     660
agcatccact ccaaccatgt ggccaggact gatgaggcca tgcctggtcg tttccaggag     720
ctggacagca ggttagcatc aggaggaccc agtgagggga tttcatctga ccagtcagt      780 gctgccacca cccagaccct ggaagggac tcatcagaag tgggagacca gatcaacagc      840
aagagagcta agcagatggc agagaaaagc cctccagaag catctgccaa agcccagcca     900
attaaaggag ccagaagagc tccggattct tcatcggaat tgggaaggt gactcgaatg      960 tgttttgctg tgttcctctg ctttgccctg agctacatcc ccttcttgct gctcaacatt    1020
ctggatgcca gagtccaggc tccccgggtg gtccacatgc ttgctgccaa cctcacctgg    1080
ctcaatggtt gcatcaaccc tgtgctctat gcagccatga accgccaatt ccgccaagca    1140
tatggctcca ttttaaaaag agggcccggg agtttccata ggctccatta g             1191

<210> SEQ ID NO 24
<211> LENGTH: 396
<212> TYPE: PRT
<213> ORGANISM: homo sapiens

<400> SEQUENCE: 24

Met Trp Asn Ser Ser Asp Ala Asn Phe Ser Cys Tyr His Glu Ser Val
1               5                   10                  15

Leu Gly Tyr Arg Tyr Val Ala Val Ser Trp Gly Val Val Val Ala Val
                20                  25                  30

Thr Gly Thr Val Gly Asn Val Leu Thr Leu Leu Ala Leu Ala Ile Gln
            35                  40                  45

Pro Lys Leu Arg Thr Arg Phe Asn Leu Leu Ile Ala Asn Leu Thr Leu
        50                  55                  60

Ala Asp Leu Leu Tyr Cys Thr Leu Leu Gln Pro Phe Ser Val Asp Thr
65                  70                  75                  80

```
Tyr Leu His Leu His Trp Arg Thr Gly Ala Thr Phe Cys Arg Val Phe
                     85                  90                  95

Gly Leu Leu Leu Phe Ala Ser Asn Ser Val Ser Ile Leu Thr Leu Cys
            100                 105                 110

Leu Ile Ala Leu Gly Arg Tyr Leu Leu Ile Ala His Pro Lys Leu Phe
        115                 120                 125

Pro Gln Val Phe Ser Ala Lys Gly Ile Val Leu Ala Leu Val Ser Thr
    130                 135                 140

Trp Val Val Gly Val Ala Ser Phe Ala Pro Leu Trp Pro Ile Tyr Ile
145                 150                 155                 160

Leu Val Pro Val Val Cys Thr Cys Ser Phe Asp Arg Ile Arg Gly Arg
                165                 170                 175

Pro Tyr Thr Thr Ile Leu Met Gly Ile Tyr Phe Val Leu Gly Leu Ser
            180                 185                 190

Ser Val Gly Ile Phe Tyr Cys Leu Ile His Arg Gln Val Lys Arg Ala
        195                 200                 205

Ala Gln Ala Leu Asp Gln Tyr Lys Leu Arg Gln Ala Ser Ile His Ser
    210                 215                 220

Asn His Val Ala Arg Thr Asp Glu Ala Met Pro Gly Arg Phe Gln Glu
225                 230                 235                 240

Leu Asp Ser Arg Leu Ala Ser Gly Gly Pro Ser Glu Gly Ile Ser Ser
                245                 250                 255

Glu Pro Val Ser Ala Ala Thr Thr Gln Thr Leu Glu Gly Asp Ser Ser
            260                 265                 270

Glu Val Gly Asp Gln Ile Asn Ser Lys Arg Ala Lys Gln Met Ala Glu
        275                 280                 285

Lys Ser Pro Pro Glu Ala Ser Ala Lys Ala Gln Pro Ile Lys Gly Ala
    290                 295                 300

Arg Arg Ala Pro Asp Ser Ser Glu Phe Gly Lys Val Thr Arg Met
305                 310                 315                 320

Cys Phe Ala Val Phe Leu Cys Phe Ala Leu Ser Tyr Ile Pro Phe Leu
                325                 330                 335

Leu Leu Asn Ile Leu Asp Ala Arg Val Gln Ala Pro Arg Val Val His
            340                 345                 350

Met Leu Ala Ala Asn Leu Thr Trp Leu Asn Gly Cys Ile Asn Pro Val
        355                 360                 365

Leu Tyr Ala Ala Met Asn Arg Gln Phe Arg Gln Ala Tyr Gly Ser Ile
    370                 375                 380

Leu Lys Arg Gly Pro Arg Ser Phe His Arg Leu His
385                 390                 395
```

<210> SEQ ID NO 25
<211> LENGTH: 1865
<212> TYPE: DNA
<213> ORGANISM: homo sapiens

<400> SEQUENCE: 25

```
atgggctctg acagctgggg ctccaagatt gcacctgtgc tgcacctgga ggaggtggct      60
gagggtgctg tcacgatcct ccccaagagg atgtccgtac gaggcttcga ccgctacttc     120
tccagccgca cgctggacaa caaccggcgc aacatctggt ttgccgagtt ctgggaggac     180
aacttccact gcaagctgag ccgccacgcc ctcaagaagg cagccacgt caagaagtgc     240 accaaccgtg agcgaattgg gcaggattca gcttatgagc aggaggggaa ggtgcagttt     300
```

```
gtgatcgatg ccgtgtacgc catgggccac gcgctgcacg ccatgcaccg tgacctgtgt    360
cccggccgcg tggggctctg cccgcgcatg gaccctgtag atggcaccca gctgcttaag    420
tacatccgaa acgtcaactt ctcaggcatc gcagggaacc ctgtgacctt caatgagaat    480
ggagatgcgc ctgggcgcta tgacatctac caataccagc tgcgcaacga ttctgccgag    540
tacaaggtca ttggctcctg gactgaccac ctgcaccttg aatagagcg gatgcactgg    600
ccggggagcg ggcagcagct gccccgctcc atctgcagcc tgccctgcca accgggtgag    660
cggaagaaga cagtgaaggg catgccttgc tgctggcact gcgagccttg cacagggtac    720
cagtaccagg tggaccgcta cacctgtaag acgtgtccct atgacatgcg cccacagag    780
aaccgcacgg gctgccggcc catccccatc atcaagcttg agtggggctc gccctgggcc    840
gtgctgcccc tcttcctggc cgtggtgggc atcgctgcca cgttgttcgt ggtgatcacc    900
tttgtgcgct acaacgacac gcccatcgtc aaggcctcgg ccgtgaact gagctacgtg    960
ctgctggcag gcatcttcct gtgctatgcc accaccttcc tcatgatcgc tgagcccgac   1020
cttggcacct gctcgctgcg ccgaatcttc ctgggactag ggatgagcat cagctatgca   1080
gccctgctca ccaagaccaa ccgcatctac cgcatcttcg agcagggcaa gcgctcggtc   1140
agtgccccac gcttcatcag ccccgcctca cagctggcca tcaccttcag cctcatctcg   1200
ctgcagctgc tgggcatctg tgtgtggttt gtggtggacc cctcccactc ggtggtggac   1260
ttccaggacc agcggacact cgaccccgc ttcgccaggg gtgtgctcaa gtgtgacatc   1320
tcggacctgt cgctcatctg cctgctgggc tacagcatgc tgctcatggt cacgtgcacc   1380
gtgtatgcca tcaagacacg cggcgtgccc gagaccttca atgaggccaa gcccattggc   1440
ttcaccatgt acaccacttg catcgtctgg ctggccttca tccccatctt ctttggcacc   1500
tcgcagtcgg ccgacaagct gtacatccag acgacgacgc tgacggtctc ggtgagtctg   1560
agcgcctcgg tgtccctggg aatgctctac atgcccaaag tctacatcat cctcttccac   1620
ccggagcaga acgtgcccaa gcgcaagcgc agcctcaaag ccgtcgttac ggcggccacc   1680
atgtccaaca gttcacgca aagggcaac ttccggccca acggagaggc caagtctgag   1740
ctctgcgaga accttgaggc cccagcgctg gccaccaaac agacttacgt cacttacacc   1800
aaccatgcaa tctagtctag agggcccgtt taaacccgct gatcagcctc gactgtgcct   1860
tctag                                                                1865
```

<210> SEQ ID NO 26
<211> LENGTH: 604
<212> TYPE: PRT
<213> ORGANISM: homo sapiens

<400> SEQUENCE: 26

Met Gly Ser Asp Ser Trp Gly Ser Lys Ile Ala Pro Val Leu His Leu
1               5                   10                  15

Glu Glu Val Ala Glu Gly Ala Val Thr Ile Leu Pro Lys Arg Met Ser
            20                  25                  30

Val Arg Gly Phe Asp Arg Tyr Phe Ser Ser Arg Thr Leu Asp Asn Asn
        35                  40                  45

Arg Arg Asn Ile Trp Phe Ala Glu Phe Trp Asp Asn Phe His Cys
    50                  55                  60

Lys Leu Ser Arg His Ala Leu Lys Lys Gly Ser His Val Lys Lys Cys
65                  70                  75                  80

Thr Asn Arg Glu Arg Ile Gly Gln Asp Ser Ala Tyr Glu Gln Glu Gly
                85                  90                  95

```
Lys Val Gln Phe Val Ile Asp Ala Val Tyr Ala Met Gly His Ala Leu
            100                 105                 110

His Ala Met His Arg Asp Leu Cys Pro Gly Arg Val Gly Leu Cys Pro
            115                 120                 125

Arg Met Asp Pro Val Asp Gly Thr Gln Leu Leu Lys Tyr Ile Arg Asn
            130                 135                 140

Val Asn Phe Ser Gly Ile Ala Gly Asn Pro Val Thr Phe Asn Glu Asn
145                 150                 155                 160

Gly Asp Ala Pro Gly Arg Tyr Asp Ile Tyr Gln Tyr Gln Leu Arg Asn
                165                 170                 175

Asp Ser Ala Glu Tyr Lys Val Ile Gly Ser Trp Thr Asp His Leu His
            180                 185                 190

Leu Arg Ile Glu Arg Met His Trp Pro Gly Ser Gly Gln Gln Leu Pro
            195                 200                 205

Arg Ser Ile Cys Ser Leu Pro Cys Gln Pro Gly Glu Arg Lys Lys Thr
            210                 215                 220

Val Lys Gly Met Pro Cys Cys Trp His Cys Glu Pro Cys Thr Gly Tyr
225                 230                 235                 240

Gln Tyr Gln Val Asp Arg Tyr Thr Cys Lys Thr Cys Pro Tyr Asp Met
                245                 250                 255

Arg Pro Thr Glu Asn Arg Thr Gly Cys Arg Pro Ile Pro Ile Ile Lys
            260                 265                 270

Leu Glu Trp Gly Ser Pro Trp Ala Val Leu Pro Leu Phe Leu Ala Val
            275                 280                 285

Val Gly Ile Ala Ala Thr Leu Phe Val Val Ile Thr Phe Val Arg Tyr
            290                 295                 300

Asn Asp Thr Pro Ile Val Lys Ala Ser Gly Arg Glu Leu Ser Tyr Val
305                 310                 315                 320

Leu Leu Ala Gly Ile Phe Leu Cys Tyr Ala Thr Thr Phe Leu Met Ile
                325                 330                 335

Ala Glu Pro Asp Leu Gly Thr Cys Ser Leu Arg Arg Ile Phe Leu Gly
            340                 345                 350

Leu Gly Met Ser Ile Ser Tyr Ala Ala Leu Leu Thr Lys Thr Asn Arg
            355                 360                 365

Ile Tyr Arg Ile Phe Glu Gln Gly Lys Arg Ser Val Ser Ala Pro Arg
            370                 375                 380

Phe Ile Ser Pro Ala Ser Gln Leu Ala Ile Thr Phe Ser Leu Ile Ser
385                 390                 395                 400

Leu Gln Leu Leu Gly Ile Cys Val Trp Phe Val Val Asp Pro Ser His
                405                 410                 415

Ser Val Val Asp Phe Gln Asp Gln Arg Thr Leu Asp Pro Arg Phe Ala
            420                 425                 430

Arg Gly Val Leu Lys Cys Asp Ile Ser Asp Leu Ser Leu Ile Cys Leu
            435                 440                 445

Leu Gly Tyr Ser Met Leu Leu Met Val Thr Cys Thr Val Tyr Ala Ile
            450                 455                 460

Lys Thr Arg Gly Val Pro Glu Thr Phe Asn Glu Ala Lys Pro Ile Gly
465                 470                 475                 480

Phe Thr Met Tyr Thr Thr Cys Ile Val Trp Leu Ala Phe Ile Pro Ile
                485                 490                 495

Phe Phe Gly Thr Ser Gln Ser Ala Asp Lys Leu Tyr Ile Gln Thr Thr
            500                 505                 510
```

```
Thr Leu Thr Val Ser Val Ser Leu Ser Ala Ser Val Ser Leu Gly Met
            515                 520                 525

Leu Tyr Met Pro Lys Val Tyr Ile Ile Leu Phe His Pro Glu Gln Asn
        530                 535                 540

Val Pro Lys Arg Lys Arg Ser Leu Lys Ala Val Val Thr Ala Ala Thr
545                 550                 555                 560

Met Ser Asn Lys Phe Thr Gln Lys Gly Asn Phe Arg Pro Asn Gly Glu
                565                 570                 575

Ala Lys Ser Glu Leu Cys Glu Asn Leu Glu Ala Pro Ala Leu Ala Thr
            580                 585                 590

Lys Gln Thr Tyr Val Thr Tyr Thr Asn His Ala Ile
            595                 600

<210> SEQ ID NO 27
<211> LENGTH: 900
<212> TYPE: DNA
<213> ORGANISM: homo sapiens

<400> SEQUENCE: 27
atgctagagt ctcacctcat tatctatttt cttcttgcag tgatacaatt tcttcttggg      60
attttcacaa atggcatcat tgtggtggtg aatggcattg acttgatcaa gcacagaaaa     120
atggctccgc tggatctcct tctttcttgt ctggcagttt ctagaatttt tctgcagttg     180
ttcatcttct acgttaatgt gattgttatc ttccttcatag aattcatcat gtgttctgcg     240
aattgtgcaa ttctcttatt tataaatgaa ttggaacttt ggcttgccac atggctcggc     300
gttttctatt gtgccaaggt tgccagcgtc cgtcacccac tcttcatctg gttgaagatg     360
aggatatcca agctggtccc atggatgatc ctggggtctc tgctatatgt atctatgatt     420
tgtgttttcc atagcaaata tgcagggttt atggtcccat acttcctaag gaaatttttc     480
tcccaaaatg ccacaattca aaagaagat acactggcta tacagatttt ctcttttgtt      540
gctgagttct cagtgccatt gcttatcttc ctttttgctg ttttgctctt gattttctct     600
ctggggaggc acacccggca atgagaaac acagtggccg gcagcagggt tcctggcagg      660
ggtgcaccca tcagcgcgtt gctgtctatc ctgtccttcc tgatcctcta cttctcccac     720
tgcatgataa agttttttct ctcttctcta agtttcaca tcagaaggtt catctttctg      780
ttcttcatcc ttgtgattgg tatatacct tctggacact ctctcatctt aattttagga      840
aatcctaaat tgaaacaaaa tgcaaaaaag ttcctcctcc acagtaagtg ctgtcagtga     900

<210> SEQ ID NO 28
<211> LENGTH: 299
<212> TYPE: PRT
<213> ORGANISM: homo sapiens

<400> SEQUENCE: 28

Met Leu Glu Ser His Leu Ile Ile Tyr Phe Leu Leu Ala Val Ile Gln
1               5                   10                  15

Phe Leu Leu Gly Ile Phe Thr Asn Gly Ile Ile Val Val Asn Gly
            20                  25                  30

Ile Asp Leu Ile Lys His Arg Lys Met Ala Pro Leu Asp Leu Leu Leu
            35                  40                  45

Ser Cys Leu Ala Val Ser Arg Ile Phe Leu Gln Leu Phe Ile Phe Tyr
        50                  55                  60

Val Asn Val Ile Val Ile Phe Phe Ile Glu Phe Ile Met Cys Ser Ala
65                  70                  75                  80
```

```
Asn Cys Ala Ile Leu Leu Phe Ile Asn Glu Leu Glu Leu Trp Leu Ala
                 85                  90                  95
Thr Trp Leu Gly Val Phe Tyr Cys Ala Lys Val Ala Ser Val Arg His
            100                 105                 110
Pro Leu Phe Ile Trp Leu Lys Met Arg Ile Ser Lys Leu Val Pro Trp
        115                 120                 125
Met Ile Leu Gly Ser Leu Leu Tyr Val Ser Met Ile Cys Val Phe His
    130                 135                 140
Ser Lys Tyr Ala Gly Phe Met Val Pro Tyr Phe Leu Arg Lys Phe Phe
145                 150                 155                 160
Ser Gln Asn Ala Thr Ile Gln Lys Glu Asp Thr Leu Ala Ile Gln Ile
                165                 170                 175
Phe Ser Phe Val Ala Glu Phe Ser Val Pro Leu Leu Ile Phe Leu Phe
            180                 185                 190
Ala Val Leu Leu Leu Ile Phe Ser Leu Gly Arg His Thr Arg Gln Met
        195                 200                 205
Arg Asn Thr Val Ala Gly Ser Arg Val Pro Gly Arg Gly Ala Pro Ile
    210                 215                 220
Ser Ala Leu Leu Ser Ile Leu Ser Phe Leu Ile Leu Tyr Phe Ser His
225                 230                 235                 240
Cys Met Ile Lys Val Phe Leu Ser Ser Leu Lys Phe His Ile Arg Arg
                245                 250                 255
Phe Ile Phe Leu Phe Phe Ile Leu Val Ile Gly Ile Tyr Pro Ser Gly
            260                 265                 270
His Ser Leu Ile Leu Ile Leu Gly Asn Pro Lys Leu Lys Gln Asn Ala
        275                 280                 285
Lys Lys Phe Leu Leu His Ser Lys Cys Cys Gln
    290                 295
```

<210> SEQ ID NO 29
<211> LENGTH: 951
<212> TYPE: DNA
<213> ORGANISM: homo sapiens

<400> SEQUENCE: 29

```
atgatgggac tcaccgaggg ggtgttcctg attctgtctg gcactcagtt cacactggga      60
attctggtca attgtttcat tgagttggtc aatggtagca gctggttcaa gaccaagaga    120
atgtctttgt ctgacttcat catcaccacc ctggcactct gaggatcat tctgctgtgt     180
attatcttga ctgatagttt tttaatagaa ttctctccca acacacatga ttcaggaata    240
ataatgcaaa ttattgatgt ttcctggaca tttacaaacc atctgagcat ttggcttgcc    300
acctgtcttg gtgtcctcta ctgcctgaaa atcgccagtt tctctcaccc cacattcctc    360
tggctcaagt ggagagtttc tagggtgatg gtatggatgc tgttgggtgc actgctctta    420
tcctgtggta gtaccgcatc tctgatcaat gagtttaagc tctattctgt ctttagggga    480
attgaggcca ccaggaatgt gactgaacac ttcagaaaga gaggagtga gtattatctg     540
atccatgttc ttgggactct gtggtacctg cctcccttaa ttgtgtccct ggcctcctac    600
tctttgctca tcttctccct ggggaggcac acacggcaga tgctgcaaaa tgggacaagc    660
tccagagatc caaccactga ggcccacaag agggccatca gaatcatcct tccttcttc     720
tttctcttct tacttactt tcttgctttc ttaattgcat catttggtaa tttcctacca    780
aaaaccaaga tggctaagat gattggtgaa gtaatgacaa tgttttatcc tgctggccac    840
tcatttattc tcattctggg gaacagtaag ctgaagcaga catttgtagt gatgctccgg    900
```
tgtgagtctg gtcatctgaa gcctggatcc aagggaccca ttttctctta g         951

<210> SEQ ID NO 30
<211> LENGTH: 316
<212> TYPE: PRT
<213> ORGANISM: homo sapiens

<400> SEQUENCE: 30

Met Met Gly Leu Thr Glu Gly Val Phe Leu Ile Leu Ser Gly Thr Gln
1               5                   10                  15

Phe Thr Leu Gly Ile Leu Val Asn Cys Phe Ile Glu Leu Val Asn Gly
            20                  25                  30

Ser Ser Trp Phe Lys Thr Lys Arg Met Ser Leu Ser Asp Phe Ile Ile
        35                  40                  45

Thr Thr Leu Ala Leu Leu Arg Ile Ile Leu Leu Cys Ile Ile Leu Thr
50                  55                  60

Asp Ser Phe Leu Ile Glu Phe Ser Pro Asn Thr His Asp Ser Gly Ile
65                  70                  75                  80

Ile Met Gln Ile Ile Asp Val Ser Trp Thr Phe Thr Asn His Leu Ser
                85                  90                  95

Ile Trp Leu Ala Thr Cys Leu Gly Val Leu Tyr Cys Leu Lys Ile Ala
            100                 105                 110

Ser Phe Ser His Pro Thr Phe Leu Trp Leu Lys Trp Arg Val Ser Arg
        115                 120                 125

Val Met Val Trp Met Leu Leu Gly Ala Leu Leu Leu Ser Cys Gly Ser
130                 135                 140

Thr Ala Ser Leu Ile Asn Glu Phe Lys Leu Tyr Ser Val Phe Arg Gly
145                 150                 155                 160

Ile Glu Ala Thr Arg Asn Val Thr Glu His Phe Arg Lys Lys Arg Ser
                165                 170                 175

Glu Tyr Tyr Leu Ile His Val Leu Gly Thr Leu Trp Tyr Leu Pro Pro
            180                 185                 190

Leu Ile Val Ser Leu Ala Ser Tyr Ser Leu Leu Ile Phe Ser Leu Gly
        195                 200                 205

Arg His Thr Arg Gln Met Leu Gln Asn Gly Thr Ser Ser Arg Asp Pro
210                 215                 220

Thr Thr Glu Ala His Lys Arg Ala Ile Arg Ile Ile Leu Ser Phe Phe
225                 230                 235                 240

Phe Leu Phe Leu Leu Tyr Phe Leu Ala Phe Leu Ile Ala Ser Phe Gly
                245                 250                 255

Asn Phe Leu Pro Lys Thr Lys Met Ala Lys Met Ile Gly Glu Val Met
            260                 265                 270

Thr Met Phe Tyr Pro Ala Gly His Ser Phe Ile Leu Ile Leu Gly Asn
        275                 280                 285

Ser Lys Leu Lys Gln Thr Phe Val Val Met Leu Arg Cys Glu Ser Gly
        290                 295                 300

His Leu Lys Pro Gly Ser Lys Gly Pro Ile Phe Ser
305                 310                 315

<210> SEQ ID NO 31
<211> LENGTH: 900
<212> TYPE: DNA
<213> ORGANISM: homo sapiens

<400> SEQUENCE: 31

```
atgcttcggt tattctattt ctctgctatt attgcctcag ttattttaaa ttttgtagga      60
atcattatga atctgtttat tacagtggtc aattgcaaaa cttgggtcaa aagccataga     120
atctcctctt ctgataggat tctgttcagc ctgggcatca ccaggtttct tatgctggga     180
ctatttctgg tgaacaccat ctacttcgtc tcttcaaata cggaaaggtc agtctacctg     240
tctgcttttt ttgtgttgtg tttcatgttt ttggactcga gcagtgtctg gtttgtgacc     300
ttgctcaata tcttgtactg tgtgaagatt actaacttcc aacactcagt gtttctcctg     360
ctgaagcgga atatctcccc aaagatcccc aggctgctgc tggcctgtgt gctgatttct     420
gctttcacca cttgcctgta catcacgctt agccaggcat caccttttcc tgaacttgtg     480
actacgagaa ataacacatc atttaatatc agtgagggca tcttgtcttt agtggtttct     540
ttggtcttga gctcatctct ccagttcatc attaatgtga cttctgcttc cttgctaata     600
cactccttga ggagacatat acagaagatg cagaaaaatg ccactggttt ctggaatccc     660
cagacggaag ctcatgtagg tgctatgaag ctgatggtct atttcctcat cctctacatt     720
ccatattcag ttgctaccct ggtccagtat ctccccttt atgcagggat ggatatgggg     780
accaaatcca tttgtctgat ttttgccacc ctttactctc caggacattc tgttctcatt     840
attatcacac atcctaaact gaaacaaca gcaagaaga ttctttgttt caaaaaatag      900
```

<210> SEQ ID NO 32
<211> LENGTH: 299
<212> TYPE: PRT
<213> ORGANISM: homo sapiens

<400> SEQUENCE: 32

```
Met Leu Arg Leu Phe Tyr Phe Ser Ala Ile Ile Ala Ser Val Ile Leu
1               5                   10                  15

Asn Phe Val Gly Ile Ile Met Asn Leu Phe Ile Thr Val Val Asn Cys
            20                  25                  30

Lys Thr Trp Val Lys Ser His Arg Ile Ser Ser Ser Asp Arg Ile Leu
        35                  40                  45

Phe Ser Leu Gly Ile Thr Arg Phe Leu Met Leu Gly Leu Phe Leu Val
    50                  55                  60

Asn Thr Ile Tyr Phe Val Ser Ser Asn Thr Glu Arg Ser Val Tyr Leu
65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
            100                 105                 110

Phe Gln His Ser Val Phe Leu Leu Lys Arg Asn Ile Ser Pro Lys
        115                 120                 125

Ile Pro Arg Leu Leu Leu Ala Cys Val Leu Ile Ser Ala Phe Thr Thr
    130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Leu Gln Phe Ile Ile Asn
            180                 185                 190

Val Thr Ser Ala Ser Leu Leu Ile His Ser Leu Arg Arg His Ile Gln
        195                 200                 205

Lys Met Gln Lys Asn Ala Thr Gly Phe Trp Asn Pro Gln Thr Glu Ala
    210                 215                 220
```

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
            245                 250                 255

Met Asp Met Gly Thr Lys Ser Ile Cys Leu Ile Phe Ala Thr Leu Tyr
        260                 265                 270

Ser Pro Gly His Ser Val Leu Ile Ile Ile Thr His Pro Lys Leu Lys
    275                 280                 285

Thr Thr Ala Lys Lys Ile Leu Cys Phe Lys Lys
        290                 295

<210> SEQ ID NO 33
<211> LENGTH: 900
<212> TYPE: DNA
<213> ORGANISM: homo sapiens

<400> SEQUENCE: 33
atgctgagcg ctggcctagg actgctgatg ctggtggcag tggttgaatt tctcatcggt      60
ttaattggaa atggaagcct ggtggtctgg agttttagag aatggatcag aaaattcaac     120
tggtcctcat ataacctcat tatcctgggc ctggctggct gccgatttct cctgcagtgg     180
ctgatcattt tggacttaag cttgtttcca cttttccaga gcagccgttg gcttcgctat     240
cttagtatct tctgggtcct ggtaagccag gccagcttat ggtttgccac cttcctcagt     300
gtcttctatt gcaagaagat cacgaccttc gatcgcccgg cctacttgtg gctgaagcag     360
agggcctata acctgagtct ctggtgcctt ctgggctact ttataatcaa tttgttactt     420
acagtccaaa ttggcttaac attctatcat cctccccaag aaacagcag cattcggtat     480 cccttgaaa gctggcagta cctgtatgca tttcagctca attcaggaag ttatttgcct     540
ttagtggtgt tcttgtttc ctctgggatg ctgattgtct cttgtatac acaccacaag     600 aagatgaagg tccattcagc tggtaggagg gatgtccggg ccaaggctca catcactgcg     660
ctgaagtcct tgggctgctt cctcttactt cacctggttt atatcatggc cagccccttc     720
tccatcacct ccaagactta tcctcctgat ctcaccagtg tcttcatctg ggagacactc     780
atggcagcct atccttctct tcattctctc atattgatca tggggattcc tagggtgaag     840
cagacttgtc agaagatcct gtggaagaca gtgtgtgctc ggagatgctg ggcccatga     900

<210> SEQ ID NO 34
<211> LENGTH: 299
<212> TYPE: PRT
<213> ORGANISM: homo sapiens

<400> SEQUENCE: 34

Met Leu Ser Ala Gly Leu Gly Leu Leu Met Leu Val Ala Val Val Glu
1               5                   10                  15

Phe Leu Ile Gly Leu Ile Gly Asn Gly Ser Leu Val Val Trp Ser Phe
            20                  25                  30

Arg Glu Trp Ile Arg Lys Phe Asn Trp Ser Ser Tyr Asn Leu Ile Ile
        35                  40                  45

Leu Gly Leu Ala Gly Cys Arg Phe Leu Leu Gln Trp Leu Ile Ile Leu
    50                  55                  60

Asp Leu Ser Leu Phe Pro Leu Phe Gln Ser Ser Arg Trp Leu Arg Tyr
65                  70                  75                  80

Leu Ser Ile Phe Trp Val Leu Val Ser Gln Ala Ser Leu Trp Phe Ala
            85                  90                  95

```
Thr Phe Leu Ser Val Phe Tyr Cys Lys Lys Ile Thr Thr Phe Asp Arg
            100                 105                 110

Pro Ala Tyr Leu Trp Leu Lys Gln Arg Ala Tyr Asn Leu Ser Leu Trp
        115                 120                 125

Cys Leu Leu Gly Tyr Phe Ile Ile Asn Leu Leu Thr Val Gln Ile
130                 135                 140

Gly Leu Thr Phe Tyr His Pro Pro Gln Gly Asn Ser Ser Ile Arg Tyr
145                 150                 155                 160

Pro Phe Glu Ser Trp Gln Tyr Leu Tyr Ala Phe Gln Leu Asn Ser Gly
                165                 170                 175

Ser Tyr Leu Pro Leu Val Val Phe Leu Val Ser Ser Gly Met Leu Ile
            180                 185                 190

Val Ser Leu Tyr Thr His His Lys Lys Met Lys Val His Ser Ala Gly
        195                 200                 205

Arg Arg Asp Val Arg Ala Lys Ala His Ile Thr Ala Leu Lys Ser Leu
    210                 215                 220

Gly Cys Phe Leu Leu Leu His Leu Val Tyr Ile Met Ala Ser Pro Phe
225                 230                 235                 240

Ser Ile Thr Ser Lys Thr Tyr Pro Pro Asp Leu Thr Ser Val Phe Ile
                245                 250                 255

Trp Glu Thr Leu Met Ala Ala Tyr Pro Ser Leu His Ser Leu Ile Leu
            260                 265                 270

Ile Met Gly Ile Pro Arg Val Lys Gln Thr Cys Gln Lys Ile Leu Trp
        275                 280                 285

Lys Thr Val Cys Ala Arg Arg Cys Trp Gly Pro
    290                 295

<210> SEQ ID NO 35
<211> LENGTH: 957
<212> TYPE: DNA
<213> ORGANISM: homo sapiens

<400> SEQUENCE: 35
atggcagata aagtgcagac tactttattg ttcttagcag ttggagagtt ttcagtgggg    60
atcttaggga atgcattcat tggattggta aactgcatgg actgggtcaa gaagaggaaa   120
attgcctcca ttgatttaat cctcacaagt ctggccatat ccagaatttg tctattgtgc   180
gtaatactat tagattgttt tatattggtg ctatatccag atgtctatgc cactggtaaa   240
gaaatgagaa tcattgactt cttctggaca ctaaccaatc atttaagtat ctggtttgca   300
acctgcctca gcatttacta tttcttcaag ataggtaatt tctttcaccc acttttcctc   360
tggatgaagt ggagaattga cagggtgatt tcctggattc tactggggtg cgtggttctc   420
tctgtgttta ttagccttcc agccactgag aatttgaacg ctgatttcag gttttgtgtg   480
aaggcaaaga ggaaaacaaa cttaacttgg agttgcagag taaataaaac tcaacatgct   540
tctaccaagt tatttctcaa cctggcaacg ctgctcccct tttgtgtgtg cctaatgtcc   600 ttttcctct tgatcctctc cctgcggaga catatcaggc gaatgcagct cagtgccaca   660
gggtgcagag acccccagcac agaagcccat gtgagagccc tgaaagctgt catttccttc   720
cttctcctct ttattgccta ctatttgtcc tttctcattg ccacctccag ctactttatg   780
ccagagacgg aattagctgt gattttttggt gagtccatag ctctaatcta cccctcaagt   840
cattcattta tcctaatact ggggaacaat aaattaagac atgcatctct aaaggtgatt   900
tggaaagtaa tgtctattct aaaaggaaga aaattccaac aacataaaca aatctga      957
```

<210> SEQ ID NO 36
<211> LENGTH: 318
<212> TYPE: PRT
<213> ORGANISM: homo sapiens

<400> SEQUENCE: 36

```
Met Ala Asp Lys Val Gln Thr Thr Leu Leu Phe Leu Ala Val Gly Glu
1               5                   10                  15

Phe Ser Val Gly Ile Leu Gly Asn Ala Phe Ile Gly Leu Val Asn Cys
            20                  25                  30

Met Asp Trp Val Lys Lys Arg Lys Ile Ala Ser Ile Asp Leu Ile Leu
        35                  40                  45

Thr Ser Leu Ala Ile Ser Arg Ile Cys Leu Leu Cys Val Ile Leu Leu
    50                  55                  60

Asp Cys Phe Ile Leu Val Leu Tyr Pro Asp Val Tyr Ala Thr Gly Lys
65                  70                  75                  80

Glu Met Arg Ile Ile Asp Phe Phe Trp Thr Leu Thr Asn His Leu Ser
                85                  90                  95

Ile Trp Phe Ala Thr Cys Leu Ser Ile Tyr Tyr Phe Lys Ile Gly
            100                 105                 110

Asn Phe His Pro Leu Phe Leu Trp Met Lys Trp Arg Ile Asp Arg
        115                 120                 125

Val Ile Ser Trp Ile Leu Leu Gly Cys Val Val Leu Ser Val Phe Ile
    130                 135                 140

Ser Leu Pro Ala Thr Glu Asn Leu Asn Ala Asp Phe Arg Phe Cys Val
145                 150                 155                 160

Lys Ala Lys Arg Lys Thr Asn Leu Thr Trp Ser Cys Arg Val Asn Lys
                165                 170                 175

Thr Gln His Ala Ser Thr Lys Leu Phe Leu Asn Leu Ala Thr Leu Leu
            180                 185                 190

Pro Phe Cys Val Cys Leu Met Ser Phe Leu Leu Ile Leu Ser Leu
        195                 200                 205

Arg Arg His Ile Arg Arg Met Gln Leu Ser Ala Thr Gly Cys Arg Asp
    210                 215                 220

Pro Ser Thr Glu Ala His Val Arg Ala Leu Lys Ala Val Ile Ser Phe
225                 230                 235                 240

Leu Leu Leu Phe Ile Ala Tyr Tyr Leu Ser Phe Leu Ile Ala Thr Ser
                245                 250                 255

Ser Tyr Phe Met Pro Glu Thr Glu Leu Ala Val Ile Phe Gly Glu Ser
            260                 265                 270

Ile Ala Leu Ile Tyr Pro Ser Ser His Ser Phe Ile Leu Ile Leu Gly
        275                 280                 285

Asn Asn Lys Leu Arg His Ala Ser Leu Lys Val Ile Trp Lys Val Met
    290                 295                 300

Ser Ile Leu Lys Gly Arg Lys Phe Gln Gln His Lys Gln Ile
305                 310                 315
```

<210> SEQ ID NO 37
<211> LENGTH: 930
<212> TYPE: DNA
<213> ORGANISM: homo sapiens

<400> SEQUENCE: 37
atgttcagtc ctgcagataa catctttata atcctaataa ctggagaatt catactagga      60

```
atattgggga atggatacat tgcactagtc aactggattg actggattaa gaagaaaaag      120
atttccacag ttgactacat ccttaccaat ttagttatcg ccagaatttg tttgatcagt      180
gtaatggttg taaatggcat tgtaatagta ctgaacccag atgtttatac aaaaaataaa      240
caacagatag tcattttac cttctggaca tttgccaact acttaaatat gtggattacc       300
acctgcctta atgtcttcta ttttctgaag atagccagtt cctctcatcc acttttctc      360 tggctgaagt ggaaaattga tatggtggtg cactggatcc tgctgggatg ctttgccatt      420
tccttgttgg tcagccttat agcagcaata gtactgagtt gtgattatag gtttcatgca      480
attgccaaac ataaaagaaa cattactgaa atgttccatg tgagtaaaat accatacttt      540
gaacccttga ctctctttaa cctgtttgca attgtcccat ttattgtgtc actgatatca      600
tttttccttt tagtaagatc tttatggaga cataccaagc aaataaaact ctatgctacc      660
ggcagtagag accccagcac agaagttcat gtgagagcca ttaaaactat gacttcattt      720
atcttctttt ttttcctata ctatatttct tctattttga tgacctttag ctatcttatg      780
acaaaataca agttagctgt ggagtttgga gagattgcag caattctcta ccccttgggt      840
cactcactta ttttaattgt tttaaataat aaactgaggc agacatttgt cagaatgctg      900
acatgtagaa aaattgcctg catgatatga                                       930
```

<210> SEQ ID NO 38
<211> LENGTH: 309
<212> TYPE: PRT
<213> ORGANISM: homo sapiens

<400> SEQUENCE: 38

```
Met Phe Ser Pro Ala Asp Asn Ile Phe Ile Ile Leu Ile Thr Gly Glu
1               5                   10                  15

Phe Ile Leu Gly Ile Leu Gly Asn Gly Tyr Ile Ala Leu Val Asn Trp
            20                  25                  30

Ile Asp Trp Ile Lys Lys Lys Ile Ser Thr Val Asp Tyr Ile Leu
        35                  40                  45

Thr Asn Leu Val Ile Ala Arg Ile Cys Leu Ile Ser Val Met Val Val
50                  55                  60

Asn Gly Ile Val Ile Val Leu Asn Pro Asp Val Tyr Thr Lys Asn Lys
65                  70                  75                  80

Gln Gln Ile Val Ile Phe Thr Phe Trp Thr Phe Ala Asn Tyr Leu Asn
            85                  90                  95

Met Trp Ile Thr Thr Cys Leu Asn Val Phe Tyr Phe Leu Lys Ile Ala
            100                 105                 110

Ser Ser Ser His Pro Leu Phe Leu Trp Leu Lys Trp Lys Ile Asp Met
        115                 120                 125

Val Val His Trp Ile Leu Leu Gly Cys Phe Ala Ile Ser Leu Leu Val
    130                 135                 140

Ser Leu Ile Ala Ala Ile Val Leu Ser Cys Asp Tyr Arg Phe His Ala
145                 150                 155                 160

Ile Ala Lys His Lys Arg Asn Ile Thr Glu Met Phe His Val Ser Lys
            165                 170                 175

Ile Pro Tyr Phe Glu Pro Leu Thr Leu Phe Asn Leu Phe Ala Ile Val
            180                 185                 190

Pro Phe Ile Val Ser Leu Ile Ser Phe Phe Leu Leu Val Arg Ser Leu
        195                 200                 205

Trp Arg His Thr Lys Gln Ile Lys Leu Tyr Ala Thr Gly Ser Arg Asp
    210                 215                 220
```

```
Pro Ser Thr Glu Val His Val Arg Ala Ile Lys Thr Met Thr Ser Phe
225                 230                 235                 240

Ile Phe Phe Phe Phe Leu Tyr Tyr Ile Ser Ser Ile Leu Met Thr Phe
                245                 250                 255

Ser Tyr Leu Met Thr Lys Tyr Lys Leu Ala Val Glu Phe Gly Glu Ile
                260                 265                 270

Ala Ala Ile Leu Tyr Pro Leu Gly His Ser Leu Ile Leu Ile Val Leu
                275                 280                 285

Asn Asn Lys Leu Arg Gln Thr Phe Val Arg Met Leu Thr Cys Arg Lys
                290                 295                 300

Ile Ala Cys Met Ile
305

<210> SEQ ID NO 39
<211> LENGTH: 939
<212> TYPE: DNA
<213> ORGANISM: homo sapiens

<400> SEQUENCE: 39
atgccaagtg caatagaggc aatatatatt attttaattg ctggtgaatt gaccataggg      60
atttggggaa atggattcat tgtactagtt aactgcattg actggctcaa agaagagat     120 atttccttga ttacatcat cctgatcagc ttggccatct ccagaatctg tctgctgtgt     180
gtaatatcat tagatggctt ctttatgctg ctctttccag gtacatatgg caatagcgtg     240
ctagtaagca ttgtgaatgt tgtctggaca tttgccaata attcaagtct ctggtttact     300
tcttgcctca gtatcttcta tttactcaag atagccaata tatcgcaccc attttcttc     360 tggctgaagc taaagatcaa caaggtcatg cttgcgattc ttctgggtc ctttcttatc     420 tctttaatta ttagtgttcc aaagaatgat gatatgtggt atcaccttt caaagtcagt     480 catgaagaaa acattacttg gaaattcaaa gtgagtaaaa ttccaggtac tttcaaacag     540
ttaaccctga acctgggggt gatggttccc tttatccttt gcctgatctc attttcttg     600 ttacttttct ccctagttag acacaccaag cagattcgac tgcatgctac agggttcaga     660
gaccccagta cagaggccca catgagggcc ataaaggcag tgatcatctt tctgctcctc     720
ctcatcgtgt actacccagt cttcttgtt atgacctcta gcgctctgat tcctcaggga     780
aaattagtgt tgatgattgg tgacatagta actgtcattt tcccatcaag ccattcattc     840
attctaatta tgggaaatag caagttgagg gaagcttttc tgaagatgtt aagatttgtg     900 aagtgttttcc ttagaagaag aaagcctttt gttccatag                           939

<210> SEQ ID NO 40
<211> LENGTH: 312
<212> TYPE: PRT
<213> ORGANISM: homo sapiens

<400> SEQUENCE: 40

Met Pro Ser Ala Ile Glu Ala Ile Tyr Ile Ile Leu Ile Ala Gly Glu
1               5                  10                  15

Leu Thr Ile Gly Ile Trp Gly Asn Gly Phe Ile Val Leu Val Asn Cys
                20                  25                  30

Ile Asp Trp Leu Lys Arg Arg Asp Ile Ser Leu Ile Asp Ile Ile Leu
                35                  40                  45

Ile Ser Leu Ala Ile Ser Arg Ile Cys Leu Leu Cys Val Ile Ser Leu
                50                  55                  60
```

Asp Gly Phe Phe Met Leu Leu Phe Pro Gly Thr Tyr Gly Asn Ser Val
65                  70                  75                  80

Leu Val Ser Ile Val Asn Val Val Trp Thr Phe Ala Asn Asn Ser Ser
            85                  90                  95

Leu Trp Phe Thr Ser Cys Leu Ser Ile Phe Tyr Leu Leu Lys Ile Ala
        100                 105                 110

Asn Ile Ser His Pro Phe Phe Trp Leu Lys Leu Lys Ile Asn Lys
    115                 120                 125

Val Met Leu Ala Ile Leu Leu Gly Ser Phe Leu Ile Ser Leu Ile Ile
130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
                165                 170                 175

Thr Phe Lys Gln Leu Thr Leu Asn Leu Gly Val Met Val Pro Phe Ile
            180                 185                 190

Leu Cys Leu Ile Ser Phe Phe Leu Leu Phe Ser Leu Val Arg His
        195                 200                 205

Thr Lys Gln Ile Arg Leu His Ala Thr Gly Phe Arg Asp Pro Ser Thr
    210                 215                 220

Glu Ala His Met Arg Ala Ile Lys Ala Val Ile Ile Phe Leu Leu Leu
225                 230                 235                 240

Leu Ile Val Tyr Tyr Pro Val Phe Leu Val Met Thr Ser Ser Ala Leu
                245                 250                 255

Ile Pro Gln Gly Lys Leu Val Leu Met Ile Gly Asp Ile Val Thr Val
            260                 265                 270

Ile Phe Pro Ser Ser His Ser Phe Ile Leu Met Gly Asn Ser Lys
        275                 280                 285

Leu Arg Glu Ala Phe Leu Lys Met Leu Arg Phe Val Lys Cys Phe Leu
    290                 295                 300

Arg Arg Arg Lys Pro Phe Val Pro
305                 310

<210> SEQ ID NO 41
<211> LENGTH: 924
<212> TYPE: DNA
<213> ORGANISM: homo sapiens

<400> SEQUENCE: 41
atgctacgtg tagtggaagg catcttcatt tttgttgtag ttagtgagtc agtgtttggg      60
gttttgggga atggatttat tggacttgta aactgcattg actgtgccaa gaataagtta     120
tctacgattg gctttattct caccggctta gctatttcaa gaatttttct gatatggata     180
ataattacag atggatttat acagatattc tctccaaata tatgcctc cggtaaccta      240 attgaatata ttagttactt tgggtaatt ggtaatcaat caagtatgtg gtttgccacc      300
agcctcagca tcttctattt cctgaagata gcaaattttt ccaactacat atttctctgg     360
ttgaagagca gaacaaatat ggttcttccc ttcatgatag tattcttact tatttcatcg     420
ttacttaatt ttgcatacat tgcgaagatt cttaatgatt ataaaacgaa gaatgacaca     480
gtctgggatc tcaacatgta taaagtgaa tactttatta aacagatttt gctaaatctg     540
ggagtcattt tcttctttac actatcccta attacatgta ttttttttaat catttcccttt    600 tggagacaca caggcagat gcaatcgaat gtgacaggat tgagagactc caacacagaa     660
gctcatgtga aggcaatgaa agttttgata tctttcatca tcctctttat cttgtatttt     720

```
ataggcatgg ccatagaaat atcatgtttt actgtgcgag aaaacaaact gctgcttatg    780
tttggaatga caaccacagc catctatccc tggggtcact catttatctt aattctagga    840
aacagcaagc taaagcaagc ctctttgagg gtactgcagc aattgaagtg ctgtgagaaa    900
aggaaaaatc tcagagtcac atag                                          924

<210> SEQ ID NO 42
<211> LENGTH: 307
<212> TYPE: PRT
<213> ORGANISM: homo sapiens

<400> SEQUENCE: 42

Met Leu Arg Val Val Glu Gly Ile Phe Ile Phe Val Val Ser Glu
1               5                   10                  15

Ser Val Phe Gly Val Leu Gly Asn Gly Phe Ile Gly Leu Val Asn Cys
                20                  25                  30

Ile Asp Cys Ala Lys Asn Lys Leu Ser Thr Ile Gly Phe Ile Leu Thr
            35                  40                  45

Gly Leu Ala Ile Ser Arg Ile Phe Leu Ile Trp Ile Ile Thr Asp
50                  55                  60

Gly Phe Ile Gln Ile Phe Ser Pro Asn Ile Tyr Ala Ser Gly Asn Leu
65                  70                  75                  80

Ile Glu Tyr Ile Ser Tyr Phe Trp Val Ile Gly Asn Gln Ser Ser Met
                85                  90                  95

Trp Phe Ala Thr Ser Leu Ser Ile Phe Tyr Phe Leu Lys Ile Ala Asn
            100                 105                 110

Phe Ser Asn Tyr Ile Phe Leu Trp Leu Lys Ser Arg Thr Asn Met Val
        115                 120                 125

Leu Pro Phe Met Ile Val Phe Leu Leu Ile Ser Ser Leu Leu Asn Phe
130                 135                 140

Ala Tyr Ile Ala Lys Ile Leu Asn Asp Tyr Lys Thr Lys Asn Asp Thr
145                 150                 155                 160

Val Trp Asp Leu Asn Met Tyr Lys Ser Glu Tyr Phe Ile Lys Gln Ile
                165                 170                 175

Leu Leu Asn Leu Gly Val Ile Phe Phe Phe Thr Leu Ser Leu Ile Thr
            180                 185                 190

Cys Ile Phe Leu Ile Ile Ser Leu Trp Arg His Asn Arg Gln Met Gln
        195                 200                 205

Ser Asn Val Thr Gly Leu Arg Asp Ser Asn Thr Glu Ala His Val Lys
210                 215                 220

Ala Met Lys Val Leu Ile Ser Phe Ile Ile Leu Phe Ile Leu Tyr Phe
225                 230                 235                 240

Ile Gly Met Ala Ile Glu Ile Ser Cys Phe Thr Val Arg Glu Asn Lys
                245                 250                 255

Leu Leu Leu Met Phe Gly Met Thr Thr Thr Ala Ile Tyr Pro Trp Gly
            260                 265                 270

His Ser Phe Ile Leu Ile Leu Gly Asn Ser Lys Leu Lys Gln Ala Ser
        275                 280                 285

Leu Arg Val Leu Gln Gln Leu Lys Cys Cys Glu Lys Arg Lys Asn Leu
290                 295                 300

Arg Val Thr
305

<210> SEQ ID NO 43
```

<211> LENGTH: 912
<212> TYPE: DNA
<213> ORGANISM: homo sapiens

<400> SEQUENCE: 43

| | |
|---|---|
| atggaaagtg ccctgccgag tatcttcact cttgtaataa ttgcagaatt cataattggg | 60 |
| aatttgagca atggatttat agtactgatc aactgcattg actgggtcag taaaagagag | 120 |
| ctgtcctcag tcgataaact cctcattatc ttggcaatct ccagaattgg gctgatctgg | 180 |
| gaaatattag taagttggtt tttagctctg cattatctag ccatatttgt gtctggaaca | 240 |
| ggattaagaa ttatgatttt tagctggata gtttctaatc acttcaatct ctggcttgct | 300 |
| acaatcttca gcatctttta tttgctcaaa atagcgagtt tctctagccc tgcttttctc | 360 |
| tatttgaagt ggagagtaaa caagtgatt ctgatgatac tgctaggaac cttggtcttc | 420 |
| ttatttttaa atctgataca aataaacatg catataaaag actggctgga ccgatatgaa | 480 |
| agaaacacaa cttggaattt cagtatgagt gactttgaaa cattttcagt gtcggtcaaa | 540 |
| ttcactatga ctatgttcag tctaacacca tttactgtgg ccttcatctc ttttctcctg | 600 |
| ttaattttct ccctgcagaa acatctccag aaaatgcaac tcaattacaa aggacacaga | 660 |
| gaccccagga ccaaggtcca tacaaatgcc ttgaaaattg tgatctcatt ccttttattc | 720 |
| tatgctagtt tctttctatg tgttctcata tcatggattt ctgagctgta tcagaacaca | 780 |
| gtgatctaca tgctttgtga gacgattgga gtcttctctc cttcaagcca ctcctttctt | 840 |
| ctgattctag gaaacgctaa gttaagacag gcctttcttt tggtggcagc taaggtatgg | 900 |
| gctaaacgat ga | 912 |

<210> SEQ ID NO 44
<211> LENGTH: 303
<212> TYPE: PRT
<213> ORGANISM: homo sapiens

<400> SEQUENCE: 44

Met Glu Ser Ala Leu Pro Ser Ile Phe Thr Leu Val Ile Ile Ala Glu
1               5                   10                  15

Phe Ile Ile Gly Asn Leu Ser Asn Gly Phe Ile Val Leu Ile Asn Cys
            20                  25                  30

Ile Asp Trp Val Ser Lys Arg Glu Leu Ser Ser Val Asp Lys Leu Leu
        35                  40                  45

Ile Ile Leu Ala Ile Ser Arg Ile Gly Leu Ile Trp Glu Ile Leu Val
    50                  55                  60

Ser Trp Phe Leu Ala Leu His Tyr Leu Ala Ile Phe Val Ser Gly Thr
65                  70                  75                  80

Gly Leu Arg Ile Met Ile Phe Ser Trp Ile Val Ser Asn His Phe Asn
                85                  90                  95

Leu Trp Leu Ala Thr Ile Phe Ser Ile Phe Tyr Leu Leu Lys Ile Ala
            100                 105                 110

Ser Phe Ser Ser Pro Ala Phe Leu Tyr Leu Lys Trp Arg Val Asn Lys
        115                 120                 125

Val Ile Leu Met Ile Leu Leu Gly Thr Leu Val Phe Leu Phe Leu Asn
    130                 135                 140

Leu Ile Gln Ile Asn Met His Ile Lys Asp Trp Leu Asp Arg Tyr Glu
145                 150                 155                 160

Arg Asn Thr Thr Trp Asn Phe Ser Met Ser Asp Phe Glu Thr Phe Ser
                165                 170                 175

Val Ser Val Lys Phe Thr Met Thr Met Phe Ser Leu Thr Pro Phe Thr
            180                 185                 190

Val Ala Phe Ile Ser Phe Leu Leu Leu Ile Phe Ser Leu Gln Lys His
            195                 200                 205

Leu Gln Lys Met Gln Leu Asn Tyr Lys Gly His Arg Asp Pro Arg Thr
        210                 215                 220

Lys Val His Thr Asn Ala Leu Lys Ile Val Ile Ser Phe Leu Leu Phe
225                 230                 235                 240

Tyr Ala Ser Phe Phe Leu Cys Val Leu Ile Ser Trp Ile Ser Glu Leu
                245                 250                 255

Tyr Gln Asn Thr Val Ile Tyr Met Leu Cys Glu Thr Ile Gly Val Phe
            260                 265                 270

Ser Pro Ser Ser His Ser Phe Leu Leu Ile Leu Gly Asn Ala Lys Leu
        275                 280                 285

Arg Gln Ala Phe Leu Leu Val Ala Ala Lys Val Trp Ala Lys Arg
    290                 295                 300

<210> SEQ ID NO 45
<211> LENGTH: 954
<212> TYPE: DNA
<213> ORGANISM: homo sapiens

<400> SEQUENCE: 45

```
atgggtggtg tcataaagag catatttaca ttcgttttaa ttgtggaatt tataattgga      60
aatttaggaa atagtttcat agcactggtg aactgtattg actgggtcaa gggaagaaag     120
atctcttcgg ttgatcggat cctcactgct ttggcaatct ctcgaattag cctggtttgg     180
ttaatattcg gaagctggtg tgtgtctgtg ttttcccag cttttatttgc cactgaaaaa     240
atgttcagaa tgcttactaa tatctggaca gtgatcaatc attttagtgt ctggttagct     300
acaggcctcg gtactttta tttctcaag atagccaatt tttctaactc tattttctc       360
tacctaaagt ggagggttaa aaaggtggtt ttggtgctgc ttcttgtgac ttcggtcttc     420
ttgttttta atattgcact gataaacatc catataaatg ccagtatcaa tggatacaga     480
agaaacaaga cttgcagttc tgattcaagt aactttacac gattttccag tcttattgta     540
ttaaccagca ctgtgttcat tttcatacc tttactttgt ccctggcaat gtttcttctc     600
ctcatcttct ccatgtggaa acatcgcaag aagatgcagc acactgtcaa atatccgga     660
gacgccagca ccaaagccca cagaggagtt aaaagtgtga tcactttctt cctactctat     720
gccatttttct ctctgtcttt tttcatatca gtttggaccct ctgaaaggtt ggaggaaaat     780
ctaattattc tttcccaggt gatgggaatg cttatccttt catgtcactc atgtgttctg     840
attcttggaa acaagaagct gagacaggcc tctctgtcag tgctactgtg gctgaggtac     900
atgttcaaag atggggagcc ctcaggtcac aaagaattta gagaatcatc ttga           954
```

<210> SEQ ID NO 46
<211> LENGTH: 317
<212> TYPE: PRT
<213> ORGANISM: homo sapiens

<400> SEQUENCE: 46

Met Gly Gly Val Ile Lys Ser Ile Phe Thr Phe Val Leu Ile Val Glu
1               5                   10                  15

Phe Ile Ile Gly Asn Leu Gly Asn Ser Phe Ile Ala Leu Val Asn Cys
            20                  25                  30

Ile Asp Trp Val Lys Gly Arg Lys Ile Ser Ser Val Asp Arg Ile Leu

|   |   | 35 |   |   |   | 40 |   |   |   | 45 |   |   |
|---|---|---|---|---|---|---|---|---|---|---|---|---|

Thr Ala Leu Ala Ile Ser Arg Ile Ser Leu Val Trp Leu Ile Phe Gly
                50                  55                  60

Ser Trp Cys Val Ser Val Phe Phe Pro Ala Leu Phe Ala Thr Glu Lys
 65                  70                  75                  80

Met Phe Arg Met Leu Thr Asn Ile Trp Thr Val Ile Asn His Phe Ser
                 85                  90                  95

Val Trp Leu Ala Thr Gly Leu Gly Thr Phe Tyr Phe Leu Lys Ile Ala
                100                 105                 110

Asn Phe Ser Asn Ser Ile Phe Leu Tyr Leu Lys Trp Arg Val Lys Lys
                115                 120                 125

Val Val Leu Val Leu Leu Val Thr Ser Val Phe Leu Phe Leu Asn
                130                 135                 140

Ile Ala Leu Ile Asn Ile His Ile Asn Ala Ser Ile Asn Gly Tyr Arg
145                 150                 155                 160

Arg Asn Lys Thr Cys Ser Ser Asp Ser Ser Asn Phe Thr Arg Phe Ser
                165                 170                 175

Ser Leu Ile Val Leu Thr Ser Thr Val Phe Ile Phe Ile Pro Phe Thr
                180                 185                 190

Leu Ser Leu Ala Met Phe Leu Leu Leu Ile Phe Ser Met Trp Lys His
                195                 200                 205

Arg Lys Lys Met Gln His Thr Val Lys Ile Ser Gly Asp Ala Ser Thr
210                 215                 220

Lys Ala His Arg Gly Val Lys Ser Val Ile Thr Phe Phe Leu Leu Tyr
225                 230                 235                 240

Ala Ile Phe Ser Leu Ser Phe Phe Ile Ser Val Trp Thr Ser Glu Arg
                245                 250                 255

Leu Glu Glu Asn Leu Ile Ile Leu Ser Gln Val Met Gly Met Ala Tyr
                260                 265                 270

Pro Ser Cys His Ser Cys Val Leu Ile Leu Gly Asn Lys Lys Leu Arg
                275                 280                 285

Gln Ala Ser Leu Ser Val Leu Leu Trp Leu Arg Tyr Met Phe Lys Asp
                290                 295                 300

Gly Glu Pro Ser Gly His Lys Glu Phe Arg Glu Ser Ser
305                 310                 315

<210> SEQ ID NO 47
<211> LENGTH: 876
<212> TYPE: DNA
<213> ORGANISM: homo sapiens

<400> SEQUENCE: 47

| atgataccca tccaactcac tgtcttcttc atgatcatct atgtgcttga gtccttgaca | 60 |
| attattgtgc agagcagcct aattgttgca gtgctgggca gagaatggct gcaagtcaga | 120 |
| aggctgatgc ctgtggacat gattctcatc agcctgggca tctctcgctt ctgtctacag | 180 |
| tgggcatcaa tgctgaacaa tttttgctcc tattttaatt tgaattatgt actttgcaac | 240 |
| ttaacaatca cctgggaatt ttttaatatc cttacattct ggttaaacag cttgcttacc | 300 |
| gtgttctact gcatcaaggt ctcttctttc acccatcaca tctttctctg ctgaggtgg | 360 |
| agaattttga ggttgtttcc ctggatatta ctgggttctc tgatgattac ttgtgtaaca | 420 |
| atcatccctt cagctattgg gaattacatt caaattcagt tactcaccat ggagcatcta | 480 |
| ccaagaaaca gcactgtaac tgacaaactt gaaaattttc atcagtatca gttccaggct | 540 |

```
catacagttg cattggttat tcctttcatc ctgttcctgg cctccaccat ctttctcatg    600
gcatcactga ccaagcagat acaacatcat agcactggtc actgcaatcc aagcatgaaa    660
gcgcgcttca ctgccctgag gtcccttgcc gtcttattta ttgtgtttac ctcttacttt    720
ctaaccatac tcatcaccat tataggtact ctatttgata agagatgttg gttatgggtc    780
tgggaagctt ttgtctatgc tttcatctta atgcattcca cttcactgat gctgagcagc    840
cctacgttga aaaggattct aaagggaaag tgctag    876
```

<210> SEQ ID NO 48
<211> LENGTH: 291
<212> TYPE: PRT
<213> ORGANISM: homo sapiens

<400> SEQUENCE: 48

```
Met Ile Pro Ile Gln Leu Thr Val Phe Phe Met Ile Ile Tyr Val Leu
1               5                   10                  15

Glu Ser Leu Thr Ile Ile Val Gln Ser Ser Leu Ile Val Ala Val Leu
            20                  25                  30

Gly Arg Glu Trp Leu Gln Val Arg Arg Leu Met Pro Val Asp Met Ile
        35                  40                  45

Leu Ile Ser Leu Gly Ile Ser Arg Phe Cys Leu Gln Trp Ala Ser Met
    50                  55                  60

Leu Asn Asn Phe Cys Ser Tyr Phe Asn Leu Asn Tyr Val Leu Cys Asn
65                  70                  75                  80

Leu Thr Ile Thr Trp Glu Phe Phe Asn Ile Leu Thr Phe Trp Leu Asn
                85                  90                  95

Ser Leu Leu Thr Val Phe Tyr Cys Ile Lys Val Ser Ser Phe Thr His
            100                 105                 110

His Ile Phe Leu Trp Leu Arg Trp Arg Ile Leu Arg Leu Phe Pro Trp
        115                 120                 125

Ile Leu Leu Gly Ser Leu Met Ile Thr Cys Val Thr Ile Ile Pro Ser
    130                 135                 140

Ala Ile Gly Asn Tyr Ile Gln Ile Gln Leu Leu Thr Met Glu His Leu
145                 150                 155                 160

Pro Arg Asn Ser Thr Val Thr Asp Lys Leu Glu Asn Phe His Gln Tyr
                165                 170                 175

Gln Phe Gln Ala His Thr Val Ala Leu Val Ile Pro Phe Ile Leu Phe
            180                 185                 190

Leu Ala Ser Thr Ile Phe Leu Met Ala Ser Leu Thr Lys Gln Ile Gln
        195                 200                 205

His His Ser Thr Gly His Cys Asn Pro Ser Met Lys Ala Arg Phe Thr
    210                 215                 220

Ala Leu Arg Ser Leu Ala Val Leu Phe Ile Val Phe Thr Ser Tyr Phe
225                 230                 235                 240

Leu Thr Ile Leu Ile Thr Ile Ile Gly Thr Leu Phe Asp Lys Arg Cys
                245                 250                 255

Trp Leu Trp Val Trp Glu Ala Phe Val Tyr Ala Phe Ile Leu Met His
            260                 265                 270

Ser Thr Ser Leu Met Leu Ser Ser Pro Thr Leu Lys Arg Ile Leu Lys
        275                 280                 285

Gly Lys Cys
    290
```

<210> SEQ ID NO 49

-continued

```
<211> LENGTH: 945
<212> TYPE: DNA
<213> ORGANISM: homo sapiens

<400> SEQUENCE: 49
atggccaccg aattggacaa aatctttctg attctggcaa tagcagaatt catcatcagc      60
atgctgggga atgtgttcat tggactggta aactgctctg aagggatcaa gaaccaaaag     120
gtcttctcag ctgacttcat cctcacctgc ttggctatct ccacaattgg acaactgttg     180
gtgatactgt ttgattcatt tctagtggga cttgcttcac atttatatac cacatataga     240
ctaggaaaaa ctgttattat gctttggcac atgactaatc acttgacaac ctggcttgcc     300
acctgcctaa gcattttcta tttctttaag atagcccact tcccccactc ccttttcctc     360
tggctgaggt ggaggatgaa cggaatgatt gttatgcttc ttatattgtc tttgttctta     420 ctgattttg acagtttagt gctagaaata tttattgata tctcactcaa tataatagat      480
aaaagtaatc tgactttata tttagatgaa agtaaaactc tctatgataa actctctatt     540 ttaaaactc ttctcagctt aaccagtttt atccccttt ctctgttcct gacctccttg       600 cttttttat ttctgtcctt ggtgagacat actagaaatt tgaagctcag ttccttgggc      660
tctagagact ccagcacaga ggcccatagg agggccatga aaatggtgat gtctttcctt     720
ttcctcttca tagttcattt tttttcctta caagtggcca atgggatatt ttttatgttg     780
tggaacaaca agtacataaa gtttgtcatg ttagccttaa atgcctttcc ctcgtgccac     840
tcatttattc tcattctggg aaacagcaag ctgcgacaga cagctgtgag gctactgtgg     900
catcttagga actatacaaa aacaccaaat gctttacctt tgtag                     945

<210> SEQ ID NO 50
<211> LENGTH: 314
<212> TYPE: PRT
<213> ORGANISM: homo sapiens

<400> SEQUENCE: 50

Met Ala Thr Glu Leu Asp Lys Ile Phe Leu Ile Leu Ala Ile Ala Glu
1               5                   10                  15

Phe Ile Ile Ser Met Leu Gly Asn Val Phe Ile Gly Leu Val Asn Cys
            20                  25                  30

Ser Glu Gly Ile Lys Asn Gln Lys Val Phe Ser Ala Asp Phe Ile Leu
        35                  40                  45

Thr Cys Leu Ala Ile Ser Thr Ile Gly Gln Leu Leu Val Ile Leu Phe
    50                  55                  60

Asp Ser Phe Leu Val Gly Leu Ala Ser His Leu Tyr Thr Thr Tyr Arg
65                  70                  75                  80

Leu Gly Lys Thr Val Ile Met Leu Trp His Met Thr Asn His Leu Thr
                85                  90                  95

Thr Trp Leu Ala Thr Cys Leu Ser Ile Phe Tyr Phe Lys Ile Ala
            100                 105                 110

His Phe Pro His Ser Leu Phe Leu Trp Leu Arg Trp Arg Met Asn Gly
        115                 120                 125

Met Ile Val Met Leu Leu Ile Leu Ser Leu Phe Leu Leu Ile Phe Asp
    130                 135                 140

Ser Leu Val Leu Glu Ile Phe Ile Asp Ile Ser Leu Asn Ile Ile Asp
145                 150                 155                 160

Lys Ser Asn Leu Thr Leu Tyr Leu Asp Glu Ser Lys Thr Leu Tyr Asp
                165                 170                 175
```

```
Lys Leu Ser Ile Leu Lys Thr Leu Leu Ser Leu Thr Ser Phe Ile Pro
            180                 185                 190

Phe Ser Leu Phe Leu Thr Ser Leu Leu Phe Leu Phe Leu Ser Leu Val
        195                 200                 205

Arg His Thr Arg Asn Leu Lys Leu Ser Ser Leu Gly Ser Arg Asp Ser
    210                 215                 220

Ser Thr Glu Ala His Arg Arg Ala Met Lys Met Val Met Ser Phe Leu
225                 230                 235                 240

Phe Leu Phe Ile Val His Phe Phe Ser Leu Gln Val Ala Asn Gly Ile
                245                 250                 255

Phe Phe Met Leu Trp Asn Asn Lys Tyr Ile Lys Phe Val Met Leu Ala
            260                 265                 270

Leu Asn Ala Phe Pro Ser Cys His Ser Phe Ile Leu Ile Leu Gly Asn
        275                 280                 285

Ser Lys Leu Arg Gln Thr Ala Val Arg Leu Leu Trp His Leu Arg Asn
    290                 295                 300

Tyr Thr Lys Thr Pro Asn Ala Leu Pro Leu
305                 310

<210> SEQ ID NO 51
<211> LENGTH: 930
<212> TYPE: DNA
<213> ORGANISM: homo sapiens

<400> SEQUENCE: 51
atgacaactt ttatacccat cattttttcc agtgtggtag tggttctatt tgttattgga      60
aattttgcta atggcttcat agcattggta aattccattg agcgggtcaa gagacaaaag     120
atctcttttg ctgaccagat tctcactgct ctggcggtct ccagagttgg tttgctctgg     180
gtattattat taaattggta ttcaactgtg tttaatccag cttttttatag tgtagaagta    240 agaactactg cttataatgt ctgggcagta accggccatt tcagcaactg gcttgctact    300
agcctcagca tatttttattt gctcaagatt gccaatttct ccaaccttat ttttcttcac    360
ttaaagagga gagttaagag tgtcattctg gtgatgctgt gggggccttt actatttttg    420
gcttgtcaac ttttttgtgat aaacatgaaa gagattgtac ggacaaaaga atatgaagga    480
aacatgactt ggaagatcaa attgaggagt gcagtgtacc tttcagatgc gactgtaacc    540
acgctaggaa acttagtgcc cttcactctg accctgctat gttttttgct gttaatctgt    600
tctctgtgta acatctcaa gaagatgcag ctccatggta aaggatctca agatcccagc     660
accaaggtcc acataaaagt tttgcaaact gtgatctttt tcctcttgtt atgtgccatt    720
tactttctgt ccataatgat atcagtttgg agttttggga gtctggaaaa caaacctgtc    780
ttcatgttct gcaaagctat tagattcagc tatccttcaa tccacccatt catcctgatt    840
tggggaaaca agaagctaaa gcagactttt ctttcagttt tgcggcaagt gaggtactgg    900
gtgaaaggag agaagccttc atctccatag                                    930

<210> SEQ ID NO 52
<211> LENGTH: 309
<212> TYPE: PRT
<213> ORGANISM: homo sapiens

<400> SEQUENCE: 52

Met Thr Thr Phe Ile Pro Ile Ile Phe Ser Ser Val Val Val Leu
1               5                   10                  15

Phe Val Ile Gly Asn Phe Ala Asn Gly Phe Ile Ala Leu Val Asn Ser
```

```
                    20                  25                  30
Ile Glu Arg Val Lys Arg Gln Lys Ile Ser Phe Ala Asp Gln Ile Leu
                35                  40                  45
Thr Ala Leu Ala Val Ser Arg Val Gly Leu Leu Trp Val Leu Leu Leu
            50                  55                  60
Asn Trp Tyr Ser Thr Val Phe Asn Pro Ala Phe Tyr Ser Val Glu Val
 65                 70                  75                  80
Arg Thr Thr Ala Tyr Asn Val Trp Ala Val Thr Gly His Phe Ser Asn
                85                  90                  95
Trp Leu Ala Thr Ser Leu Ser Ile Phe Tyr Leu Leu Lys Ile Ala Asn
            100                 105                 110
Phe Ser Asn Leu Ile Phe Leu His Leu Lys Arg Arg Val Lys Ser Val
            115                 120                 125
Ile Leu Val Met Leu Leu Gly Pro Leu Leu Phe Leu Ala Cys Gln Leu
            130                 135                 140
Phe Val Ile Asn Met Lys Glu Ile Val Arg Thr Lys Glu Tyr Glu Gly
145                 150                 155                 160
Asn Met Thr Trp Lys Ile Lys Leu Arg Ser Ala Val Tyr Leu Ser Asp
                165                 170                 175
Ala Thr Val Thr Thr Leu Gly Asn Leu Val Pro Phe Thr Leu Thr Leu
            180                 185                 190
Leu Cys Phe Leu Leu Leu Ile Cys Ser Leu Cys Lys His Leu Lys Lys
            195                 200                 205
Met Gln Leu His Gly Lys Gly Ser Gln Asp Pro Ser Thr Lys Val His
            210                 215                 220
Ile Lys Val Leu Gln Thr Val Ile Phe Phe Leu Leu Cys Ala Ile
225                 230                 235                 240
Tyr Phe Leu Ser Ile Met Ile Ser Val Trp Ser Phe Gly Ser Leu Glu
                245                 250                 255
Asn Lys Pro Val Phe Met Phe Cys Lys Ala Ile Arg Phe Ser Tyr Pro
                260                 265                 270
Ser Ile His Pro Phe Ile Leu Ile Trp Gly Asn Lys Lys Leu Lys Gln
            275                 280                 285
Thr Phe Leu Ser Val Leu Arg Gln Val Arg Tyr Trp Val Lys Gly Glu
            290                 295                 300
Lys Pro Ser Ser Pro
305

<210> SEQ ID NO 53
<211> LENGTH: 900
<212> TYPE: DNA
<213> ORGANISM: homo sapiens

<400> SEQUENCE: 53
atgataactt ttctgcccat catatttttcc attctagtag tggttacatt tgttattgga      60
aattttgcta atggcttcat agcgttggta aattccaccg agtgggtgaa gagacaaaag     120 atctccttg ctgaccaaat tgtcactgct ctggcggtct ccagagttgg tttgctctgg     180
gtgttattat taaattggta ttcaactgtg ttgaatccag cttttttgtag tgtagaatta     240 agaactactg cttataatat ctgggcagta accggccatt tcagcaactg gcctgctact     300
agcctcagca tattttattt gctcaagatt gccaatttct ccaacctat ttttcttcgc     360 ttaaaggaga gagttaagag tgtcattctg gtggtgctgt tggggccttt gctatttttg     420
gcttgtcatc ttttttgtggt aaacatgaat cagattgtat ggacaaaaga atatgaagga     480
```

```
aacatgactt ggaagatcaa attgaggcgt gcaatgtacc tttcagatac gactgtaacc      540
atgctagcaa acttagtacc ctttactgta accctgatat cttttctgct gttagtctgt      600
tctctgtgta aacatctcaa gaagatgcag ctccatggca aaggatctca agatcccagt      660
accaaggtcc acataaaagt tttgcaaact gtgatctcct tcttcttgtt acgtgccatt      720
tactttgtgt ctgtaataat atcagtttgg agttttaaga atctggaaaa caaacctgtc      780
ttcatgttct gccaagctat tggattcagc tgttcttcag cccacccgtt catcctgatt      840
tggggaaaca agaagctaaa gcagacttat ctttcagttt tgtggcaaat gaggtactga      900
```

<210> SEQ ID NO 54
<211> LENGTH: 299
<212> TYPE: PRT
<213> ORGANISM: homo sapiens

<400> SEQUENCE: 54

```
Met Ile Thr Phe Leu Pro Ile Ile Phe Ser Ile Leu Val Val Thr
1               5                   10                  15

Phe Val Ile Gly Asn Phe Ala Asn Gly Phe Ile Ala Leu Val Asn Ser
            20                  25                  30

Thr Glu Trp Val Lys Arg Gln Lys Ile Ser Phe Ala Asp Gln Ile Val
        35                  40                  45

Thr Ala Leu Ala Val Ser Arg Val Gly Leu Leu Trp Val Leu Leu
    50                  55                  60

Asn Trp Tyr Ser Thr Val Leu Asn Pro Ala Phe Cys Ser Val Glu Leu
65                  70                  75                  80

Arg Thr Thr Ala Tyr Asn Ile Trp Ala Val Thr Gly His Phe Ser Asn
                85                  90                  95

Trp Pro Ala Thr Ser Leu Ser Ile Phe Tyr Leu Leu Lys Ile Ala Asn
            100                 105                 110

Phe Ser Asn Leu Ile Phe Leu Arg Leu Lys Arg Arg Val Lys Ser Val
        115                 120                 125

Ile Leu Val Val Leu Leu Gly Pro Leu Leu Phe Leu Ala Cys His Leu
    130                 135                 140

Phe Val Val Asn Met Asn Gln Ile Val Trp Thr Lys Glu Tyr Glu Gly
145                 150                 155                 160

Asn Met Thr Trp Lys Ile Lys Leu Arg Arg Ala Met Tyr Leu Ser Asp
                165                 170                 175

Thr Thr Val Thr Met Leu Ala Asn Leu Val Pro Phe Thr Val Thr Leu
            180                 185                 190

Ile Ser Phe Leu Leu Leu Val Cys Ser Leu Cys Lys His Leu Lys Lys
        195                 200                 205

Met Gln Leu His Gly Lys Gly Ser Gln Asp Pro Ser Thr Lys Val His
    210                 215                 220

Ile Lys Val Leu Gln Thr Val Ile Ser Phe Phe Leu Leu Arg Ala Ile
225                 230                 235                 240

Tyr Phe Val Ser Val Ile Ile Ser Val Trp Ser Phe Lys Asn Leu Glu
                245                 250                 255

Asn Lys Pro Val Phe Met Phe Cys Gln Ala Ile Gly Phe Ser Cys Ser
            260                 265                 270

Ser Ala His Pro Phe Ile Leu Ile Trp Gly Asn Lys Lys Leu Lys Gln
        275                 280                 285

Thr Tyr Leu Ser Val Leu Trp Gln Met Arg Tyr
    290                 295
```

<210> SEQ ID NO 55
<211> LENGTH: 1002
<212> TYPE: DNA
<213> ORGANISM: homo sapiens

<400> SEQUENCE: 55

```
atgttgactc taactcgcat ccgcactgtg tcctatgaag tcaggagtac atttctgttc      60
atttcagtcc tggagtttgc agtggggttt ctgaccaatg ccttcgtttt cttggtgaat     120
ttttgggatg tagtgaagag gcaggcactg agcaacagtg attgtgtgct gctgtgtctc     180
agcatcagcc ggcttttcct gcatggactg ctgttcctga gtgctatcca gcttacccac     240
ttccagaagt tgagtgaacc actgaaccac agctaccaag ccatcatcat gctatggatg     300
attgcaaacc aagccaacct ctggcttgct gcctgcctca gcctgcttta ctgctccaag     360
ctcatccgtt tctctcacac cttcctgatc tgcttggcaa gctgggtctc aggaagatc      420
tcccagatgc tcctgggtat tattctttgc tcctgcatct gcactgtcct ctgtgtttgg     480
tgcttttta gcagacctca cttcacagtc acaactgtgc tattcatgaa taacaataca     540
aggctcaact ggcagattaa agatctcaat ttatttttatt cctttctctt ctgctatctg     600
tggtctgtgc ctcctttcct attgtttctg gtttcttctg ggatgctgac tgtctccctg     660
ggaaggcaca tgaggacaat gaaggtctat accagaaact ctcgtgaccc cagcctggag     720
gcccacatta agccctcaa gtctcttgtc tccttttct gcttctttgt gatatcatcc       780
tgtgctgcct tcatctctgt gcccctactg attctgtggc gcgacaaaat aggggtgatg     840
gtttgtgttg ggataatggc agcttgtccc tctgggcatg cagccatcct gatctcaggc     900
aatgccaagt tgaggagagc tgtgatgacc attctgctct gggctcagag cagcctgaag     960
gtaagagccg accacaaggc agattcccgg acactgtgct ga                       1002
```

<210> SEQ ID NO 56
<211> LENGTH: 333
<212> TYPE: PRT
<213> ORGANISM: homo sapiens

<400> SEQUENCE: 56

```
Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Ala Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
    130                 135                 140

Leu Gly Ile Ile Leu Cys Ser Cys Ile Cys Thr Val Leu Cys Val Trp
```

| | 145 | | | 150 | | | 155 | | | 160 | |
|---|---|---|---|---|---|---|---|---|---|---|---|

Cys Phe Phe Ser Arg Pro His Phe Thr Val Thr Thr Val Leu Phe Met
                165                  170               175

Asn Asn Asn Thr Arg Leu Asn Trp Gln Ile Lys Asp Leu Asn Leu Phe
                180                  185               190

Tyr Ser Phe Leu Phe Cys Tyr Leu Trp Ser Val Pro Pro Phe Leu Leu
        195                  200                  205

Phe Leu Val Ser Ser Gly Met Leu Thr Val Ser Leu Gly Arg His Met
    210                  215                  220

Arg Thr Met Lys Val Tyr Thr Arg Asn Ser Arg Asp Pro Ser Leu Glu
225                  230                  235              240

Ala His Ile Lys Ala Leu Lys Ser Leu Val Ser Phe Phe Cys Phe Phe
                245                  250               255

Val Ile Ser Ser Cys Ala Ala Phe Ile Ser Val Pro Leu Leu Ile Leu
        260                  265                  270

Trp Arg Asp Lys Ile Gly Val Met Val Cys Val Gly Ile Met Ala Ala
    275                  280                  285

Cys Pro Ser Gly His Ala Ala Ile Leu Ile Ser Gly Asn Ala Lys Leu
        290                  295                  300

Arg Arg Ala Val Met Thr Ile Leu Leu Trp Ala Gln Ser Ser Leu Lys
305                  310                  315              320

Val Arg Ala Asp His Lys Ala Asp Ser Arg Thr Leu Cys
                325                  330

<210> SEQ ID NO 57
<211> LENGTH: 1017
<212> TYPE: DNA
<213> ORGANISM: homo sapiens

<400> SEQUENCE: 57

```
atgctaggga gatgttttcc tccagacacc aaagagaagc aacagctcag aatgactaaa      60
ctctgcgatc ctgcagaaag tgaattgtcg ccattctca tcaccttaat tttagcagtt     120
ttacttgctg aatacctcat tggtatcatt gcaaatggtt tcatcatggc tatacatgca     180
gctgaatggg ttcaaaataa ggcagtttcc acaagtggca ggatcctggt tttcctgagt     240
gtatccagaa tagctctcca aagcctcatg atgttagaaa ttaccatcag ctcaacctcc     300
ctaagttttt attctgaaga cgctgtatat tatgcattca aaataagttt tatattctta     360
aattttgta gcctgtggtt tgctgcctgg ctcagtttct tctactttgt gaagattgcc     420
aatttctcct acccccttt cctcaaactg aggtggagaa ttactggatt gatacctgg     480
cttctgtggc tgtccgtgtt tatttccttc agtcacagca tgttctgcat caacatctgc     540
actgtgtatt gtaacaattc tttccctatc cactcctcca actccactaa gaaaacatac     600
ttgtctgaga tcaatgtggt cggtctggct tttttcttta acctggggat tgtgactcct     660
ctgatcatgt tcatcctgac agccacccctg ctgatcctct ctctcaagag acacacccta     720
cacatgggaa gcaatgccac agggtccaac gaccccagca tggaggctca catggggggcc     780
atcaaagcta tcagctactt tctcattctc tacattttca atgcagttgc tctgtttatc     840
tacctgtcca acatgtttga catcaacagt ctgtggaata atttgtgcca gatcatcatg     900
gctgcctacc tgccagccac tcaattctat ctgattcaag ataaccctgg gctgagaaga     960
gcctggaagc ggcttcagct tcgacttcat ctttacccaa aagagtggac tctgtga     1017
```

<210> SEQ ID NO 58

<211> LENGTH: 338
<212> TYPE: PRT
<213> ORGANISM: homo sapiens

<400> SEQUENCE: 58

```
Met Leu Gly Arg Cys Phe Pro Pro Asp Thr Lys Glu Lys Gln Gln Leu
1               5                   10                  15

Arg Met Thr Lys Leu Cys Asp Pro Ala Glu Ser Glu Leu Ser Pro Phe
            20                  25                  30

Leu Ile Thr Leu Ile Leu Ala Val Leu Leu Ala Glu Tyr Leu Ile Gly
        35                  40                  45

Ile Ile Ala Asn Gly Phe Ile Met Ala Ile His Ala Ala Glu Trp Val
    50                  55                  60

Gln Asn Lys Ala Val Ser Thr Ser Gly Arg Ile Leu Val Phe Leu Ser
65                  70                  75                  80

Val Ser Arg Ile Ala Leu Gln Ser Leu Met Met Leu Glu Ile Thr Ile
                85                  90                  95

Ser Ser Thr Ser Leu Ser Phe Tyr Ser Glu Asp Ala Val Tyr Tyr Ala
            100                 105                 110

Phe Lys Ile Ser Phe Ile Phe Leu Asn Phe Cys Ser Leu Trp Phe Ala
        115                 120                 125

Ala Trp Leu Ser Phe Phe Tyr Phe Val Lys Ile Ala Asn Phe Ser Tyr
    130                 135                 140

Pro Leu Phe Leu Lys Leu Arg Trp Arg Ile Thr Gly Leu Ile Pro Trp
145                 150                 155                 160

Leu Leu Trp Leu Ser Val Phe Ile Ser Phe Ser His Ser Met Phe Cys
                165                 170                 175

Ile Asn Ile Cys Thr Val Tyr Cys Asn Asn Ser Phe Pro Ile His Ser
            180                 185                 190

Ser Asn Ser Thr Lys Lys Thr Tyr Leu Ser Glu Ile Asn Val Val Gly
        195                 200                 205

Leu Ala Phe Phe Phe Asn Leu Gly Ile Val Thr Pro Leu Ile Met Phe
    210                 215                 220

Ile Leu Thr Ala Thr Leu Leu Ile Leu Ser Leu Lys Arg His Thr Leu
225                 230                 235                 240

His Met Gly Ser Asn Ala Thr Gly Ser Asn Asp Pro Ser Met Glu Ala
                245                 250                 255

His Met Gly Ala Ile Lys Ala Ile Ser Tyr Phe Leu Ile Leu Tyr Ile
            260                 265                 270

Phe Asn Ala Val Ala Leu Phe Ile Tyr Leu Ser Asn Met Phe Asp Ile
        275                 280                 285

Asn Ser Leu Trp Asn Asn Leu Cys Gln Ile Ile Met Ala Ala Tyr Pro
    290                 295                 300

Ala Ser His Ser Ile Leu Leu Ile Gln Asp Asn Pro Gly Leu Arg Arg
305                 310                 315                 320

Ala Trp Lys Arg Leu Gln Leu Arg Leu His Leu Tyr Pro Lys Glu Trp
                325                 330                 335

Thr Leu
```

<210> SEQ ID NO 59
<211> LENGTH: 972
<212> TYPE: DNA
<213> ORGANISM: homo sapiens

<400> SEQUENCE: 59

```
atggcaacgg tgaacacaga tgccacagat aaagacatat ccaagttcaa ggtcaccttc    60
actttggtgg tctccggaat agagtgcatc actggcatcc ttgggagtgg cttcatcacg   120
gccatctatg gggctgagtg ggccagggc  aaaacactcc ccactggtga ccgcattatg   180
ttgatgctga gcttttccag gctcttgcta cagatttgga tgatgctgga gaacattttc   240
agtctgctat tccgaattgt ttataaccaa aactcagtgt atatcctctt caaagtcatc   300
actgtctttc tgaaccattc caatctctgg tttgctgcct ggctcaaagt cttctattgt   360
cttagaattg caaacttcaa tcatcctttg ttcttcctga tgaagaggaa aatcatagtg   420
ctgatgcctt ggcttctcag gctgtcagtg ttggtttcct taagcttcag ctttcctctc   480
tcgagagatg tcttcaatgt gtatgtgaat agctccattc ctatcccctc ctccaactcc   540
acggagaaga agtacttctc tgagaccaat atggtcaacc tggtatttt  ctataacatg   600
gggatcttcg ttcctctgat catgttcatc ctggcagcca ccctgctgat cctctctctc   660
aagagacaca ccctacacat gggaagcaat gccacagggt ccagggaccc cagcatgaag   720
gctcacatag gggccatcaa agccaccagc tactttctca tcctctacat ttcaatgca   780
attgctctat ttcttccac  gtccaacatc tttgacactt acagttcctg aatattttg    840
tgcaagatca tcatggctgc ctaccctgcc ggccactcag tacaactgat cttgggcaac   900
cctgggctga aagagcctg  gaagcggttt cagcaccaag ttcctcttta cctaaaaggg   960
cagactctgt ga                                                       972
```

<210> SEQ ID NO 60
<211> LENGTH: 323
<212> TYPE: PRT
<213> ORGANISM: homo sapiens

<400> SEQUENCE: 60

```
Met Ala Thr Val Asn Thr Asp Ala Thr Asp Lys Asp Ile Ser Lys Phe
1               5                   10                  15

Lys Val Thr Phe Thr Leu Val Val Ser Gly Ile Glu Cys Ile Thr Gly
            20                  25                  30

Ile Leu Gly Ser Gly Phe Ile Thr Ala Ile Tyr Gly Ala Glu Trp Ala
        35                  40                  45

Arg Gly Lys Thr Leu Pro Thr Gly Asp Arg Ile Met Leu Met Leu Ser
    50                  55                  60

Phe Ser Arg Leu Leu Leu Gln Ile Trp Met Met Leu Glu Asn Ile Phe
65                  70                  75                  80

Ser Leu Leu Phe Arg Ile Val Tyr Asn Gln Asn Ser Val Tyr Ile Leu
                85                  90                  95

Phe Lys Val Ile Thr Val Phe Leu Asn His Ser Asn Leu Trp Phe Ala
            100                 105                 110

Ala Trp Leu Lys Val Phe Tyr Cys Leu Arg Ile Ala Asn Phe Asn His
        115                 120                 125

Pro Leu Phe Phe Leu Met Lys Arg Lys Ile Ile Val Leu Met Pro Trp
    130                 135                 140

Leu Leu Arg Leu Ser Val Leu Val Ser Leu Ser Phe Ser Phe Pro Leu
145                 150                 155                 160

Ser Arg Asp Val Phe Asn Val Tyr Val Asn Ser Ser Ile Pro Ile Pro
                165                 170                 175

Ser Ser Asn Ser Thr Glu Lys Lys Tyr Phe Ser Glu Thr Asn Met Val
            180                 185                 190

Asn Leu Val Phe Phe Tyr Asn Met Gly Ile Phe Val Pro Leu Ile Met
```

```
                195                 200                 205
Phe Ile Leu Ala Ala Thr Leu Leu Ile Leu Ser Leu Lys Arg His Thr
210                 215                 220

Leu His Met Gly Ser Asn Ala Thr Gly Ser Arg Asp Pro Ser Met Lys
225                 230                 235                 240

Ala His Ile Gly Ala Ile Lys Ala Thr Ser Tyr Phe Leu Ile Leu Tyr
                245                 250                 255

Ile Phe Asn Ala Ile Ala Leu Phe Leu Ser Thr Ser Asn Ile Phe Asp
                260                 265                 270

Thr Tyr Ser Ser Trp Asn Ile Leu Cys Lys Ile Ile Met Ala Ala Tyr
                275                 280                 285

Pro Ala Gly His Ser Val Gln Leu Ile Leu Gly Asn Pro Gly Leu Arg
                290                 295                 300

Arg Ala Trp Lys Arg Phe Gln His Gln Val Pro Leu Tyr Leu Lys Gly
305                 310                 315                 320

Gln Thr Leu

<210> SEQ ID NO 61
<211> LENGTH: 930
<212> TYPE: DNA
<213> ORGANISM: homo sapiens

<400> SEQUENCE: 61
atgataactt ttctacccat cattttttcc agtctggtag tggttacatt tgttattgga      60
aattttgcta atggcttcat agcactggta aattccattg agtggttcaa gagacaaaag     120
atctcctttg ctgaccaaat tctcactgct ctggcggtct ccagagttgg tttgctctgg     180
gtattattat taaactggta ttcaactgtg ttgaatccag cttttaatag tgtagaagta     240
agaactactg cttataatat ctgggcagtg atcaaccatt tcagcaactg gcttgctact     300
accctcagca tattttattt gctcaagatt gccaatttct ccaactttat ttttcttcac     360
ttaaagagga gagttaagag tgtcattctg gtgatgttgt tggggccttt gctattttg     420 gcttgtcatc ttttttgtgat aaacatgaat gagattgtgc ggacaaaaga atttgaagga     480
aacatgactt ggaagatcaa attgaagagt gcaatgtact tttcaaatat gactgtaacc     540
atggtagcaa acttagtacc cttcactctg accctactat cttttatgct gttaatctgt     600
tctttgtgta aacatctcaa gaagatgcag ctccatggta aaggatctca agatcccagc     660
accaaggtcc acataaaagc tttgcaaact gtgatctcct tcctcttgtt atgtgccatt     720
tactttctgt ccataatgat atcagtttgg agttttggaa gtctggaaaa caaacctgtc     780
ttcatgttct gcaaagctat tagattcagc tatccttcaa tccacccatt catcctgatt     840
tggggaaaca gaagctaaa gcagactttt ctttcagttt tttggcaaat gaggtactgg     900
gtgaaaggag agaagacttc atctccatag                                      930

<210> SEQ ID NO 62
<211> LENGTH: 309
<212> TYPE: PRT
<213> ORGANISM: homo sapiens

<400> SEQUENCE: 62

Met Ile Thr Phe Leu Pro Ile Ile Phe Ser Ser Leu Val Val Thr
1               5                   10                  15

Phe Val Ile Gly Asn Phe Ala Asn Gly Phe Ile Ala Leu Val Asn Ser
                20                  25                  30
```

Ile Glu Trp Phe Lys Arg Gln Lys Ile Ser Phe Ala Asp Gln Ile Leu
             35                  40                  45

Thr Ala Leu Ala Val Ser Arg Val Gly Leu Leu Trp Val Leu Leu
 50                  55                  60

Asn Trp Tyr Ser Thr Val Leu Asn Pro Ala Phe Asn Ser Val Glu Val
 65                  70                  75                  80

Arg Thr Thr Ala Tyr Asn Ile Trp Ala Val Ile Asn His Phe Ser Asn
                 85                  90                  95

Trp Leu Ala Thr Thr Leu Ser Ile Phe Tyr Leu Lys Ile Ala Asn
                100                 105                 110

Phe Ser Asn Phe Ile Phe Leu His Leu Lys Arg Arg Val Lys Ser Val
                115                 120                 125

Ile Leu Val Met Leu Leu Gly Pro Leu Leu Phe Leu Ala Cys His Leu
130                 135                 140

Phe Val Ile Asn Met Asn Glu Ile Val Arg Thr Lys Glu Phe Glu Gly
145                 150                 155                 160

Asn Met Thr Trp Lys Ile Lys Leu Lys Ser Ala Met Tyr Phe Ser Asn
                165                 170                 175

Met Thr Val Thr Met Val Ala Asn Leu Val Pro Phe Thr Leu Thr Leu
                180                 185                 190

Leu Ser Phe Met Leu Leu Ile Cys Ser Leu Cys Lys His Leu Lys Lys
            195                 200                 205

Met Gln Leu His Gly Lys Gly Ser Gln Asp Pro Ser Thr Lys Val His
210                 215                 220

Ile Lys Ala Leu Gln Thr Val Ile Ser Phe Leu Leu Leu Cys Ala Ile
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
                260                 265                 270

Ser Ile His Pro Phe Ile Leu Ile Trp Gly Asn Lys Lys Leu Lys Gln
            275                 280                 285

Thr Phe Leu Ser Val Phe Trp Gln Met Arg Tyr Trp Val Lys Gly Glu
290                 295                 300

Lys Thr Ser Ser Pro
305

<210> SEQ ID NO 63
<211> LENGTH: 930
<212> TYPE: DNA
<213> ORGANISM: homo sapiens

<400> SEQUENCE: 63
atgatgagtt ttctacacat tgttttttcc attctagtag tggttgcatt tattcttgga      60
aattttgcca atggctttat agcactgata aatttcattg cctgggtcaa gagacaaaag    120
atctcctcag ctgatcaaat tattgctgct ctggcagtct ccagagttgg tttgctctgg    180
gtaatattat tacattggta ttcaactgtg ttgaatccaa cttcatctaa tttaaaagta    240 ataatttta tttctaatgc ctgggcagta accaatcatt tcagcatctg gcttgctact    300
agcctcagca tatttatttt gctcaagatc gtcaatttct ccagacttat ttttcatcac    360
ttaaaaagga aggctaagag tgtagttctg gtgatagtgt tggggtctt gttctttttg     420 gtttgtcacc ttgtgatgaa acacacgtat ataaatgtgt ggacagaaga atgtgaagga    480
aacgtaactt ggaagatcaa actgaggaat gcaatgcacc tttccaactt gactgtagcc    540

```
atgctagcaa acttgatacc attcactctg accctgatat cttttctgct gttaatctac    600
tctctgtgta aacatctgaa gaagatgcag ctccatggca aaggatctca agatcccagc    660
accaagatcc acataaaagc tctgcaaact gtgacctcct tcctcatatt acttgccatt    720
tactttctgt gtctaatcat atcgttttgg aattttaaga tgcgaccaaa agaaattgtc    780
ttaatgcttt gccaagcttt tggaatcata tatccatcat tccactcatt cattctgatt    840
tgggggaaca agacgctaaa gcagacccttt ctttcagttt tgtggcaggt gacttgctgg    900
gcaaaaggac agaaccagtc aactccatag                                      930
```

<210> SEQ ID NO 64
<211> LENGTH: 309
<212> TYPE: PRT
<213> ORGANISM: homo sapiens

<400> SEQUENCE: 64

```
Met Met Ser Phe Leu His Ile Val Phe Ser Ile Leu Val Val Ala
1               5                   10                  15

Phe Ile Leu Gly Asn Phe Ala Asn Gly Phe Ile Ala Leu Ile Asn Phe
                20                  25                  30

Ile Ala Trp Val Lys Arg Gln Lys Ile Ser Ser Ala Asp Gln Ile Ile
            35                  40                  45

Ala Ala Leu Ala Val Ser Arg Val Gly Leu Leu Trp Val Ile Leu Leu
        50                  55                  60

His Trp Tyr Ser Thr Val Leu Asn Pro Thr Ser Ser Asn Leu Lys Val
65                  70                  75                  80

Ile Ile Phe Ile Ser Asn Ala Trp Ala Val Thr Asn His Phe Ser Ile
                85                  90                  95

Trp Leu Ala Thr Ser Leu Ser Ile Phe Tyr Leu Leu Lys Ile Val Asn
            100                 105                 110

Phe Ser Arg Leu Ile Phe His His Leu Lys Arg Lys Ala Lys Ser Val
        115                 120                 125

Val Leu Val Ile Val Leu Gly Ser Leu Phe Phe Leu Val Cys His Leu
    130                 135                 140

Val Met Lys His Thr Tyr Ile Asn Val Trp Thr Glu Glu Cys Glu Gly
145                 150                 155                 160

Asn Val Thr Trp Lys Ile Lys Leu Arg Asn Ala Met His Leu Ser Asn
                165                 170                 175

Leu Thr Val Ala Met Leu Ala Asn Leu Ile Pro Phe Thr Leu Thr Leu
            180                 185                 190

Ile Ser Phe Leu Leu Leu Ile Tyr Ser Leu Cys Lys His Leu Lys Lys
        195                 200                 205

Met Gln Leu His Gly Lys Gly Ser Gln Asp Pro Ser Thr Lys Ile His
    210                 215                 220

Ile Lys Ala Leu Gln Thr Val Thr Ser Phe Leu Ile Leu Leu Ala Ile
225                 230                 235                 240

Tyr Phe Leu Cys Leu Ile Ile Ser Phe Trp Asn Phe Lys Met Arg Pro
                245                 250                 255

Lys Glu Ile Val Leu Met Leu Cys Gln Ala Phe Gly Ile Ile Tyr Pro
            260                 265                 270

Ser Phe His Ser Phe Ile Leu Ile Trp Gly Asn Lys Thr Leu Lys Gln
        275                 280                 285

Thr Phe Leu Ser Val Leu Trp Gln Val Thr Cys Trp Ala Lys Gly Gln
    290                 295                 300
```

Asn Gln Ser Thr Pro
305

<210> SEQ ID NO 65
<211> LENGTH: 930
<212> TYPE: DNA
<213> ORGANISM: homo sapiens

<400> SEQUENCE: 65

```
atgacaactt ttatacccat catttttcc agtgtggtag tggttctatt tgttattgga      60
aattttgcta atggcttcat agcattggta aattccattg agcgggtcaa gagacaaaag    120
atctcttttg ctgaccagat tctcactgct ctggcggtct ccagagttgg tttgctctgg    180
gtattattat taaattggta ttcaactgtg tttaatccag cttttttatag tgtagaagta    240
agaactactg cttataatgt ctgggcagta accggccatt tcagcaactg gcttgctact    300
agcctcagca tattttattt gctcaagatt gccaatttct ccaacctat ttttcttcac     360
ttaaagagga gagttaagag tgtcattctg gtgatgctgt tggggccttt actattttg     420
gcttgtcaac tttttgtgat aaacatgaaa gagattgtac ggacaaaaga atatgaagga    480
aacttgactt ggaagatcaa attggaggagt gcagtgtacc tttcagatgc gactgtaacc    540
acgctaggaa acttagtgcc cttcactctg accctgctat gttttttgct gttaatctgt    600
tctctgtgta aacatctcaa gaagatgcag ctccatggta aaggatctca agatcccagc    660
accaaggtcc acataaaagc tttgcaaact gtgatctttt tcctcttgtt atgtgccgtt    720
tactttctgt ccataatgat atcagttgg agttttggga gtctggaaaa caaacctgtc    780
ttcatgttct gcaaagctat tagattcagc tatccttcaa tccacccatt catcctgatt    840
tggggaaaca agaagctaaa gcagactttt ctttcagttt tgcggcaagt gaggtactgg    900
gtgaaaggag agaagccttc atctccatag                                     930
```

<210> SEQ ID NO 66
<211> LENGTH: 309
<212> TYPE: PRT
<213> ORGANISM: homo sapiens

<400> SEQUENCE: 66

```
Met Thr Thr Phe Ile Pro Ile Ile Phe Ser Ser Val Val Val Leu
1               5                   10                  15

Phe Val Ile Gly Asn Phe Ala Asn Gly Phe Ile Ala Leu Val Asn Ser
                20                  25                  30

Ile Glu Arg Val Lys Arg Gln Lys Ile Ser Phe Ala Asp Gln Ile Leu
            35                  40                  45

Thr Ala Leu Ala Val Ser Arg Val Gly Leu Leu Trp Val Leu Leu Leu
        50                  55                  60

Asn Trp Tyr Ser Thr Val Phe Asn Pro Ala Phe Tyr Ser Val Glu Val
65                  70                  75                  80

Arg Thr Thr Ala Tyr Asn Val Trp Ala Val Thr Gly His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Ile Leu Val Met Leu Leu Gly Pro Leu Leu Phe Leu Ala Cys Gln Leu
    130                 135                 140
```

Phe Val Ile Asn Met Lys Glu Ile Val Arg Thr Lys Glu Tyr Glu Gly
145                 150                 155                 160

Asn Leu Thr Trp Lys Ile Lys Leu Arg Ser Ala Val Tyr Leu Ser Asp
            165                 170                 175

Ala Thr Val Thr Thr Leu Gly Asn Leu Val Pro Phe Thr Leu Thr Leu
        180                 185                 190

Leu Cys Phe Leu Leu Leu Ile Cys Ser Leu Cys Lys His Leu Lys Lys
    195                 200                 205

Met Gln Leu His Gly Lys Gly Ser Gln Asp Pro Ser Thr Lys Val His
210                 215                 220

Ile Lys Ala Leu Gln Thr Val Ile Phe Phe Leu Leu Cys Ala Val
225                 230                 235                 240

Tyr Phe Leu Ser Ile Met Ile Ser Val Trp Ser Phe Gly Ser Leu Glu
            245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
            275                 280                 285

Thr Phe Leu Ser Val Leu Arg Gln Val Arg Tyr Trp Val Lys Gly Glu
290                 295                 300

Lys Pro Ser Ser Pro
305

<210> SEQ ID NO 67
<211> LENGTH: 900
<212> TYPE: DNA
<213> ORGANISM: homo sapiens

<400> SEQUENCE: 67
atgatgtgtt ttctgctcat catttcatca attctggtag tgtttgcatt tgttcttgga      60
aatgttgcca atggcttcat agccctagta aatgtcattg actgggttaa cacacgaaag     120
atctcctcag ctgagcaaat tctcactgct ctggtggtct ccagaattgg tttactctgg     180
gtcatgttat ccctttggta tgcaactgtg tttaattctg ctttatatgg tttagaagta     240
agaattgttg cttctaatgc ctgggctgta acgaaccatt tcagcatgtg gcttgctgct     300
agcctcagca tattttgttt gctcaagatt gccaatttct ccaaccttat ttctctccac     360
ctaaagaaga gaattaagag tgttgttctg gtgatactgt tggggccctt ggtatttctg     420
atttgtaatc ttgctgtgat aaccatggat gagagagtgt ggacaaaaga atatgaagga     480
aatgtgactt ggaagatcaa attgaggaat gcaatacacc tttcaagctt gactgtaact     540
actctagcaa acctcatacc ctttactctg agcctaatat gttttctgct gttaatctgt     600
tctctttgta acatctcaa gaagatgcgg ctccatagca aaggatctca agatcccagc      660
accaaggtcc atataaaagc tttgcaaact gtgacctcct tcctcatgtt atttgccatt     720
tactttctgt gtataatcac atcaacttgg aatcttagga cacagcagag caaacttgta     780
ctcctgcttt gccaaactgt tgcaatcatg tatccttcat tccactcatt catcctgatt     840
atgggaagta ggaagctaaa acagaccttt cttttcagttt tgtggcagat gacacgctga     900

<210> SEQ ID NO 68
<211> LENGTH: 299
<212> TYPE: PRT
<213> ORGANISM: homo sapiens

<400> SEQUENCE: 68

Met Met Cys Phe Leu Leu Ile Ile Ser Ser Ile Leu Val Val Phe Ala
1               5                   10                  15

Phe Val Leu Gly Asn Val Ala Asn Gly Phe Ile Ala Leu Val Asn Val
            20                  25                  30

Ile Asp Trp Val Asn Thr Arg Lys Ile Ser Ser Ala Glu Gln Ile Leu
        35                  40                  45

Thr Ala Leu Val Val Ser Arg Ile Gly Leu Leu Trp Val Met Leu Phe
    50                  55                  60

Leu Trp Tyr Ala Thr Val Phe Asn Ser Ala Leu Tyr Gly Leu Glu Val
65                  70                  75                  80

Arg Ile Val Ala Ser Asn Ala Trp Ala Val Thr Asn His Phe Ser Met
                85                  90                  95

Trp Leu Ala Ala Ser Leu Ser Ile Phe Cys Leu Leu Lys Ile Ala Asn
            100                 105                 110

Phe Ser Asn Leu Ile Ser Leu His Leu Lys Lys Arg Ile Lys Ser Val
        115                 120                 125

Val Leu Val Ile Leu Leu Gly Pro Leu Val Phe Leu Ile Cys Asn Leu
    130                 135                 140

Ala Val Ile Thr Met Asp Glu Arg Val Trp Thr Lys Glu Tyr Glu Gly
145                 150                 155                 160

Asn Val Thr Trp Lys Ile Lys Leu Arg Asn Ala Ile His Leu Ser Ser
                165                 170                 175

Leu Thr Val Thr Thr Leu Ala Asn Leu Ile Pro Phe Thr Leu Ser Leu
            180                 185                 190

Ile Cys Phe Leu Leu Leu Ile Cys Ser Leu Cys Lys His Leu Lys Lys
        195                 200                 205

Met Arg Leu His Ser Lys Gly Ser Gln Asp Pro Ser Thr Lys Val His
    210                 215                 220

Ile Lys Ala Leu Gln Thr Val Thr Ser Phe Leu Met Leu Phe Ala Ile
225                 230                 235                 240

Tyr Phe Leu Cys Ile Ile Thr Ser Thr Trp Asn Leu Arg Thr Gln Gln
                245                 250                 255

Ser Lys Leu Val Leu Leu Cys Gln Thr Val Ala Ile Met Tyr Pro
            260                 265                 270

Ser Phe His Ser Phe Ile Leu Ile Met Gly Ser Arg Lys Leu Lys Gln
        275                 280                 285

Thr Phe Leu Ser Val Leu Trp Gln Met Thr Arg
    290                 295

<210> SEQ ID NO 69
<211> LENGTH: 900
<212> TYPE: DNA
<213> ORGANISM: homo sapiens

<400> SEQUENCE: 69
atgataactt tcctatacat ttttttttca attctaataa tggttttatt tgttctcgga      60
aactttgcca atggcttcat agcactggta aatttcattg actgggtgaa gagaaaaaag     120
atctcctcag ctgaccaaat tctcactgct ctggcggtct ccagaattgg tttgctctgg     180
gcattattat taaattggta tttaactgtg ttgaatccag cttttatag tgtagaatta      240 agaattactt cttataatgc ctgggttgta accaaccatt tcagcatgtg gcttgctgct     300
aacctcagca tatttatttt gctcaagatt gccaatttct ccaaccttct ttttcttcat     360
ttaaagagga gagttaggag tgtcattctg gtgatactgt tggggacttt gatattttg      420

```
gtttgtcatc ttcttgtggc aaacatggat gagagtatgt gggcagaaga atatgaagga    480
aacatgactg ggaagatgaa attgaggaat acagtacatc tttcatattt gactgtaact    540 acccctatgga gcttcatacc ctttactctg tccctgatat cttttctgat gctaatctgt    600
tctctgtgta acatctcaa gaagatgcag ctccatggag aaggatcgca agatctcagc    660
accaaggtcc acataaaagc tttgcaaact ctgatctcct tcctcttgtt atgtgccatt    720
ttctttctat tcctaatcgt ttcggtttgg agtcctagga ggctgcggaa tgacccggtt    780
gtcatggtta gcaaggctgt tggaaacata tatcttgcat tcgactcatt catcctaatt    840 tggagaaacca agaagctaaa acacacctttt cttttgattt tgtgtcagat taggtgctga   900
```

<210> SEQ ID NO 70
<211> LENGTH: 299
<212> TYPE: PRT
<213> ORGANISM: homo sapiens

<400> SEQUENCE: 70

```
Met Ile Thr Phe Leu Tyr Ile Phe Phe Ser Ile Leu Ile Met Val Leu
1               5                   10                  15

Phe Val Leu Gly Asn Phe Ala Asn Gly Phe Ile Ala Leu Val Asn Phe
            20                  25                  30

Ile Asp Trp Val Lys Arg Lys Lys Ile Ser Ser Ala Asp Gln Ile Leu
        35                  40                  45

Thr Ala Leu Ala Val Ser Arg Ile Gly Leu Leu Trp Ala Leu Leu Leu
    50                  55                  60

Asn Trp Tyr Leu Thr Val Leu Asn Pro Ala Phe Tyr Ser Val Glu Leu
65                  70                  75                  80

Arg Ile Thr Ser Tyr Asn Ala Trp Val Val Thr Asn His Phe Ser Met
                85                  90                  95

Trp Leu Ala Ala Asn Leu Ser Ile Phe Tyr Leu Leu Lys Ile Ala Asn
            100                 105                 110

Phe Ser Asn Leu Leu Phe Leu His Leu Lys Arg Arg Val Arg Ser Val
        115                 120                 125

Ile Leu Val Ile Leu Leu Gly Thr Leu Ile Phe Leu Val Cys His Leu
    130                 135                 140

Leu Val Ala Asn Met Asp Glu Ser Met Trp Ala Glu Glu Tyr Glu Gly
145                 150                 155                 160

Asn Met Thr Gly Lys Met Lys Leu Arg Asn Thr Val His Leu Ser Tyr
                165                 170                 175

Leu Thr Val Thr Thr Leu Trp Ser Phe Ile Pro Phe Thr Leu Ser Leu
            180                 185                 190

Ile Ser Phe Leu Met Leu Ile Cys Ser Leu Cys Lys His Leu Lys Lys
        195                 200                 205

Met Gln Leu His Gly Glu Gly Ser Gln Asp Leu Ser Thr Lys Val His
    210                 215                 220

Ile Lys Ala Leu Gln Thr Leu Ile Ser Phe Leu Leu Leu Cys Ala Ile
225                 230                 235                 240

Phe Phe Leu Phe Leu Ile Val Ser Val Trp Ser Pro Arg Arg Leu Arg
                245                 250                 255

Asn Asp Pro Val Val Met Val Ser Lys Ala Val Gly Asn Ile Tyr Leu
            260                 265                 270

Ala Phe Asp Ser Phe Ile Leu Ile Trp Arg Thr Lys Lys Leu Lys His
        275                 280                 285

Thr Phe Leu Leu Ile Leu Cys Gln Ile Arg Cys
    290                 295
```

<210> SEQ ID NO 71
<211> LENGTH: 924
<212> TYPE: DNA
<213> ORGANISM: homo sapiens

<400> SEQUENCE: 71

```
atgcaagcag cactgacggc cttcttcgtg ttgctctttta gcctgctgag tcttctgggg      60
attgcagcga atggcttcat tgtgctggtg ctgggcaggg agtggctgcg atatggcagg     120
ttgctgccct tggatatgat cctcattagc ttgggtgcct cccgcttctg cctgcagttg     180
gttgggacgg tgcacaactt ctactactct gcccagaagg tcgagtactc tgggggtctc     240
ggccgacagt tcttccatct acactggcac ttcctgaact cagccacctt ctggttttgc     300
agctggctca gtgtcctgtt ctgtgtgaag attgctaaca tcacacactc caccttcctg     360
tggctgaagt ggaggttccc agggtgggtg ccctggctcc tgttgggctc tgtcctgatc     420
tccttcatca taaccctgct gttttttttgg gtgaactacc ctgtatatca gaattttta      480
attagaaaat ttctgggaa catgacctac aagtggaata caaggataga aacatactat      540
ttcccatccc tgaaactggt catctggtca attcctttt ctgttttttct ggtctcaatt     600
atgctgttaa ttaattctct gaggaggcat actcagagaa tgcagcacaa cgggcacagc     660
ctgcaggacc ccagcaccca ggctcacacc agagctctga agtccctcat ctccttcctc     720
attctttatg ctctgtcctt tctgtccctg atcattgatg ccgcaaaatt tatctccatg     780
cagaacgact tttactggcc atggcaaatt gcagtctacc tgtgcatatc tgtccatccc     840
ttcatcctca tcttcagcaa cctcaagctt cgaagcgtgt ctctcgcagct cctgttgttg     900
gcaagggggct tctgggtggc ctag                                           924
```

<210> SEQ ID NO 72
<211> LENGTH: 307
<212> TYPE: PRT
<213> ORGANISM: homo sapiens

<400> SEQUENCE: 72

```
Met Gln Ala Ala Leu Thr Ala Phe Phe Val Leu Leu Phe Ser Leu Leu
1               5                   10                  15

Ser Leu Leu Gly Ile Ala Ala Asn Gly Phe Ile Val Leu Val Leu Gly
            20                  25                  30

Arg Glu Trp Leu Arg Tyr Gly Arg Leu Leu Pro Leu Asp Met Ile Leu
        35                  40                  45

Ile Ser Leu Gly Ala Ser Arg Phe Cys Leu Gln Leu Val Gly Thr Val
    50                  55                  60

His Asn Phe Tyr Tyr Ser Ala Gln Lys Val Glu Tyr Ser Gly Gly Leu
65                  70                  75                  80

Gly Arg Gln Phe Phe His Leu His Trp His Phe Leu Asn Ser Ala Thr
                85                  90                  95

Phe Trp Phe Cys Ser Trp Leu Ser Val Leu Phe Cys Val Lys Ile Ala
            100                 105                 110

Asn Ile Thr His Ser Thr Phe Leu Trp Leu Lys Trp Arg Phe Pro Gly
        115                 120                 125

Trp Val Pro Trp Leu Leu Leu Gly Ser Val Leu Ile Ser Phe Ile Ile
    130                 135                 140

Thr Leu Leu Phe Phe Trp Val Asn Tyr Pro Val Tyr Gln Glu Phe Leu
145                 150                 155                 160
```

```
Ile Arg Lys Phe Ser Gly Asn Met Thr Tyr Lys Trp Asn Thr Arg Ile
            165                 170                 175

Glu Thr Tyr Tyr Phe Pro Ser Leu Lys Leu Val Ile Trp Ser Ile Pro
        180                 185                 190

Phe Ser Val Phe Leu Val Ser Ile Met Leu Leu Ile Asn Ser Leu Arg
            195                 200                 205

Arg His Thr Gln Arg Met Gln His Asn Gly His Ser Leu Gln Asp Pro
        210                 215                 220

Ser Thr Gln Ala His Thr Arg Ala Leu Lys Ser Leu Ile Ser Phe Leu
225                 230                 235                 240

Ile Leu Tyr Ala Leu Ser Phe Leu Ser Leu Ile Ile Asp Ala Ala Lys
                245                 250                 255

Phe Ile Ser Met Gln Asn Asp Phe Tyr Trp Pro Trp Gln Ile Ala Val
            260                 265                 270

Tyr Leu Cys Ile Ser Val His Pro Phe Ile Leu Ile Phe Ser Asn Leu
        275                 280                 285

Lys Leu Arg Ser Val Phe Ser Gln Leu Leu Leu Leu Ala Arg Gly Phe
    290                 295                 300

Trp Val Ala
305

<210> SEQ ID NO 73
<211> LENGTH: 930
<212> TYPE: DNA
<213> ORGANISM: homo sapiens

<400> SEQUENCE: 73
atgataactt ttctgcccat cattttttcc attctaatag tggttacatt tgtgattgga      60
aattttgcta atggcttcat agcattggta aattccattg agtggttcaa gagacaaaag     120
atctcttttg ctgaccaaat tctcactgct ctggcagtct ccagagttgg tttactctgg     180
gtattagtat taaattggta tgcaactgag ttgaatccag cttttaacag tatagaagta     240
agaattactg cttacaatgt ctgggcagta atcaaccatt tcagcaactg gcttgctact     300
agcctcagca tattttattt gctcaagatt gccaattttct ccaaccttat tttctcttcac    360 ttaaagagga gagttaagag tgttgttctg gtgatactat ggggcctttt gctattttg      420 gtttgtcatc ttttttgtgat aaacatgaat cagattatat ggacaaaaga atatgaagga    480
aacatgactt ggaagatcaa actgaggagt gcaatgtacc tttcaaatac aacggtaacc    540
atcctagcaa acttagttcc cttcactctg accctgatat cttttctgct gttaatctgt    600
tctctgtgta acatctcaa aaagatgcag ctccatggca aaggatctca agatcccagc     660
atgaaggtcc acataaaagc tttgcaaact gtgacctcct tcctcttgtt atgtgccatt    720
tactttctgt ccataatcat gtcagtttgg agttttgaga gtctggaaaa caaacctgtc    780
ttcatgttct gcgaagctat tgcattcagc tatccttcaa cccacccatt catcctgatt    840
tggggaaaca agaagctaaa gcagactttt ctttcagttt tgtggcatgt gaggtactgg    900
gtgaaaggag agaagccttc atcttcatag                                      930

<210> SEQ ID NO 74
<211> LENGTH: 309
<212> TYPE: PRT
<213> ORGANISM: homo sapiens

<400> SEQUENCE: 74
```

Met Ile Thr Phe Leu Pro Ile Ile Phe Ser Ile Leu Ile Val Val Thr
1               5                   10                  15

Phe Val Ile Gly Asn Phe Ala Asn Gly Phe Ile Ala Leu Val Asn Ser
            20                  25                  30

Ile Glu Trp Phe Lys Arg Gln Lys Ile Ser Phe Ala Asp Gln Ile Leu
        35                  40                  45

Thr Ala Leu Ala Val Ser Arg Val Gly Leu Leu Trp Val Leu Val Leu
    50                  55                  60

Asn Trp Tyr Ala Thr Glu Leu Asn Pro Ala Phe Asn Ser Ile Glu Val
65                  70                  75                  80

Arg Ile Thr Ala Tyr Asn Val Trp Ala Val Ile Asn His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Val Leu Val Ile Leu Leu Gly Pro Leu Leu Phe Leu Val Cys His Leu
    130                 135                 140

Phe Val Ile Asn Met Asn Gln Ile Ile Trp Thr Lys Glu Tyr Glu Gly
145                 150                 155                 160

Asn Met Thr Trp Lys Ile Lys Leu Arg Ser Ala Met Tyr Leu Ser Asn
                165                 170                 175

Thr Thr Val Thr Ile Leu Ala Asn Leu Val Pro Phe Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Met Lys Val His
    210                 215                 220

Ile Lys Ala Leu Gln Thr Val Thr Ser Phe Leu Leu Cys Ala Ile
225                 230                 235                 240

Tyr Phe Leu Ser Ile Ile Met Ser Val Trp Ser Phe Glu Ser Leu Glu
                245                 250                 255

Asn Lys Pro Val Phe Met Phe Cys Glu Ala Ile Ala Phe Ser Tyr Pro
            260                 265                 270

Ser Thr His Pro Phe Ile Leu Ile Trp Gly Asn Lys Lys Leu Lys Gln
        275                 280                 285

Thr Phe Leu Ser Val Leu Trp His Val Arg Tyr Trp Val Lys Gly Glu
    290                 295                 300

Lys Pro Ser Ser Ser
305

<210> SEQ ID NO 75
<211> LENGTH: 957
<212> TYPE: DNA
<213> ORGANISM: homo sapiens

<400> SEQUENCE: 75
atgaatggag accacatggt tctaggatct tcggtgactg acaagaaggc catcatcttg     60
gttaccattt tactcctttt acgcctggta gcaatagcag gcaatggctt catcactgct    120
gctctgggcg tggagtgggt gctacggaga atgttgttgc cttgtgataa gttattggtt    180
agcctagggg cctctcgctt ctgtctgcag tcagtggtaa tgggtaagac catttatgtt    240
ttcttgcatc cgatggcctt cccatacaac cctgtactgc agtttctagc tttccagtgg    300
gacttcctga atgctgccac cttatggtcc tctacctggc tcagtgtctt ctattgtgtg    360

```
aaaattgcta ccttcaccca ccctgtcttc ttctggctaa agcacaagtt gtctgggtgg    420
ctaccatgga tgctcttcag ctctgtaggg ctctccagct tcaccaccat tctattttc    480 ataggcaacc acagaatgta tcagaactat ttaaggaacc atctacaacc ttggaatgtc    540
actggcgata gcatacggag ctactgtgag aaattctatc tcttccctct aaaaatgatt    600
acttggacaa tgcccactgc tgtcttttc atttgcatga ttttgctcat cacatctctg    660
ggaagacaca ggaagaaggc tctccttaca acctcaggat tccgagagcc agtgtgcag    720 gcacacataa aggctctgct ggctctcctc tcttttgcca tgctcttcat ctcatatttc    780
ctgtcactgg tgttcagtgc tgcaggtatt tttccacctc tggactttaa attctgggtg    840
tgggagtcag tgatttatct gtgtgcagca gttcaccca tcattctgct cttcagcaac    900
tgcaggctga gagctgtgct gaagagtcgt cgttcctcaa ggtgtgggac accttga      957
```

```
<210> SEQ ID NO 76
<211> LENGTH: 318
<212> TYPE: PRT
<213> ORGANISM: homo sapiens

<400> SEQUENCE: 76
```

```
Met Asn Gly Asp His Met Val Leu Gly Ser Val Thr Asp Lys Lys
1               5                   10                  15

Ala Ile Ile Leu Val Thr Ile Leu Leu Leu Arg Leu Val Ala Ile
            20                  25                  30

Ala Gly Asn Gly Phe Ile Thr Ala Ala Leu Gly Val Glu Trp Val Leu
        35                  40                  45

Arg Arg Met Leu Leu Pro Cys Asp Lys Leu Leu Val Ser Leu Gly Ala
    50                  55                  60

Ser Arg Phe Cys Leu Gln Ser Val Val Met Gly Lys Thr Ile Tyr Val
65                  70                  75                  80

Phe Leu His Pro Met Ala Phe Pro Tyr Asn Pro Val Leu Gln Phe Leu
                85                  90                  95

Ala Phe Gln Trp Asp Phe Leu Asn Ala Ala Thr Leu Trp Ser Ser Thr
            100                 105                 110

Trp Leu Ser Val Phe Tyr Cys Val Lys Ile Ala Thr Phe Thr His Pro
        115                 120                 125

Val Phe Phe Trp Leu Lys His Lys Leu Ser Gly Trp Leu Pro Trp Met
    130                 135                 140

Leu Phe Ser Ser Val Gly Leu Ser Ser Phe Thr Thr Ile Leu Phe Phe
145                 150                 155                 160

Ile Gly Asn His Arg Met Tyr Gln Asn Tyr Leu Arg Asn His Leu Gln
                165                 170                 175

Pro Trp Asn Val Thr Gly Asp Ser Ile Arg Ser Tyr Cys Glu Lys Phe
            180                 185                 190

Tyr Leu Phe Pro Leu Lys Met Ile Thr Trp Thr Met Pro Thr Ala Val
        195                 200                 205

Phe Phe Ile Cys Met Ile Leu Leu Ile Thr Ser Leu Gly Arg His Arg
    210                 215                 220

Lys Lys Ala Leu Leu Thr Thr Ser Gly Phe Arg Glu Pro Ser Val Gln
225                 230                 235                 240

Ala His Ile Lys Ala Leu Leu Ala Leu Leu Ser Phe Ala Met Leu Phe
                245                 250                 255

Ile Ser Tyr Phe Leu Ser Leu Val Phe Ser Ala Ala Gly Ile Phe Pro
            260                 265                 270
```

```
Pro Leu Asp Phe Lys Phe Trp Val Trp Glu Ser Val Ile Tyr Leu Cys
        275                 280                 285

Ala Ala Val His Pro Ile Ile Leu Leu Phe Ser Asn Cys Arg Leu Arg
    290                 295                 300

Ala Val Leu Lys Ser Arg Arg Ser Ser Arg Cys Gly Thr Pro
305                 310                 315

<210> SEQ ID NO 77
<211> LENGTH: 936
<212> TYPE: DNA
<213> ORGANISM: artificial
<220> FEATURE:
<223> OTHER INFORMATION: Rluc humanized

<400> SEQUENCE: 77
atgaccagca aggtgtacga ccccgagcag aggaagagga tgatcaccgg cccccagtgg     60
tgggccaggt gcaagcagat gaacgtgctg gacagcttca tcaactacta cgacagcgag    120
aagcacgccg agaacgccgt gatcttcctg cacggcaacg ccgctagcag ctacctgtgg    180
aggcacgtgg tgccccacat cgagcccgtg gccaggtgca tcatccccga tctgatcggc    240
atgggcaaga gcggcaagag cggcaacggc agctacaggc tgctggacca ctacaagtac    300
ctgaccgcct ggttcgagct cctgaacctg cccaagaaga tcatcttcgt gggccacgac    360
tggggcgcct gcctggcctt ccactacagc tacgagcacc aggacaagat caaggccatc    420
gtgcacgccg agagcgtggt ggacgtgatc gagagctggg acgagtggcc agacatcgag    480
gaggacatcg ccctgatcaa gagcgaggag ggcgagaaga tggtgctgga aacaacttc    540 ttcgtggaga ccatgctgcc cagcaagatc atgagaaagc tggagcccga ggagttcgcc    600
gcctacctgg agcccttcaa ggagaagggc gaggtgagaa gacccacccT gagctggccc    660
agagagatcc ccctggtgaa gggcggcaag cccgacgtgg tgcagatcgt gagaaactac    720
aacgcctacc tgagagccag cgacgacctg cccaagatgt tcatcgagag cgaccccggc    780
ttcttcagca acgccatcgt ggagggcgcc aagaagttcc ccaacaccga gttcgtgaag    840
gtgaagggcc tgcacttcag ccaggaggac gcccccgacg agatgggcaa gtacatcaag    900
agcttcgtgg agagagtgct gaagaacgag cagtaa                              936

<210> SEQ ID NO 78
<211> LENGTH: 311
<212> TYPE: PRT
<213> ORGANISM: artificial
<220> FEATURE:
<223> OTHER INFORMATION: Humanized Rluc

<400> SEQUENCE: 78

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95
```

```
His Tyr Lys Tyr Leu Thr Ala Trp Phe Glu Leu Leu Asn Leu Pro Lys
                100                 105                 110

Lys Ile Ile Phe Val Gly His Asp Trp Gly Ala Cys Leu Ala Phe His
            115                 120                 125

Tyr Ser Tyr Glu His Gln Asp Lys Ile Lys Ala Ile Val His Ala Glu
        130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Lys Met Val Leu
                165                 170                 175

Glu Asn Asn Phe Phe Val Glu Thr Met Leu Pro Ser Lys Ile Met Arg
                180                 185                 190

Lys Leu Glu Pro Glu Glu Phe Ala Ala Tyr Leu Glu Pro Phe Lys Glu
            195                 200                 205

Lys Gly Glu Val Arg Arg Pro Thr Leu Ser Trp Pro Arg Glu Ile Pro
        210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
        290                 295                 300

Arg Val Leu Lys Asn Glu Gln
305                 310

<210> SEQ ID NO 79
<211> LENGTH: 654
<212> TYPE: PRT
<213> ORGANISM: artificial
<220> FEATURE:
<223> OTHER INFORMATION: GFP2-beta/arrestin-2

<400> SEQUENCE: 79

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140
```

-continued

```
Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Gly Thr Gly Ser Met Gly Glu Lys Pro Gly Thr Arg Val Phe Lys
                245                 250                 255

Lys Ser Ser Pro Asn Cys Lys Leu Thr Val Tyr Leu Gly Lys Arg Asp
                260                 265                 270

Phe Val Asp His Leu Asp Lys Val Asp Pro Val Asp Gly Val Val Leu
                275                 280                 285

Val Asp Pro Asp Tyr Leu Lys Asp Arg Lys Val Phe Val Thr Leu Thr
            290                 295                 300

Cys Ala Phe Arg Tyr Gly Arg Glu Asp Leu Asp Val Leu Gly Leu Ser
305                 310                 315                 320

Phe Arg Lys Asp Leu Phe Ile Ala Thr Tyr Gln Ala Phe Pro Pro Val
                325                 330                 335

Pro Asn Pro Pro Arg Pro Pro Thr Arg Leu Gln Asp Arg Leu Leu Arg
                340                 345                 350

Lys Leu Gly Gln His Ala His Pro Phe Phe Phe Thr Ile Pro Gln Asn
            355                 360                 365

Leu Pro Cys Ser Val Thr Leu Gln Pro Gly Pro Glu Asp Thr Gly Lys
        370                 375                 380

Ala Cys Gly Val Asp Phe Glu Ile Arg Ala Phe Cys Ala Lys Ser Leu
385                 390                 395                 400

Glu Glu Lys Ser His Lys Arg Asn Ser Val Arg Leu Val Ile Arg Lys
                405                 410                 415

Val Gln Phe Ala Pro Glu Lys Pro Gly Pro Gln Pro Ser Ala Glu Thr
            420                 425                 430

Thr Arg His Phe Leu Met Ser Asp Arg Ser Leu His Leu Glu Ala Ser
        435                 440                 445

Leu Asp Lys Glu Leu Tyr Tyr His Gly Glu Pro Leu Asn Val Asn Val
    450                 455                 460

His Val Thr Asn Asn Ser Thr Lys Thr Val Lys Lys Ile Lys Val Ser
465                 470                 475                 480

Val Arg Gln Tyr Ala Asp Ile Cys Leu Phe Ser Thr Ala Gln Tyr Lys
                485                 490                 495

Cys Pro Val Ala Gln Leu Glu Gln Asp Asp Gln Val Ser Pro Ser Ser
                500                 505                 510

Thr Phe Cys Lys Val Tyr Thr Ile Thr Pro Leu Leu Ser Asp Asn Arg
                515                 520                 525

Glu Lys Arg Gly Leu Ala Leu Asp Gly Lys Leu Lys His Glu Asp Thr
            530                 535                 540

Asn Leu Ala Ser Ser Thr Ile Val Lys Glu Gly Ala Asn Lys Glu Val
545                 550                 555                 560
```

```
Leu Gly Ile Leu Val Ser Tyr Arg Val Lys Val Lys Leu Val Val Ser
            565                 570                 575
Arg Gly Gly Asp Val Ser Val Glu Leu Pro Phe Val Leu Met His Pro
        580                 585                 590
Lys Pro His Asp His Ile Pro Leu Pro Arg Pro Gln Ser Ala Ala Pro
    595                 600                 605
Glu Thr Asp Val Pro Val Asp Thr Asn Leu Ile Glu Phe Asp Thr Asn
610                 615                 620
Tyr Ala Thr Asp Asp Ile Val Phe Glu Asp Phe Ala Arg Leu Arg
625                 630                 635                 640
Leu Lys Gly Met Lys Asp Asp Tyr Asp Asp Gln Leu Cys
                645                 650
```

<210> SEQ ID NO 80
<211> LENGTH: 1965
<212> TYPE: DNA
<213> ORGANISM: artificial
<220> FEATURE:
<223> OTHER INFORMATION: GFP2-beta/arrestin-2

<400> SEQUENCE: 80

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca cctgagcta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagggc     720
tccggtaccg gatccatggg ggagaaaccc gggaccaggg tcttcaagaa gtcgagccct     780
aactgcaagc tcaccgtgta cttgggcaag cgggacttcg tagatcacct ggacaaagtg     840
gaccctgtag atgcgtggt gcttgtggac cctgactacc tgaaggaccg caaagtgttt     900
gtgaccctca cctgcgcctt ccgctatggc cgtgaagacc tggatgtgct gggcttgtcc     960
ttccgcaaag acctgttcat cgccacctac caggccttcc ccccggtgcc caacccaccc    1020
cggccccca cccgcctgca ggaccggctg ctgaggaagc tgggccagca tgcccacccc    1080
ttcttcttca ccatacccca gaatcttcca tgctccgtca cactgcagcc aggcccagag    1140
gatacaggaa aggcctgcgg cgtagacttt gagattcgag ccttctgtgc taaatcacta    1200
gaagagaaaa gccacaaaag gaactctgtg cggctggtga tccgaaaggt gcagttcgcc    1260
ccggagaaac ccgcccccca gcttcagcc gaaaccacac gccacttcct catgtctgac    1320
cggtccctgc acctcgaggc ttccctggac aaggagctgt actaccatgg ggagcccctc    1380
aatgtaaatg tccacgtcac caacaactcc accaagaccg tcaagaagat caaagtctct    1440
gtgagacagt acgccgacat ctgcctcttc agcaccgccc agtacaagtg tcctgtggct    1500
caactcgaac aagatgacca ggtatctccc agctccacat tctgtaaggt gtacaccata    1560
```

```
accccactgc tcagtgacaa ccgggagaag cggggtctcg ccctggatgg gaaactcaag    1620
cacgaggaca ccaacctggc ttccagcacc atcgtgaagg agggtgccaa caaggaggtg    1680
ctgggaatcc tggtgtccta cagggtcaag gtgaagctgg tggtgtctcg aggcggggat    1740
gtctctgtgg agctgccttt tgttcttatg caccccaagc cccacgacca catcccctc    1800 cccagacccc agtcagccgc tccggagaca gatgtccctg tggacaccaa cctcattgaa    1860
tttgatacca actatgccac agatgatgac attgtgtttg aggactttgc ccggcttcgg    1920
ctgaagggga tgaaggatga cgactatgat gatcaactct gctag                   1965
```